US007067312B1

(12) United States Patent
Bartel et al.

(10) Patent No.: US 7,067,312 B1
(45) Date of Patent: Jun. 27, 2006

(54) PN7718 NUCLEIC ACIDS AND USE THEREOF

(75) Inventors: Paul Bartel, Salt Lake City, UT (US); Kimberly Ann Mauck, Sandy, UT (US)

(73) Assignee: Myriad Genetics, Inc., Salt Lake City, UT (US)

( * ) Notice: Subject to any disclaimer, the term of this patent is extended or adjusted under 35 U.S.C. 154(b) by 114 days.

(21) Appl. No.: 10/247,146

(22) Filed: Sep. 19, 2002

Related U.S. Application Data

(60) Provisional application No. 60/323,613, filed on Sep. 19, 2001.

(51) Int. Cl.
- *C12N 5/00* (2006.01)
- *C12P 21/06* (2006.01)
- *C07H 21/02* (2006.01)

(52) U.S. Cl. .................. 435/325; 435/69.1; 530/300; 536/23.1

(58) Field of Classification Search .............. 536/23.1, 536/24.1, 24.3, 24.33, 24.5
See application file for complete search history.

(56) References Cited

U.S. PATENT DOCUMENTS

| 5,223,409 A | 6/1993 | Ladner et al. |
| 5,283,173 A | 2/1994 | Fields et al. |
| 5,403,484 A | 4/1995 | Ladner et al. |
| 5,571,698 A | 11/1996 | Ladner et al. |
| 5,837,500 A | 11/1998 | Ladner et al. |
| 6,117,989 A | 9/2000 | Bandman et al. |
| 6,361,971 B1 * | 3/2002 | Rhodes et al. .............. 435/69.1 |
| 6,369,197 B1 | 4/2002 | Rhodes et al. |
| 6,783,969 B1 * | 8/2004 | Tang et al. .................. 435/219 |

FOREIGN PATENT DOCUMENTS

WO    WO 02/26984    4/2002

OTHER PUBLICATIONS

Liu, J., et al., "Calcineurin is a common target of cyclophilin-cyclosporin A and FKBP-FK506 complexes," *Cell*, 1991; 66:807-815.

Tjian, Robert, et al., "Transcriptional Activation: A Complex Puzzle with Few Easy Pieces", *Cell*, Apr. 8, 1994; 77:5-8.

(Continued)

*Primary Examiner*—Sean McGarry
*Assistant Examiner*—Lisa C. Hill
(74) *Attorney, Agent, or Firm*—Drew Gibbs; Jay Z. Zheng; Myriad Genetics IP Department

(57) ABSTRACT

Novel PN7718 protein and nucleic acids encoding PN7718 are provided. PN7718-containing protein complexes formed by PN7718 and a PN7718-interacting protein (e.g., cyclophilin C) are also provided. Cyclophilin C and PN7718 may be involved in common biological processes such as intracellular calcium signaling, beta-amyloid formation, T-cell receptor and IgE receptor signaling pathways, and protein folding and degradation. Thus, the protein complexes as well as PN7718 can be used in screening assays to select modulators of PN7718 and the protein complexes formed by PN7718 and cyclophilin C. The identified modulators can be useful in modulating the functions and activities of PN7718 and protein complexes containing PN7718, and in treating and preventing autoimmune diseases, neurological diseases and cardiovascular disorders.

7 Claims, 1 Drawing Sheet

OTHER PUBLICATIONS

Winter, Dirk, et al., "The complex containing actin-related proteins Arp2 and Arp3 is required for the motility and integrity of yeast actin payches", *Current Biology*, 1997; 7:519-529.

Buxbaum, Joseph D., et al., "Calsenilin: a calcium-binding protein that interacts with the presenilins and regulates the levels of a presenilin fragment," *Nature Medicine*, Oct. 1998; 4(10):1177-1181.

NCBI Entrez Protein Database Accession No.: AF120102, Mar. 15, 1999.

Houry, Walid A., et al., "Identification of in vivo substrates of the chaperonin GroEL", *Nature*, Nov. 11, 1999; 402:147-154.

Rout, Michael P., "The Yeast Nuclear Pore Complex: Composition, Architecture, and Transport Mechanism", *The Journal of Cell Biology*, Feb. 21, 2000; 148(4):635-651.

Eisenberg, David, et al., "Protein function in the post-genomic era", *Nature*, Jun. 15, 2000; 405:823-826.

Leissring, Malcolm A., et al., "Calsenilin reverses presenilin-mediated enhancement of calcium signaling," *Proc. Natl. Acad. Sci.*, Jul. 18, 2000; 97:8590-8593.

Holmqvist, Mats H., et al., "Elimination of fast inactivation in Kv4 A-type potassium channels by an auxiliary submit domain," *Proc. Natl. Acad. Sci.*, Jan. 22, 2002; 99(2):1035-1040.

Morohashi, Yuichi, et. al., "Molecular cloning and characterization of CALP/KChlP4, a novel EF-hand protein interacting with presenilin 2 and voltage-gated potassium channel subunit Kv4," *Journal of Biological Chemistry*, Apr. 26, 2002; 277(17):14965-14975.

\* cited by examiner

SEQUENCE LISTING

<160> NUMBER OF SEQ ID NOS: 5

<210> SEQ ID NO 1
<211> LENGTH: 2421
<212> TYPE: DNA
<213> ORGANISM: Homo sapiens

<400> SEQUENCE: 1

```
cggcacctgc agcccggtcc gcgcgccctg cccgcagccg ccgccgaagc tctcgctccc      60
agcgccacgg acgccccgg gccgagcggc ggtgcgctcc cgtgcagacc cgtggacaga     120 cgccctggc cggtggactc tcgagtctcg cttctgcacc ctgcgtcccc agacatgaat     180
gtgaggaggg tggaaagcat ttcggctcag ctggaggagg ccagctctac aggcggtttc     240
ctgtacgctc agaacagcac caagcgcagc attaaagagc ggctcatgaa gctcttgccc     300
tgctcagctg ccaaaacgtc gtctcctgct attcaaaaca gcgtggaaga tgaactggag     360
atggccaccg tcaggcatcg gcctgaagcc cttgagcttc tggaagccca gagcaaattt     420
accaagaaag agcttcagat cctttacaga ggatttaaga atgaatgccc cagtggtgtt     480
gttaatgaag aaaccttcaa agagatttac tcgcagttct ttccacaggg agactctaca     540
acatatgcac attttctgtt caatgcattt gatacagacc acaatggagc tgtgagtttc     600
gaggatttca tcaaaggtct ttccattttg ctccggggga cagtacaaga aaaactcaat     660
tgggcattta atctgtatga cataaataaa gatggctaca tcactaaaga ggaaatgctt     720
gatataatga agcaatata cgatatgatg ggtaaatgta catatcctgt cctcaaagaa     780
gatgctccca gacaacacgt tgaaacattt tttcagaaaa tggacaaaaa taagatggg     840 gttgttacca tagatgagtt cattgaaagc tgccaaaaag atgaaaacat aatgcgctcc     900
atgcagctct ttgaaaatgt gatttaactt gtcaaataga tcctgaatcc aacagacaaa     960
tgtgaactat tctaccaccc ttaaagttgg agctaccact tttagcatag attgctcagc    1020
ttgacactga agcatattat gcaaacaagc tttgttttaa tataaagcaa tccccaaaag   1080
```

-continued

```
atttgagctt tcagttataa atttgcatcc ttttcataat gccactgagt tcaggggatg    1140
gtctaactca tttcatactc tgtgaatatt caaaagtaat agaatctggc atatagtttt    1200
attggttcct tagccatggg attattgagg ctttcacata tcagtgattt taaaatatca    1260
gtgttttttg ctactcattt gtatgtattc agtcctagga ttttgaatgg ttttctaata    1320
tagtgacatc tgcatttaat ttccagaaat taaattaatt ttcatgtttg aatgctgtaa    1380
ttccatttaa attccattta tactttttaa ggaaacaaga ttacaacaat taaaaaaaca    1440
catagttcca gtttctatgg ccttcccacc ttctgttaga aattagtttt atctggcatt    1500
tttaaacatt taaaaattat taaacatttta aaaattagtt tattatcaga tatcagcata    1560
tgcctaataa aacttatttt aataagcatt taattttcca taatatgtta cagccaaggc    1620
ctatataata attttggatt tgttcaatct ttcttacagg ctgttttcta ttgtatcaat    1680
cattagtatc aatcattaag tggaagttga agaaggcatc aaacaaaaca aggatgttta    1740
cagacatatg caaagggtca ggatatctat cctccagtat atagtaatgc ttaataacaa    1800
gtaatcctaa cagcattaaa ggccaaatct gtcctctttc ccctgacttc cttacagcat    1860
gtttatttat attacaagcc attcagggac aaagaaagaa accttgacta ccccactgtc    1920
tactaagaac aaacagcaag caaaattagc aagcaaaatt cactttgaaa gcaccagtgg    1980
ttccattaca ttgacaacta ctaccaagat ttagtagaaa ataagtgctc aacaactaat    2040
ccagattaca gtatgattta gctcatcata attcagatta tttttaatca tcttagccaa    2100
aactgtaaag ttgccacatt actaaagcca cacacatcgt ccctgttttg tagaaatatc    2160
acaaagacca agaggctaca gaaggaggaa atttgcaact gtctttgcaa caataaatca    2220
ggtatctatt ctggtgtaga gataggatgt tgaaagctgc cctgctatca ccagtgtaga    2280
aattaagagt agtacaatac atgtacactg aaatttgcca tcacgtgttt gtgtaaactc    2340
aatgtgcaca ttttgtattt caaaagaaa aataaaagc aaaataaaat gtttataact    2400
ctcaaaaaaa aaaaaaaaa a                                              2421
```

<210> SEQ ID NO 2
<211> LENGTH: 250
<212> TYPE: PRT
<213> ORGANISM: Homo sapiens

<400> SEQUENCE: 2

```
Met Asn Val Arg Arg Val Glu Ser Ile Ser Ala Gln Leu Glu Ala
1               5                   10                  15

Ser Ser Thr Gly Gly Phe Leu Tyr Ala Gln Asn Ser Thr Lys Arg Ser
                20                  25                  30

Ile Lys Glu Arg Leu Met Lys Leu Leu Pro Cys Ser Ala Ala Lys Thr
            35                  40                  45

Ser Ser Pro Ala Ile Gln Asn Ser Val Glu Asp Glu Leu Glu Met Ala
        50                  55                  60

Thr Val Arg His Arg Pro Glu Ala Leu Glu Leu Leu Glu Ala Gln Ser
65                  70                  75                  80

Lys Phe Thr Lys Lys Glu Leu Gln Ile Leu Tyr Arg Gly Phe Lys Asn
                85                  90                  95

Glu Cys Pro Ser Gly Val Val Asn Glu Glu Thr Phe Lys Glu Ile Tyr
            100                 105                 110

Ser Gln Phe Phe Pro Gln Gly Asp Ser Thr Thr Tyr Ala His Phe Leu
        115                 120                 125
```

Phe Asn Ala Phe Asp Thr Asp His Asn Gly Ala Val Ser Phe Glu Asp
            130                 135                 140

Phe Ile Lys Gly Leu Ser Ile Leu Leu Arg Gly Thr Val Gln Glu Lys
145                 150                 155                 160

Leu Asn Trp Ala Phe Asn Leu Tyr Asp Ile Asn Lys Asp Gly Tyr Ile
                165                 170                 175

Thr Lys Glu Glu Met Leu Asp Ile Met Lys Ala Ile Tyr Asp Met Met
            180                 185                 190

Gly Lys Cys Thr Tyr Pro Val Leu Lys Glu Asp Ala Pro Arg Gln His
        195                 200                 205

Val Glu Thr Phe Phe Gln Lys Met Asp Lys Asn Lys Asp Gly Val Val
    210                 215                 220

Thr Ile Asp Glu Phe Ile Glu Ser Cys Gln Lys Asp Glu Asn Ile Met
225                 230                 235                 240

Arg Ser Met Gln Leu Phe Glu Asn Val Ile
                245                 250

<210> SEQ ID NO 3
<211> LENGTH: 750
<212> TYPE: DNA
<213> ORGANISM: Homo sapiens

<400> SEQUENCE: 3

| | | | | |
|---|---|---|---|---|
| atgaatgtga ggagggtgga aagcatttcg gctcagctgg aggaggccag ctctacaggc | 60 |
| ggtttcctgt acgctcagaa cagcaccaag cgcagcatta aagagcggct catgaagctc | 120 |
| ttgccctgct cagctgccaa acgtcgtctc ctgctattca aaacagcgt ggaagatgaa | 180 |
| ctggagatgg ccaccgtcag gcatcggcct gaagcccttg agcttctgga agcccagagc | 240 |
| aaatttacca agaaagagct tcagatcctt tacagaggat ttaagaatga atgccccagt | 300 |
| ggtgttgtta atgaagaaac cttcaaagag atttactcgc agttctttcc acagggagac | 360 |
| tctacaacat atgcacattt tctgttcaat gcatttgata cagaccacaa tggagctgtg | 420 |
| agtttcgagg atttcatcaa aggtctttcc attttgctcc ggggacagt acaagaaaaa | 480 |
| ctcaattggg catttaatct gtatgacata aataaagatg gctacatcac taagaggaa | 540 |
| atgcttgata taatgaaagc aatatacgat atgatgggta atgtacata tcctgtcctc | 600 |
| aaagaagatg ctcccagaca acacgttgaa acatttttc agaaaatgga caaaaataaa | 660 |
| gatggggttg ttaccataga tgagttcatt gaaagctgcc aaaaagatga aacataatg | 720 |
| cgctccatgc agctctttga aaatgtgatt | 750 |

<210> SEQ ID NO 4
<211> LENGTH: 233
<212> TYPE: PRT
<213> ORGANISM: Homo sapiens

<400> SEQUENCE: 4

Ser Thr Gly Gly Phe Leu Tyr Ala Gln Asn Ser Thr Lys Arg Ser Ile
1               5                   10                  15

Lys Glu Arg Leu Met Lys Leu Pro Cys Ser Ala Ala Lys Thr Ser
            20                  25                  30

Ser Pro Ala Ile Gln Asn Ser Val Glu Asp Glu Leu Glu Met Ala Thr

```
                 35                  40                  45
Val Arg His Arg Pro Glu Ala Leu Glu Leu Leu Glu Ala Gln Ser Lys
    50                  55                  60

Phe Thr Lys Lys Glu Leu Gln Ile Leu Tyr Arg Gly Phe Lys Asn Glu
65                  70                  75                  80

Cys Pro Ser Gly Val Val Asn Glu Glu Thr Phe Lys Glu Ile Tyr Ser
                85                  90                  95

Gln Phe Phe Pro Gln Gly Asp Ser Thr Thr Tyr Ala His Phe Leu Phe
                100                 105                 110

Asn Ala Phe Asp Thr Asp His Asn Gly Ala Val Ser Phe Glu Asp Phe
            115                 120                 125

Val Lys Gly Leu Ser Ile Leu Leu Arg Gly Thr Val Gln Glu Lys Leu
    130                 135                 140

Asn Trp Ala Phe Asn Leu Tyr Asp Ile Asn Lys Asp Gly Tyr Ile Thr
145                 150                 155                 160

Lys Glu Glu Met Leu Asp Ile Met Lys Ala Ile Tyr Asp Met Met Gly
                165                 170                 175

Lys Cys Thr Tyr Pro Val Leu Lys Glu Asp Ala Pro Arg Gln His Val
                180                 185                 190

Glu Thr Phe Phe Gln Lys Met Asp Lys Asn Lys Asp Gly Val Val Thr
            195                 200                 205

Ile Asp Glu Phe Ile Glu Ser Cys Gln Lys Asp Glu Asn Ile Met Arg
    210                 215                 220

Ser Met Gln Leu Phe Glu Asn Val Ile
225                 230

<210> SEQ ID NO 5
<211> LENGTH: 727
<212> TYPE: DNA
<213> ORGANISM: Homo sapiens

<400> SEQUENCE: 5
gctctacagg cggtttcctg tacgctcaga acagcaccaa gcgcagcatt aaagagcggc      60
tcatgaagct cttgccctgc tcagctgcca aaacgtcgtc tcctgctatt caaaacagcg     120
tggaagatga actggagatg gccaccgtca ggcatcggcc cgaagccctt gagcttctgg     180
aagcccagag caaatttacc aagaaagagc ttcagatcct ttacagagga tttaagaacg     240
aatgccccag tggtgttgtt aatgaagaaa ccttcaaaga gatttactcg cagttctttc     300
cacagggaga ctctacaaca tatgcacatt ttctgttcaa tgcatttgat acagaccaca     360
atggagctgt gagtttcgag gatttcgtca aggtctttc cattttgctc cggggggacag     420 tacaagaaaa actcaattgg gcatttaatc tgtatgacat aaataaagat ggctacatca     480
ctaaagagga atgcttgat ataatgaaag caatatacga tatgatgggt aaatgtacat     540
atcctgtcct caagaagat gctcccagac aacacgttga acattttt cagaaaatgg     600 acaaaaataa agatggggtt gttaccatag atgagttcat tgaaagctgc caaaagatg     660 aaacataat gcgctccatg cagctctttg aaaatgtgat ttaacttgtc aaatagatcc     720
tgaatcc                                                                727
```

PN7718 NUCLEIC ACIDS AND USE THEREOF

RELATED U.S. APPLICATION

This application claims benefit to U.S. Provisional Application Ser. No. 60/323,613, filed on Sep. 19, 2001, which is incorporated herein by reference in its entirety.

FIELD OF THE INVENTION

The present invention generally relates to novel nucleic acid molecules and proteins, and particularly to an isolated novel cyclophilin C-interacting protein, isolated nucleic acids encoding the protein, and methods of use thereof.

BACKGROUND OF THE INVENTION

While the traditional view of protein function focuses on the action of a single protein molecule, the modern expanded view of protein function defines a protein as an element in an interaction network. See Eisenberg et al., *Nature*, 405: 823–826 (2000). That is, a full understanding of the functions of a protein will require knowledge of not only the characteristics of the protein itself, but also its interactions or connections with other proteins in the same interacting network. In essence, protein—protein interactions form the basis of almost all biological processes, and each biological process is composed of a network of interacting proteins. For example, cellular structures such as the cytoskeleton, nuclear pores, centrosomes, and kinetochores are formed by complex interactions among a multitude of proteins. Many enzymatic reactions are associated with large protein complexes formed by interactions among enzymes, protein substrates, and protein modulators. In addition, protein—protein interactions are also part of the mechanisms for signal transduction and other basic cellular functions, such as DNA replication, transcription, and translation. For example, the complex transcription initiation process generally requires protein—protein interactions among numerous transcription factors, RNA polymerase, and other proteins. See e.g., Tjian and Maniatis, *Cell*, 77:5–8 (1994).

Because most proteins function through their interactions with other proteins, if a test protein interacts with a known protein, one can reasonably predict that the test protein is associated with the functions of the known protein, e.g., in the same cellular structure or same cellular process as the known protein. Thus, interaction partners can provide an immediate and reliable understanding towards the functions of the interacting proteins. By identifying interacting proteins, a better understanding of disease pathways and the cellular processes that result in diseases may be achieved, and important regulators and potential drug targets in disease pathways can be identified.

There has been much interest in protein—protein interactions in the field of proteomics. A number of biochemical approaches have been used to identify interacting proteins. These approaches generally employ the affinities between interacting proteins to isolate proteins in a bound state. Examples of such methods include coimmunoprecipitation and copurification, optionally combined with cross-linking to stabilize the binding. Identities of the isolated protein interacting partners can be characterized by, e.g., mass spectrometry. See e.g., Rout et al., *J. Cell. Biol.*, 148: 635–651 (2000); Houry et al., *Nature*, 402:147–154 (1999); Winter et al., *Curr. Biol.*, 7:517–529 (1997). A popular approach useful in large-scale screening is the phage display method, in which filamentous bacteriophage particles are made by recombinant DNA technologies to express a peptide or protein of interest fused to a capsid or coat protein of the bacteriophage. A whole library of peptides or proteins of interest can be expressed and a bait protein can be used to screen the library to identify peptides or proteins capable of binding to the bait protein. See e.g., U.S. Pat. Nos. 5,223, 409; 5,403,484; 5,571,698; and 5,837,500. Notably, the phage display method only identifies those proteins capable of interacting in an in vitro environment, while the coimmunoprecipitation and copurification methods are not amenable to high throughput screening.

The yeast two-hybrid system is a genetic method that overcomes certain shortcomings of the above approaches. The yeast two-hybrid system has proven to be a powerful method for the discovery of specific protein interactions in vivo. See generally, Bartel and Fields, eds., *The Yeast Two-Hybrid System*, Oxford University Press, New York, N.Y., 1997. The yeast two-hybrid technique is based on the fact that the DNA-binding domain and the transcriptional activation domain of a transcriptional activator contained in different fusion proteins can still activate gene transcription when they are brought into proximity to each other. In a yeast two-hybrid system, two fusion proteins are expressed in yeast cells. One has a DNA-binding domain of a transcriptional activator fused to a test protein. The other includes a transcriptional activating domain of the transcriptional activator fused to another test protein. If the two test proteins interact with each other in vivo, the two domains of the transcriptional activator are brought together reconstituting the transcriptional activator and activating a reporter gene controlled by the transcriptional activator. See, e.g., U.S. Pat. No. 5,283,173.

Because of its simplicity, efficiency and reliability, the yeast two-hybrid system has gained tremendous popularity in many areas of research. In addition, yeast cells are eukaryotic cells. The interactions between mammalian proteins detected in the yeast two-hybrid system typically are bona fide interactions that occur in mammalian cells under physiological conditions. As a matter of fact, numerous mammalian protein—protein interactions have been identified using the yeast two-hybrid system. The identified proteins have contributed significantly to the understanding of many signal transduction pathways and other biological processes. For example, the yeast two-hybrid system has been successfully employed in identifying a large number of novel mammalian cell cycle regulators that are important in complex cell cycle regulations. Using known proteins that are important in cell cycle regulation as baits, other proteins involved in cell cycle control were identified by virtue of their ability to interact with the baits. See generally, Hannon et al., in *The Yeast Two-Hybrid System*, Bartel and Fields, eds., pages 183–196, Oxford University Press, New York, N.Y., 1997. Examples of mammalian cell cycle regulators identified by the yeast two-hybrid system include CDK4/CDK6 inhibitors (e.g., p16, p15, p18 and p19), Rb family members (e.g., p130), Rb phosphatase (e.g., PP1-a2), Rb-binding transcription factors (e.g., E2F-4 and E2F-5), General CDK inhibitors (e.g., p21 and p27), CAK cyclin (e.g., cyclin H), and CDK Thr161 phosphatase (e.g., KAP and CDI1). See id at page 192. "[T]he two-hybrid approach promises to be a useful tool in our ongoing quest for new pieces of the cell cycle puzzle." See id at page 193.

The yeast two-hybrid system can be employed to identify proteins that interact with a specific known protein involved in a disease pathway, and thus provide valuable understandings of the disease mechanism. The identified proteins and the protein—protein interactions in which they participate are potential drug targets for use in identifying new drugs for treating the disease.

SUMMARY OF THE INVENTION

Figure 1:
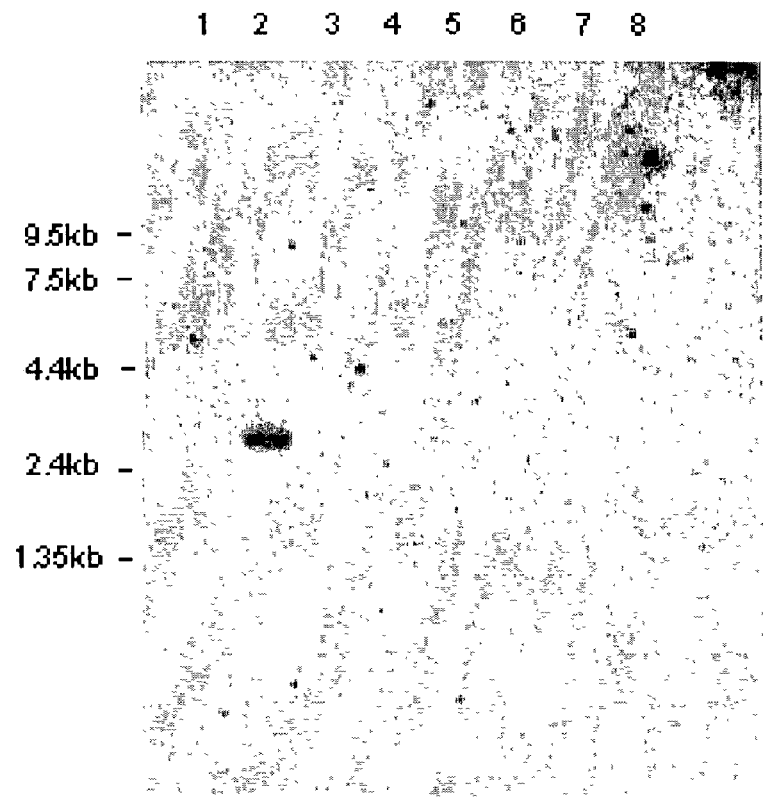
FIG. 1 shows the image of a Northern blot analysis performed using a PN7718 DNA fragment corresponding to nucleotides 177–447 of the sequence of SEQ ID NO:1. The tissues represented are heart, brain, placenta, lung, liver, skeletal muscle, kidney, pancreas, in lanes 1, 2, 3, 4, 5, 6, 7, and 8, respectively.

It has been discovered that cyclophilin C (peptidyl-prolyl isomerase C; PPIC) interacts with PN7718, which is a novel protein. Nucleic acid molecules encoding PN7718 have also been identified. The specific interactions between these proteins suggest that cyclophilin C and PN7718 are involved in common biological processes. In addition, the interactions between cyclophilin C and PN7718 result in the formation of protein complexes both in vitro and in vivo, which contain cyclophilin C and PN7718. The protein complexes formed under physiological conditions can mediate the functions and biological activities of cyclophilin C and PN7718. For example, cyclophilin C, PN7718, and protein complexes containing cyclophilin C and PN7718 are involved in biological processes such as intracellular calcium signaling, beta-amyloid formation, T-cell receptor and IgE receptor signaling pathways, and protein folding and degradation. Thus, the PN7718 nucleic acid and protein molecules are useful in modulating intracellular calcium signaling, beta-amyloid formation, T-cell receptor and IgE receptor signaling pathways, and protein folding and degradation. In addition, the protein complexes as well as PN7718 can be used in screening assays to identify modulators of cyclophilin C, PN7718, and the protein complexes containing them. The identified modulators may be useful in modulating intracellular calcium signaling, beta-amyloid formation, T-cell receptor and IgE receptor signaling pathways, and protein folding and degradation, and in treating or preventing diseases and disorders such as autoimmune diseases, neurological diseases and cardiovascular disorders.

Accordingly, a first aspect of the present invention relates to an isolated PN7718 nucleic acid molecule. Specifically, the present invention provides an isolated nucleic acid molecule having a sequence of SEQ ID NO:1 or SEQ ID NO:3 or a full complement thereof. In another embodiment, an isolated nucleic acid molecule is provided, which has a sequence that is at least 50%, preferably at least 60%, more preferably at least 75%, 80%, 85%, even more preferably at least 90% identical to the sequence of SEQ ID NO:1 or SEQ ID NO:3 or the complement thereof. In addition, the present invention also provides an isolated nucleic acid molecule which can be used to distinguish the PN7718 nucleic acid molecule having the sequence of SEQ ID NO:1 or SEQ ID NO:3 or the complement thereof from a non-PN7718 nucleic acid molecule based on hybridization. In a specific embodiment, the isolated nucleic acid molecule specifically hybridizes to the isolated PN7718 nucleic acid molecule of SEQ ID NO:1 or SEQ ID NO:3 or the complement thereof under stringent conditions. Additionally, the present invention provides nucleic acid molecules having a sequence that is at least 20%, 30%, 40%, 50%, 60%, 70%, 80%, 90%, or 95% identical to the sequence of SEQ ID NO:1 or SEQ ID NO:3 and encode a protein capable of interacting with cyclophilin C. In yet another embodiment, the nucleic acid molecule of the present invention encodes the PN7718 protein having an amino acid sequence of SEQ ID NO:2. The present invention further encompasses nucleic acid molecules encoding a protein having a sequence that is at least 60%, 70% or 75%, preferably at least 80% or 85%, more preferably at least 90%, and even more preferably 95% or more identical to the protein PN7718 sequence of SEQ ID NO:2.

In another embodiment, the present invention provides oligonucleotide molecules or PN7718 nucleic acid fragments having a sequence that is a contiguous span of at least 12, 15, 18, 21, 25, 36, 50, 75, 100, 150, 200, 250, 300, 350, 400 or 500 nucleotides of the sequence of SEQ ID NO:1 or SEQ ID NO:3 or the complement thereof. In addition, the present invention also provides oligonucleotide molecules having at least 12, 15, 18, 20, 25, 30, 35, 50, 75, 100, 150, 200, 250, 300, 350, 400 or 500 nucleotides and capable of hybridizing with a nucleic acid molecule having the sequence of SEQ ID NO:1 or SEQ ID NO:3 or the complement thereof. In a specific embodiment, the oligonucleotide molecules are antisense oligos or ribozymes.

In another embodiment, a hybrid nucleic acid molecule is provided comprising any one of the above-described nucleic acid molecules of the present invention covalently linked to a non-PN7718 nucleic acid. In a specific embodiment, the present invention provides a vector comprising an insert of a PN7718 nucleic acid. Preferably, the vector is a DNA vector. More preferably, the vector is an expression vector useful for the expression of the protein PN7718. In another specific embodiment, the hybrid nucleic acid molecule comprises a PN7718 nucleic acid covalently linked to a cyclophilin C nucleic acid.

The present invention further provides a host cell containing a PN7718 nucleic acid molecule, preferably in a vector contained within the host cell. In addition, the present invention also provides a method for recombinantly producing PN7718, which includes the steps of introducing an expression vector containing a PN7718 nucleic acid molecule into a host cell and expressing PN7718 in that host cell.

In yet another embodiment, the present invention provides a DNA microchip comprising one or more isolated nucleic acid molecules provided in accordance with the present invention.

Additionally, the present invention also provides a kit for detecting PN7718 nucleic acid molecules. The kit may include any of the isolated nucleic acid molecules provided in accordance with the present invention.

In a second aspect of the present invention, an isolated PN7718 polypeptide is provided. In one embodiment, the PN7718 polypeptide comprises a sequence of SEQ ID NO:2. Additionally, the present invention also encompasses a polypeptide having an amino acid sequence that is at least 50%, preferably at least 60%, more preferably at least 75%, 80%, 85%, even more preferably at least 90% identical to the amino acid sequence of SEQ ID NO:2. In a specific embodiment, the homologous polypeptide is a naturally occurring variant of PN7718 identified in a human population. In another embodiment, the present invention also provides an isolated PN7718 polypeptide which is encoded by an isolated nucleic acid molecule that specifically hybridizes to the complement of isolated PN7718 nucleic acid molecule of SEQ ID NO:1 or SEQ ID NO:3 under stringent conditions. In yet another embodiment, the present invention provides an isolated PN7718 polypeptide having a sequence identity of at least 50%, 60%, 70%, 80%, or 90% to the sequence of SEQ ID NO:2 and capable of interacting with cyclophilin C.

The present invention also encompasses a PN7718 polypeptide having a contiguous span of at least 6, 8, 10, 12, 15, 18, 20, 25, 50, 75, 100, 125, 150 or 200 amino acids of the sequence of SEQ ID NO:2. In addition, a polypeptide having a sequence of at least 6, 8, 10, 12, 15, 18, 20, 25, 50, 75, 100, 125, 150 or 200 amino acids is also provided, wherein the sequence is at least 70%, 80%, or 90% homologous to a PN7718 amino acid sequence of the same length. Additionally, the present invention further relates to a hybrid polypeptide having a non-PN7718 polypeptide covalently linked to any one of the above PN7718 polypeptides. In a specific embodiment, the hybrid polypeptide has a cyclophilin C or homologue, derivative or fragment thereof covalently linked to a PN7718 polypeptide. The PN7718 polypeptide or the hybrid polypeptide of the present invention may be incorporated into a protein microchip or microarray.

In accordance with a third aspect of the present invention, isolated protein complexes are provided containing a PN7718 polypeptide. In a specific embodiment, the isolated protein complexes comprise both PN7718 and cyclophilin C. In addition, homologues, derivatives, and fragments of PN7718 and/or of cyclophilin C may also be used in forming protein complexes. In one embodiment, fragments of cyclophilin C and PN7718 corresponding to the protein domains responsible for the interaction between cyclophilin C and PN7718 are used in forming a protein complex of the present invention. In another embodiment, an interacting protein member in the protein complexes of the present invention is a fusion protein containing cyclophilin C or a homologue, derivative, or fragment thereof. A fusion protein containing PN7718 or a homologue, derivative, or fragment thereof may also be used in the protein complexes. In yet another embodiment, a protein complex is provided from a hybrid protein, which comprises cyclophilin C or a homologue, derivative, or fragment thereof covalently linked, directly or through a linker, to PN7718 or a homologue, derivative, or fragment thereof. In addition, nucleic acids encoding the hybrid protein are also encompassed by the present invention.

The present invention also provides a method for making the protein complexes. The method includes the steps of providing the first protein and the second protein in the protein complexes of the present invention and contacting said first protein with said second protein. In addition, the protein complexes can be prepared by isolation or purification from tissues and cells or produced by recombinant expression of their protein members. The protein complexes can be incorporated into a protein microchip or microarray, which are useful in large-scale high throughput screening assays involving the protein complexes.

In accordance with another aspect of the invention, antibodies are provided which are immunoreactive with a PN7718 polypeptide or with a protein complex of the present invention. In one embodiment, the present invention provides an antibody selectively immunoreactive with a PN7718 polypeptide. In another embodiment, an antibody is selectively immunoreactive with a protein complex of the present invention. In yet another embodiment, a bifunctional antibody is provided that has two different antigen binding sites, each being specific to a different interacting protein member in a protein complex of the present invention. The antibodies of the present invention can take various forms including polyclonal antibodies, monoclonal antibodies, chimeric antibodies, antibody fragments such as Fv fragments, single-chain Fv fragments (scFv), Fab' fragments, and F(ab')$_2$ fragments. Preferably, the antibodies are partially or fully humanized antibodies. The antibodies of the present invention can be readily prepared using procedures generally known in the art. For example, recombinant libraries such as phage display libraries and ribosome display libraries may be used to screen for antibodies with desirable specificities. In addition, various mutagenesis techniques such as site-directed mutagenesis and PCR diversification may be used in combination with the screening assays.

The present invention also provides methods for detecting PN7718 nucleic acid, PN7718 polypeptides, and/or a protein complex comprising PN7718. The methods can be used to determine the levels of PN7718 nucleic acid, PN7718 polypeptides, and/or a protein complex comprising PN7718, or detecting aberrations in PN7718 nucleic acid, PN7718 polypeptides, and/or a protein complex comprising PN7718. The detection methods may be useful in the diagnosis of diseases or physiological disorders such as autoimmune diseases, neurological diseases and cardiovascular disorders. In one embodiment, a detection method is provided comprising determining the level of PN7718 nucleic acid, PN7718 polypeptides, and/or a protein complex comprising PN7718 in a sample. In addition, the cellular localization, or tissue or organ distribution of a protein complex of the present invention may be determined to detect any aberrant localization or distribution of the protein complex. In another embodiment, the detection methods comprise detecting mutations in PN7718 or a protein member of a PN7718-containing protein complex. In particular, it is desirable to determine whether the interacting protein members of a PN7718-containing protein complex have any mutations that will lead to, or are associated with, changes in the functional activity of the proteins or changes in their binding affinity to other interacting protein members in forming a protein complex of the present invention. In yet another embodiment, the detection method includes determining the binding constant of the interacting protein members of a PN7718-containing protein complex. A kit may be used for conducting the detection methods of the present invention. Typically, the kit contains reagents useful in any of the above-described embodiments of the detection method, including, e.g., antibodies specific to a PN7718-containing protein complex, PN7718, or other interacting members of the protein complex, and oligonucleotides selectively hybridizable to the cDNAs or mRNAs encoding PN7718 or another interacting protein member of the protein complex.

The present invention also provides screening methods for selecting modulators of PN7718 or a PN7718-containing protein complex. In a specific embodiment, a PN7718-containing protein complex is formed between cyclophilin C or a homologue, derivative or fragment thereof and PN7718 or a homologue, derivative or fragment thereof. The compounds identified in the screening methods of the present invention can be used for modulating the activities of PN7718 and/or of a PN7718-containing protein complex. Such compounds may be useful in modulating intracellular calcium signaling, beta-amyloid formation, T-cell receptor and IgE receptor signaling pathways, and protein folding and degradation and in treating or preventing diseases or disorders such as autoimmune diseases, neurological diseases and cardiovascular disorders.

Thus, test compounds may be screened in an in vitro binding assay to identify compounds capable of binding a PN7718-containing protein complex of the present invention, a PN7718 polypeptide of the present invention, or a mutant or homologue thereof. The assays may include the steps of contacting the protein complex with a test compound and detecting the interaction between the interacting partners. Alternatively, the assays may entail (1) contacting the interacting proteins with each other in the presence of a test compound; and (2) detecting the interaction between the interacting members.

In preferred embodiments, in vivo assays such as yeast two-hybrid assays and various derivatives thereof, preferably reverse two-hybrid assays, are utilized in identifying compounds that interfere with or disrupt protein—protein interactions between cyclophilin C or a homologue, derivative or fragment thereof and PN7718 or a homologue, derivative or fragment thereof. In addition, systems such as yeast two-hybrid assays are also useful in selecting compounds capable of triggering or initiating, enhancing or stabilizing protein—protein interactions between cyclophilin C or a homologue, derivative or fragment thereof and PN7718 or a homologue, derivative or fragment thereof.

In a specific embodiment, the screening method includes: (a) providing in a host cell a first fusion protein having a first protein, which is cyclophilin C or a homologue or derivative or fragment thereof, and a second fusion protein having a second protein, which is PN7718 or a homologue or derivative or fragment thereof, wherein a DNA binding domain is fused to one of the first and second proteins while a transcription-activating domain is fused to the other of said first and second proteins; (b) providing in the host cell a reporter gene, wherein the transcription of the reporter gene is determined by the interaction between the first protein and the second protein; (c) allowing the first and second fusion proteins to interact with each other within the host cell in the presence of a test compound; and (d) determining the presence or absence of expression of the reporter gene.

In addition, the present invention also provides a method for selecting a compound capable of modulating a protein—protein interaction between cyclophilin C and PN7718, which comprises the steps of (1) contacting a test compound with a PN7718 or a homologue or derivative or fragment thereof, and (2) determining whether said test compound is capable of binding said protein. In a preferred embodiment, the method further includes testing a selected test compound capable of binding said protein for its ability to interfere with a protein—protein interaction between cyclophilin C and PN7718, and optionally further testing the selected test compound capable of binding said protein for its ability to modulate cellular activities associated with cyclophilin C and/or PN7718.

The present invention also relates to a virtual screen method for providing a compound capable of modulating an interaction between the interacting members in the protein complexes of the present invention. In one embodiment, the method comprises the steps of providing atomic coordinates defining a three-dimensional structure of a protein complex of the present invention, and designing or selecting compounds capable of interfering with the interaction between said first protein and said second protein based on said atomic coordinates. In another embodiment, the method comprises the steps of providing atomic coordinates defining a three-dimensional structure of cyclophilin C or PN7718 or a fragment thereof, and designing or selecting compounds capable of binding cyclophilin C or PN7718 based on the atomic coordinates. In preferred embodiments, the method further includes testing a selected test compound for its ability to interfere with a protein—protein interaction between cyclophilin C and PN7718, and optionally further testing the selected test compound for its ability to modulate cellular activities associated with cyclophilin C and/or PN7718.

The present invention further provides a composition having two expression vectors. One vector contains a nucleic acid encoding cyclophilin C or a homologue, derivative or fragment thereof. Another vector contains PN7718 or a homologue, derivative or fragment thereof. In addition, an expression vector is also provided containing (1) a first nucleic acid encoding cyclophilin C or a homologue, derivative or fragment thereof; and (2) a second nucleic acid encoding PN7718 or a homologue, derivative or fragment thereof.

Host cells are also provided comprising the expression vector(s). In addition, the present invention also provides a host cell having two expression cassettes. One expression cassette includes a promoter operably linked to a nucleic acid encoding cyclophilin C or a homologue, derivative or fragment thereof. Another expression cassette includes a promoter operably linked to a nucleic acid encoding PN7718 or a homologue, derivative or fragment thereof. Preferably, the expression cassettes are chimeric expression cassettes with heterologous promoters included.

In specific embodiments of the host cells or expression vectors, one of the two nucleic acids is linked to a nucleic acid encoding a DNA binding domain, and the other is linked to a nucleic acid encoding a transcription-activation domain, whereby two fusion proteins can be encoded.

In accordance with yet another aspect of the present invention, methods are provided for modulating the activities of a PN7718 polypeptide or a PN7718-containing protein complex. The methods may be useful in modulating intracellular calcium signaling, beta-amyloid formation, T-cell receptor and IgE receptor signaling pathways, and protein folding and degradation and in treating or preventing diseases and disorders such as autoimmune diseases, neurological diseases and cardiovascular disorders. In one embodiment, the methods comprise reducing a PN7718-containing protein complex level and/or inhibiting the activities of the protein complex. Alternatively, the level and/or activity of PN7718 or its interacting protein partners such as cyclophilin C may be inhibited. Thus, the methods may include administering to a cell or a patient an antibody specific to a PN7718-containing protein complex, PN7718 or a PN7718-interacting protein. The methods may also include the administration to a cell or a patient an antisense oligo or ribozyme selectively hybridizable to a gene or mRNA encoding PN7718 or a PN7718-interacting protein. In addition, a compound identified in a screening assay of the present invention may also be used in the methods. Also, a PN7718 fragment capable of binding cyclophilin C can be employed as a competitive inhibitor of PN7718 and/or cyclophilin C. Gene therapy methods may also be used in reducing the expression of the gene encoding cyclophilin C or PN7718.

In another embodiment, the methods for modulating the activities of a PN7718 polypeptide or a PN7718-containing protein complex comprise increasing the protein complex level and/or activating the activities of the protein complex. Alternatively, the level and/or activity of PN7718 or a PN7718-interacting protein may be increased. Thus, a particular PN7718-containing protein complex or cyclophilin C or PN7718 of the present invention may be administered directly to a cell or a patient. Or, exogenous genes encoding one or more protein members of a PN7718-containing protein complex may also be introduced into a cell by standard molecular biology techniques or to a patient by gene therapy approaches. In addition, cells in vitro or in a patient needing treatment or prevention may also be in contact with compounds identified in a screening assay of the present invention capable of binding PN7718 or an interacting protein thereof, or triggering or initiating, enhancing or stabilizing protein—protein interactions between PN7718 or a homologue, derivative or fragment thereof and a PN7718-interacting protein such as cyclophilin C.

The foregoing and other advantages and features of the invention, and the manner in which the same are accomplished, will become more readily apparent upon consideration of the following detailed description of the invention taken in conjunction with the accompanying examples, which illustrate preferred and exemplary embodiments.

DETAILED DESCRIPTION OF THE INVENTION

1. Definitions

The terms "polypeptide," "protein," and "peptide" are used herein interchangeably to refer to amino acid chains in which the amino acid residues are linked by peptide bonds or modified peptide bonds. The amino acid chains can be of any length of greater than two amino acids. Unless otherwise specified, the terms "polypeptide," "protein," and "peptide" also encompass various modified forms thereof. Such modified forms may be naturally occurring modified forms or chemically modified forms. Examples of modified forms include, but are not limited to, glycosylated forms, phosphorylated forms, myristoylated forms, palmitoylated forms, ribosylated forms, acetylated forms, etc. Modifications also include intra-molecular crosslinking and covalent attachment to various moieties such as lipids, flavin, biotin, polyethylene glycol or derivatives thereof, etc. In addition, modifications may also include cyclization, branching and cross-linking. Further, amino acids other than the conventional twenty amino acids encoded by genes may also be included in a polypeptide.

The term "isolated" when used in reference to nucleic acids (which include gene sequences) of this invention is intended to mean that a nucleic acid molecule is present in a form other than that found in nature in its original environment with respect to its association with other molecules. For example, since a naturally existing chromosome includes a long nucleic acid sequence, an "isolated nucleic acid" as used herein means a nucleic acid molecule having only a portion of the nucleic acid sequence in the chromosome but not one or more other portions present on the same chromosome. Thus, for example, an isolated nucleic acid typically includes no more than 5 kb, preferably no more than 2.5 kb, more preferably no more than 1 kb naturally occurring nucleic acid sequence that immediately flanks the gene in the naturally existing chromosome or genomic DNA. However, it is noted that an "isolated nucleic acid" as used herein is distinct from a clone in a conventional library such as a genomic DNA library or a cDNA library in that the clones in a library are still in admixture with almost all the other nucleic acids in a chromosome or a cell. An isolated nucleic acid can be in a vector. An isolated nucleic acid can also be part of a composition so long as the composition is substantially different from the nucleic acid's original natural environment. In this respect, an isolated nucleic acid can be in a semi-purified state, i.e., in a composition having certain natural cellular components, while it is substantially separated from other naturally occurring nucleic acids and can be readily detected and/or assayed by standard molecular biology techniques. Preferably, an "isolated nucleic acid" is separated from at least 50%, more preferably at least 75%, and most preferably at least 90% of other naturally occurring nucleic acids.

The term "isolated nucleic acid" encompasses the term "purified nucleic acid," which means a specified nucleic acid is in a substantially homogenous preparation of nucleic acid substantially free of other cellular components, other nucleic acids, viral materials, or culture medium, or chemical precursors or by-products associated with chemical reactions for chemical synthesis of nucleic acids. Typically, a "purified nucleic acid" can be obtained by standard nucleic acid purification methods. In a purified nucleic acid, preferably the specified nucleic acid molecule constitutes at least 75%, preferably at least 85, and more preferably at least 95 percent of the total nucleic acids in the preparation. The term "purified nucleic acid" also means nucleic acids prepared from a recombinant host cell (in which the nucleic acids have been recombinantly amplified and/or expressed) or chemically synthesized nucleic acids.

The term "isolated nucleic acid" also encompasses "recombinant nucleic acid" which is used herein to mean a hybrid nucleic acid produced by recombinant DNA technology having the specified nucleic acid molecule covalently linked to one or more nucleic acid molecules that are not the nucleic acids naturally flanking the specified nucleic acid in the naturally existing chromosome. Typically, such one or more nucleic acid molecules flanking the specified nucleic acid are no more than 50 kb, preferably no more than 25 kb.

The term "stringent hybridization conditions," when used in connection with nucleic acid hybridization, means hybridization conducted overnight at 42 degrees C. in a solution containing 50% formamide, 5×SSC (750 mM NaCl, 75 mM sodium citrate), 50 mM sodium phosphate, pH 7.6, 5× Denhardt's solution, 10% dextran sulfate, and 20 microgram/ml denatured and sheared salmon sperm DNA, with hybridization filters washed in 0.1×SSC at about 65° C. It is noted that many other hybridization methods, solutions and temperatures can be used to achieve comparable stringent hybridization conditions as will be apparent to skilled artisans.

The term "isolated polypeptide" as used herein is defined as a polypeptide molecule that is present in a form other than that found in nature in its original environment with respect to its association with other molecules. Typically, an "isolated polypeptide" is separated from at least 50%, more preferably at least 75%, most preferably at least 90% of other naturally co-existing polypeptides in a cell or organism.

The term "isolated polypeptide" encompasses a "purified polypeptide" which is used herein to mean a specified polypeptide is in a substantially homogenous preparation substantially free of other cellular components, other polypeptides, viral materials, or culture medium, or when the polypeptide is chemically synthesized, chemical precursors or by-products associated with the chemical synthesis. Preferably, in a purified polypeptide, preferably the specified polypeptide molecule constitutes at least 75%, preferably at least 85%, and more preferably at least 95% of the total polypeptide in the preparation. A "purified polypeptide" can be obtained from natural or recombinant host cells by standard purification techniques, or by chemically synthesis.

The term "isolated polypeptide" also encompasses a "recombinant polypeptide," which is used herein to mean a hybrid polypeptide produced by recombinant DNA technology or chemical synthesis having a specified polypeptide covalently linked to one or more polypeptide molecules, which do not naturally flank the specified polypeptide.

The terms "hybrid protein," "hybrid polypeptide," "hybrid peptide," "fusion protein," "fusion polypeptide," and "fusion peptide" are used herein interchangeably to mean a non-naturally occurring protein having a specified polypeptide molecule covalently linked to one or more polypeptide molecules, which do not naturally link to the specified polypeptide. Thus, a "hybrid protein" may be two naturally occurring proteins or fragments thereof linked together by a covalent linkage. A "hybrid protein" may also be a protein formed by covalently linking two artificial polypeptides together. Typically but not necessarily, the two or more polypeptide molecules are linked or "fused" together by a peptide bond forming a single non-branched polypeptide chain.

As used herein, the term "homologue," when used in connection with a first native protein or fragment thereof that is discovered, according to the present invention, to interact with a second native protein or fragment thereof, means a polypeptide that exhibits an amino acid sequence homology and/or structural resemblance to the first native interacting protein, or to one of the interacting domains of the first native protein such that it is capable of interacting with the second native protein. Typically, a protein homologue of a native protein may have an amino acid sequence that is at least 50%, preferably at least 75%, more preferably at least 80%, 85%, 86%, 87%, 88% or 89%, even more preferably at least 90%, 91%, 92%, 93% or 94%, and most preferably 95%, 96%, 97%, 98% or 99% identical to the native protein. Examples of homologues may be the ortholog proteins of other species including animals, plants, yeast, bacteria, and the like. Homologues may also be selected by, e.g., mutagenesis in a native protein. For example, homologues may be identified by site-specific mutagenesis in combination with assays for detecting protein—protein interactions, e.g., the yeast two-hybrid system described below, as will be apparent to skilled artisans apprised of the present invention. Other techniques for detecting protein—protein interactions include, e.g., protein affinity chromatography, affinity blotting, in vitro binding assays, and the like.

The term "derivative," when used in connection with a first native protein (or fragment thereof) that is discovered, according to the present invention, to interact with a second native protein (or fragment thereof), means a modified form of the first native protein prepared by modifying the side chain groups of the first native protein without changing the amino acid sequence of the first native protein. The modified form, i.e., the derivative should be capable of interacting with the second native protein. Examples of modified forms include glycosylated forms, phosphorylated forms, myristylated forms, ribosylated forms, ubiquitinated forms, and the like. Derivatives also include hybrid or fusion proteins containing a native protein or a fragment thereof. Methods for preparing such derivative forms should be apparent to skilled artisans. The prepared derivatives can be easily tested for their ability to interact with the native interacting partner using techniques known in the art, e.g., protein affinity chromatography, affinity blotting, in vitro binding assays, yeast two-hybrid assays, and the like.

For purposes of comparing two different nucleic acid or polypeptide sequences, one sequence (comparing sequence) may be described to be a specific "percent identical to" another sequence (reference sequence) in the present disclosure. In this respect, the percentage identity is determined by the algorithm of Karlin and Altschul, *Proc. Natl. Acad. Sci. USA*, 90:5873–5877 (1993), which is incorporated into the various BLAST programs. Specifically, the percentage identity is determined by the "BLAST 2 Sequences" tool. See Tatusova and Madden, *FEMS Microbiol. Lett.*, 174(2): 247–250 (1999). For pairwise DNA—DNA comparison, the BLASTN 2.1.2 program is used with default parameters (Match: 1; Mismatch: −2; Open gap: 5 penalties; extension gap: 2 penalties; gap x_dropoff: 50; expect: 10; and word size: 11, with filter). For pairwise protein—protein sequence comparison, the BLASTP 2.1.2 program is employed using default parameters (Matrix: BLOSUM62; gap open: 11; gap extension: 1; x_dropoff: 15; expect: 10.0; and wordsize: 3, with filter).

As used herein, the term "protein complex" means a composite unit that is a combination of two or more proteins formed by interaction between the proteins. Typically but not necessarily, a "protein complex" is formed by the binding of two or more proteins together through specific non-covalent binding affinities. However, covalent bonds may also be present between the interacting partners. For instance, the two interacting partners can be covalently crosslinked so that the protein complex becomes more stable.

The term "isolated protein complex" means a protein complex present in a composition or environment that is different from that found in nature in its native or original cellular or biological environment. Preferably, an "isolated protein complex" is separated from at least 50%, more preferably at least 75%, and most preferably at least 90% of other naturally co-existing cellular or tissue components. Thus, an "isolated protein complex" may also be a naturally existing protein complex in an artificial preparation. An "isolated protein complex" may also be a protein complex that is not found in nature. An "isolated protein complex" may also be a "purified protein complex," that is, a substantially purified form in a substantially homogenous preparation substantially free of other cellular components, other polypeptides, viral materials, or culture medium, or when the protein components in the protein complex are chemically synthesized, substantially free of chemical precursors or by-products associated with the chemical synthesis. A "purified protein complex" typically means a preparation containing preferably at least 75%, more preferably at least 85%, and most preferably at least 95% a particular protein complex. A "purified protein complex" may be obtained from natural or recombinant host cells or other body samples by standard purification techniques, or by chemical synthesis.

As used herein, the term "interacting" or "interaction" means that two protein domains or complete proteins exhibit sufficient physical affinity to each other so as to bring the two "interacting" protein domains or proteins physically close to each other. An extreme case of interaction is the formation of a chemical bond that results in continual and stable proximity of the two domains or proteins. Interactions that are based solely on physical affinities, although usually more dynamic than chemically bonded interactions, can be equally effective in co-localizing two proteins. Examples of physical affinities and chemical bonds include but are not limited to, forces caused by electrical charge differences, hydrophobicity, hydrogen bonds, Van der Waals force, ionic force, covalent linkages, and combinations thereof. The state of proximity between the interacting domains or entities may be transient or permanent, reversible or irreversible. In any event, it is in contrast to and distinguishable from contact caused by natural random movement of two entities. Typically although not necessarily, an "interaction" is exhibited by the binding between the interacting domains or entities. Examples of interactions include specific interactions between antigen and antibody, ligand and receptor, enzyme and substrate, and the like.

An "interaction" between two protein domains or complete proteins can be determined by a number of methods. For example, an interaction can be determined by functional assays such as the two-hybrid systems. Protein—protein interactions can also be determined by various biochemical approaches based on the affinity binding between two interacting partners. Such biochemical methods generally known in the art include, but are not limited to, protein affinity chromatography, affinity blotting, immunoprecipitation, and the like. The binding constant for two interacting proteins, which reflects the strength or quality of the interaction, can also be determined using methods known in the art. See Phizicky and Fields, *Microbiol. Rev.*, 59:94–123 (1995).

The term "antibody" as used herein encompasses both monoclonal and polyclonal antibodies that fall within any antibody classes, e.g., IgG, IgM, IgA, or derivatives thereof. The term "antibody" also includes antibody fragments including, but not limited to, Fab, F(ab')$_2$, and conjugates of such fragments, and single-chain antibodies comprising an antigen recognition epitope. In addition, the term "antibody" also means humanized antibodies, including partially or fully humanized antibodies. An antibody may be obtained from an animal, or from a hybridoma cell line producing a monoclonal antibody, or obtained from cells or libraries recombinantly expressing a gene encoding a particular antibody.

The term "immunoreactive with" as used herein means that an antibody is reactive with and thus is capable of binding to a specific protein or protein complex with a sufficient specificity as demonstrated in a typical immunoassay.

The term "selectively immunoreactive" as used herein means that an antibody is reactive thus binds to a specific protein or protein complex, but not other similar proteins or fragments or components thereof.

The term "activity" when used in connection with proteins or protein complexes means any physiological or biochemical activities displayed by or associated with a particular protein or protein complex including but not limited to activities exhibited in biological processes and cellular functions, ability to interact with or bind another molecule or a moiety thereof, binding affinity or specificity to certain molecules, in vitro or in vivo stability (e.g., protein degradation rate, or in the case of protein complexes, the ability to maintain the form of a protein complex), antigenicity and immunogenecity, enzymatic activities, etc. Such activities may be detected or assayed by any of a variety of suitable methods as will be apparent to skilled artisans.

The term "compound" as used herein encompasses all types of organic or inorganic molecules, including but not limited proteins, peptides, polysaccharides, lipids, nucleic acids, small organic molecules, inorganic compounds, and derivatives thereof.

As used herein, the term "interaction antagonist" means a compound that interferes with, blocks, disrupts, or destabilizes a protein—protein interaction; blocks or interferes with the formation of a protein complex; or destabilizes, disrupts or dissociates an existing protein complex.

The term "interaction agonist" as used herein means a compound that triggers, initiates, propagates, nucleates, or otherwise enhances the formation of a protein—protein interaction; triggers, initiates, propagates, nucleates, or otherwise enhances the formation of a protein complex; or stabilizes an existing protein complex.

Unless otherwise specified, the term "cyclophilin C" as used herein means the human cyclophilin C protein. Likewise, "PN7718" means the human PN7718 protein unless otherwise specified in the present disclosure.

2. Novel PN7718 Nucleic Acids

The present invention is based on the discovery of a novel human protein PN7718. In particular, it has been discovered in a yeast two-hybrid assay that PN7718 specifically interacts with cyclophilin C. The domains or fragments capable of conferring interacting properties on cyclophilin C and PN7718 have also been identified, which are summarized in Table 1. The nucleotide sequence of a naturally occurring nucleic acid encoding PN7718 has been deciphered and provided in SEQ ID NO:1. The portion of SEQ ID NO:1 corresponding to the full open reading frame is provided in SEQ ID NO:3. In addition, the amino acid sequence of the PN7718 protein deduced from the nucleotide sequence of SEQ ID NO:1 is provided in SEQ ID NO:2. XX SEQ ID NO:4 shows the amino acid sequence of a fragment of PN7718 protein. The fragment was identified as being capable of interacting with cyclophilin C. In addition, SEQ ID NO:5 is a naturally occurring nucleotide sequence encoding the PN7718 fragment of SEQ ID NO:4.

TABLE 1

Interaction between PN7718 and CYPC

| Bait Protein | | Prey Protein | | | | Identifiable Motif | |
| --- | --- | --- | --- | --- | --- | --- | --- |
| | Bait AA Sequence | Prey Protein | Prey AA Sequence | Prey NT Sequence | Motif | | AA Coordinate |
| cyclophilin C (CYPC) (GB:S71018) | 1–212 | PN7718 | 18–250* | 224–950 | EF-hand, calcium binding motif EF_HAND_2 Eps15 | | 124–152 160–188 208–236 158–233 78–149 113–213 |

The novel protein PN7718 was identified as an interactor of cyclophilin C. Cyclophilins catalyze the cis-trans isomerization of peptidyl-prolyl bonds, which is critical step in protein folding. In addition, it is known that members of the cyclophilin family bind the immunosuppressive drug cyclosporin A (CsA) and act as mediators of the immunosuppressive and nephrotoxic actions of cyclosporin A. Specifically, Liu et al., *Cell*, 66:807–815 (1991) showed that cyclophilin-CsA complexes (but not cyclophilin alone) competitively bind to and inhibit the $Ca^{2+}$- and calmodulin-dependent phophatase calcineurin. Thus, it has been suggested that calcineurin is involved in a common step associated with T-cell receptor and IgE receptor signaling pathways and that cyclophilins mediate the immunosuppresive effect of cyclosporin A by altering the activity of calcineurin-calmodulin. Liu et al., *Cell*, 66:807–815 (1991).

Interestingly, PN7718 is similar to calsenilin, a presenilin binding protein which inhibits transcription of prodynorphin and contains EF hand domains that mediate binding to calcium. See Buxbaum et al., *Nat. Med.*, 4 (10), 1177–1181 (1998); see also GenBank Accession No. AF120102. At the nucleotide level, the 3' half of the PN7718 cDNA sequence is about 78% identical to that calsenilin, and the corresponding amino acid sequences are about 79% identical and about 91% similar. The overall protein sequence identity is about 64%. Calsenilin was identified in yeast 2-hybrid system as an interactor of the C-terminal of presenilin-2. See id. Indeed, calsenilin interacts with both presenilin-1 and presenilin-2 and regulates the levels of a proteolytic product of presenilin-2. It is known most early-onset familial Alzheimer disease (FAD) cases are caused by mutations in presenilin 1 and presenilin 2. Presenilin mutations result in increases in beta-amyloid formation and apoptosis in many experimental systems. See Buxbaum et al., *Nat. Med.*, 4 (10), 1177–1181 (1998). Notably, FAD presenilin mutations also lead to highly specific and selective alterations in intracellular calcium signaling. Specifically, mutant presenilin 1 potentiates the amplitude of calcium signals evoked by inositol 1,4,5-triphophate and accelerates their rates of decay in *Xenopus* oocytes. See Leissring et al., *Proc. Natl. Acad. Sci. USA*, 97:8590–3 (2000). However, co-expression of calsenilin reverses both of the effects.

Northern analysis showed specific expression of PN7718 transcript in brain. The involvement of calsenilin in calcium signaling, the participation of calcium-dependent calcineurin in cyclophilin's action in mediating immunosuppresion, the sequence similarity between PN7718 and calsenilin combined with the discovery that PN7718 specifically interacts with cyclophilin C all suggest that PN7718 and cyclophilin C are involved in common biological processes and pathological pathways. For example, PN7718 may be involved in intracellular calcium signaling, T-cell receptor and IgE receptor signaling pathways, and protein folding and degradation. As such, PN7718 as well as the interaction between cyclophilin C and PN7718 can be attractive targets for developing drugs against neurological diseases and autoimmune diseases.

Furthermore, it has recently been discovered that PN7718 is identical to the calsenilin-like protein (CALP) and potassium channel-interacting protein 4 (KchIP4). See Morohashi et al., *J. Biol. Chem.*, 277(17): 14965–14975 (2002); see also Holmqvist et al., *Proc. Natl. Acad. Sci. U.S.A.*, 99(2): 1035–1040 (2002). PN7718/CALP/KchIP4 interacts with presenilin-2, and the calsenilin fragment that interacts with the preseninlins is almost identical to the corresponding fragment of PN7718/CALP/KChIP4. See Morohashi et al., *J. Biol. Chem.*, 277(17):14965–14975 (2002). It is very likely that PN7718/CALP/KChIP4 binds to both presenilin-1 and presenilin-2.

The interaction between cyclophilin C and PN7718 suggests that these two proteins may be involved in common biological processes and disease pathways. For example, they may play a role in cellular functions such as intracellular calcium signaling, T-cell receptor and IgE receptor signaling pathways, and protein folding and degradation, and in disease pathways for diseases and disorders such as autoimmune diseases, neurological diseases and cardiovascular disorders. The protein complexes formed by cyclophilin C and PN7718 or a homologue thereof may be potential targets for developing drugs useful in treating the diseases and disorders.

Accordingly, the present invention provides isolated PN7718 nucleic acid molecules. The nucleic acid molecules can be in the form of DNA, RNA, or a chimeric or hybrid thereof, and can be in any physical structures including single-stranded or double-stranded molecules, or in the form of a triple helix. In one embodiment, the isolated PN7718 nucleic acid molecule has a sequence of SEQ ID NO:1 or SEQ ID NO:3 or the complement thereof. Conveniently, by way of examples, the isolated PN7718 nucleic acid molecule in accordance with this embodiment can be prepared by isolating the PN7718 mRNA from human cells or tissues, or by reverse transcribing a PN7718 mRNA molecule and amplifying the synthesized cDNA molecule.

In addition, nucleic acid molecules are also contemplated which are capable of specifically hybridizing, under stringent hybridization conditions, to a nucleic acid molecule having the sequence of SEQ ID NO:1 or SEQ ID NO:3 or the complement thereof. Preferably, such nucleic acid molecules encode a polypeptide having the sequence of SEQ ID NO:2.

In another embodiment, an isolated nucleic acid molecule is provided which has a sequence that is at least 50%, preferably at least 60%, more preferably at least 75%, 80%, 82%, 85%, even more preferably at least 90%, 91%, 92%, 93%, 94%, 95%, 96%, 97%, 98%, or 99% identical to the sequence of SEQ ID NO:1 or SEQ ID NO:3 or the complement thereof. Preferably, such nucleic acid molecules encode a polypeptide having the sequence of SEQ ID NO:2.

As is apparent to skilled artisans, the homologous nucleic acids or the nucleic acids capable of hybridizing with a nucleic acid of the sequence of SEQ ID NO:1 or SEQ ID NO:3 can be prepared by manipulating a PN7718 nucleic acid molecule having a sequence of SEQ ID NO:1 or SEQ ID NO:3. For example, various nucleotide substitutions, deletions or insertions can be incorporated into the PN7718 nucleic acid molecule by standard molecular biology techniques. As will be apparent to skilled artisans, such nucleic acids are useful irrespective of whether they encode a functional PN7718 protein. For example, they can be used as probes for isolating and/or detecting PN7718 nucleic acids. Nevertheless, preferably the homologous nucleic acids or the nucleic acids capable of hybridizing with a nucleic acid of the sequence of SEQ ID NO:1 or SEQ ID NO:3 encode a polypeptide having one or more PN7718 activities. In a specific embodiment, the proteins encoded by the nucleic acids are capable of interacting with cyclophilin C. In another specific embodiment, the isolated nucleic acid molecules are naturally occurring allelic variants of the PN7718 gene nucleic acid.

In addition, nucleic acid molecules that encode the PN7718 protein having an amino acid sequence of SEQ ID NO:2 are also intended to fall within the scope of the present invention. As will be immediately apparent to a skilled artisan, due to genetic code degeneracy, such nucleic acid molecules can be designed conveniently by nucleotide substitutions in the wild-type PN7718 nucleotide sequence of SEQ ID NO:1 or SEQ ID NO:3.

In addition, the present invention further encompasses nucleic acid molecules encoding a protein that has a sequence that is at least 75%, preferably at least 85%, 90%, 91%, 92%, 93%, or 94%, and more preferably at least 95%, 96%, 97%, 98%, or 99% identical to the sequence of SEQ ID NO:2. Preferably, the homologous protein retains one or more activities of PN7718. More preferably, the homologous protein is capable of interacting with cyclophilin C. The ability to interact with cyclophilin C can be tested or demonstrated by various methods as described below in Sections 4 and 10, e.g., in a yeast two hybrid system. The various nucleic acid molecules may be provided by chemical synthesis and/or recombinant techniques based on an isolated PN7718 nucleic acid molecule having a sequence of SEQ ID NO:1 or SEQ ID NO:3.

In another embodiment of the present invention, oligonucleotides or PN7718 fragments are provided having a contiguous span of at least 10, 12, 15, 16, 17, 18, 19, 20, 21, 22, 23, 24, 25, 26, 27, 28, 29, 30, 35, 50, 75, 100, 125, 150, 200, 250, 300, 350 or 400 nucleotides of the sequence of SEQ ID NO:1 or SEQ ID NO:3 or the complement thereof. Preferably, the oligonucleotides are less than the full length of the sequence of SEQ ID NO:1 or SEQ ID NO:3, more preferably no greater than 1,200, 1,000, 800, 600, 400, 200, 100, or 50 nucleotides in length. In a preferred embodiment, the oligonucleotides have a length of about 12–18, 19–25, 26–34, 35–50, or 51–100 nucleotides. In a specific embodiment, the oligonucleotide is a sequence encoding a contiguous span of at least 4, 5, 6, 7, 8, 9, 10, 11, 12, 13, 14, 15, 17, 20, 22, 25, 30, 35, 50, 75, 100, 125 or 150 amino acids of SEQ ID NO:2. More specifically, a peptide having this contiguous span of amino acid sequence is capable of interacting with cyclophilin C. In yet another specific embodiment, the oligonucleotide is an antisense oligo as described in Section 11.2.2. In another specific embodiment, the oligonucleotide is a ribozyme molecule as described in Section 11.2.3.

The present invention further encompasses oligonucleotides that have a length of at least 10, 12, 15, 17, 18, 19, 20, 21, 22, 23, 24, 25, 30, 35, 50, 75, 100, 125, 150, 200, 250, 300, 350 or 400 nucleotides and preferably no greater than 1,200, 1,000, 800, 600, 400, 200, 100, or 50 nucleotides, and are at least 85%, 90%, 92% or 94%, and more preferably at least 95%, 96%, 97%, 98%, or 99% identical to a contiguous span of nucleotides of the sequence of SEQ ID NO:1 or SEQ ID NO:3 or the complement thereof of the same length. The oligonucleotides can have a length of about 12–18, 19–25, 26–34, 35–50, or 51–100 nucleotides. In a preferred embodiment, the oligonucleotides have a length of about 12–100, 15–75, 17–50, 21–50, or preferably 25–50 nucleotides. Preferably, the oligonucleotide is a sequence encoding a contiguous span of at least 4, 5, 6, 7, 8, 9, 10, 11, 12, 13, 14, 15, 17, 20, 22, 25, 30, 35, 50, 75, 100, 125 or 150 amino acids of SEQ ID NO:2. More preferably, a peptide having this contiguous span of amino acid sequence is capable of interacting with cyclophilin C.

In addition, oligonucleotides are also contemplated having a length of at least 10, 12, 15, 17, 18, 19, 20, 21, 22, 23, 24, 25, 30, 35, 50, 75, 100, 125, 150, 200, 250, 300, 350 or 400 nucleotides and preferably no greater than 1,200, 1,000, 800, 600, 400, 200, 100, or 50 nucleotides, and capable of hybridizing to the nucleotide sequence of SEQ ID NO:1 or SEQ ID NO:3 or the complement thereof under stringent hybridization conditions. In a preferred embodiment, the oligonucleotides have a length of about 12–100, 15–75, 17–50, 21–50, or preferably 25–50 nucleotides. In another preferred embodiment, the oligonucleotides capable of hybridizing to the nucleotide sequence of SEQ ID NO:1 or SEQ ID NO:3 or the complement thereof encodes a contiguous span of at least 7, 8, 9, 10, 11, 12, 13, 14, 15, 16, 17, 18, 19, 20, 25, 30, 35, 50, 75, 100, 125 or 150 amino acids of SEQ ID NO:2. More preferably, a peptide having this contiguous span of amino acids is capable of interacting with cyclophilin C.

As will be apparent to skilled artisans, the various oligonucleotides of the present invention are useful as probes for detecting PN7718 nucleic acids in cells and tissues. They can also be used as primers for procedures including the amplification of PN7718 nucleic acids or homologues thereof, sequencing PN7718 nucleic acids, and detection of mutations in PN7718 nucleic acids or homologues thereof. In addition, the oligonucleotides may be used to encode a fragment, epitope or domain of PN7718 or a homologue thereof, which is useful in a variety of applications including use as antigenic epitopes for preparing antibodies against PN7718.

It should be understood that the nucleic acid molecules of the present invention may be in standard forms with conventional nucleotide bases and backbones, but can also be in various modified forms, e.g., having therein modified nucleotide bases or backbones. Examples of modified nucleotide bases or backbones described in Section 11.2.2 in the context of modified antisense compounds should be equally applicable in this respect.

In another embodiment, a hybrid nucleic acid molecule is provided comprising any one of the above-described nucleic acid molecules of the present invention covalently linked to a non-PN7718 nucleic acid. In a specific embodiment, the present invention provides a vector comprising an insert of a PN7718 nucleic acid. Preferably, the vector is a DNA vector comprising as an insert any one of the above-described nucleic acid molecules of the present invention. In a specific embodiment, the vector is an expression vector. Any suitable vectors may be used for purposes of the present invention. Expression vectors described in detail in Sections 4 and 6 may be applicable in this respect as will be apparent to skilled artisans. The vectors of the present invention may be used to amplify the nucleic acid molecules of the present invention, or to introduce the nucleic acids into host cells, or for purposes of producing proteins encoded by the nucleic acids in a cell free system or in cells or tissues.

Thus, the present invention further contemplates host cells into which any of the nucleic acid molecules of the present invention have been introduced from an exogenous source. The nucleic acid molecules of the present invention may be introduced into any type of suitable host cells, including, but not limited to, bacteria, yeast cells, plant cells, insect cells, and animal cells. The nucleic acid molecules of the present invention can be introduced exogenously into a host cell by any methods known in the art, including those described in detail in Sections 6 and 11.3.2 below. When a nucleic acid molecule of the present invention is appropriately incorporated into a suitable expression vector and introduced into host cells, proteins may be recombinantly expressed within the host cells. Accordingly, the present invention also provides methods for recombinantly producing PN7718 which includes the steps of introducing an expression vector containing a PN7718 nucleic acid molecule into a cell and expressing PN7718 in the host cell. The thus expressed proteins may be isolated and/or purified by standard purification techniques known in the art. Methods for making the host cells and recombinantly expressing PN7718 will be apparent to skilled artisans especially in view of the disclosure in Sections 6 and 11.3.2.

In yet another embodiment of the present invention, a nucleic acid microchip or microarray is provided comprising one or more of the foregoing isolated nucleic acid molecules of the present invention. As is known in the art, with nucleic acid microchips a large number of nucleic acid molecules can be attached or immobilized in an array on a solid support, e.g., a silicon chip or glass slide. See Lipshutz et al., *Biotechniques*, 19:442–447 (1995); Chee et al., *Science*, 274:610–614 (1996); Kozal et al., *Nat. Med.* 2:753–759 (1996); Hacia et al., *Nat. Genet.*, 14:441–447 (1996); Saiki et al., *Proc. Natl. Acad. Sci. USA*, 86:6230–6234 (1989); Gingeras et al., *Genome Res.*, 8:435–448 (1998). The microchip technologies combined with computerized analysis tools allow speedy high throughput screening and analysis. Various techniques for making and using nucleic acid microchips are known in the art and disclosed in, e.g., U.S. Pat. No. 5,925,525 to Fodor et al; Wilgenbus et al., *J. Mol. Med.*, 77:761–786 (1999); Graber et al., *Curr. Opin. Biotechnol.*, 9:14–18 (1998); Hacia et al., *Nat. Genet.*, 14:441–447 (1996); Shoemaker et al., *Nat. Genet.*, 14:450–456 (1996); DeRisi et al., *Nat. Genet.*, 14:457–460 (1996); Chee et al., *Nat. Genet.*, 14:610–614 (1996); Lockhart et al., *Nat. Genet.*, 14:675–680 (1996); Drobyshev et al., *Gene*, 188:45–52 (1997), all of which are incorporated herein by reference.

In a preferred embodiment, DNA molecules encoding the PN7718 are included in a microarray of the present invention. More preferably, DNA molecules having a sequence according to the sequence of SEQ ID NO:1 or SEQ ID NO:3 or the complement thereof are incorporated into a microarray of the present invention.

3. PN7718 Protein

In a second aspect of the present invention, an isolated PN7718 polypeptide is provided. In one embodiment, the PN7718 polypeptide comprises the full sequence of SEQ ID NO:2.

Additionally, the present invention also encompasses a polypeptide having an amino acid sequence that is at least 50%, preferably at least 60%, more preferably at least 75%, 80%, 85%, 90%, 91%, 92%, 93%, 94%, and even more preferably at least 95%, 96%, 97%, 98%, or 99% identical to the amino acid sequence of SEQ ID NO:2. Preferably, the homologous polypeptide retains one or more activities of PN7718. More preferably, the homologous polypeptide is capable of interacting with cyclophilin C. In a specific embodiment, the homologous polypeptide is a naturally occurring variant of PN7718 identified in a human population. Such a variant may be identified by assaying the PN7718 nucleic acids or protein in a population, as is generally known in the art. The nucleic acid variant thus identified can be isolated or alternatively produced by mutagenesis in the PN7718 nucleic acid of the sequence of SEQ ID NO:1 or SEQ ID NO:3. The PN7718 variant can then be prepared by recombinant expression from the nucleic acid variant.

In another embodiment, the present invention also provides an isolated polypeptide that is encoded by an isolated nucleic acid molecule that specifically hybridizes to the isolated PN7718 nucleic acid molecule of SEQ ID NO:1 or SEQ ID NO:3 or the complement thereof under stringent conditions. Preferably, the polypeptide retains one or more activities of PN7718. More preferably, the polypeptide is capable of interacting with cyclophilin C.

The present invention further encompasses fragments of PN7718 protein having a contiguous span of at least 6, 7, 8, 9, 10, 11, 12, 13, 14, 15, 16, 17, 18, 19, 20, 25, 30, 35, 50, 75, 100, 125 or 150 amino acids of the sequence of SEQ ID NO:2, but less than the full length of the sequence of SEQ ID NO:2. For example, such fragments can be generated as a result of the deletion of a contiguous span of a certain number of amino acids from either or both of the amino and carboxyl termini of the PN7718 protein having the sequence of SEQ ID NO:2. In specific embodiments, a polypeptide is provided including a contiguous span of at least 4, 5, 6, 7, 8, 9, 10, 11, 12, 13, 14, 15, 18, 20, 25, 30, 35, 50, 75, 100, 125 or 150 amino acids of the sequence of SEQ ID NO:2, and the polypeptide is capable of interacting with cyclophilin C. In other specific embodiments, the PN7718 fragments contain immunogenic or antigenic epitopes. Such epitopes can be readily determined by computer programs such as MacVector from International Biotechnologies, Inc. and Protean from DNAStar. In addition, epitopes can also be selected experimentally by any methods known in the art, e.g., in U.S. Pat. Nos. 4,833,092 and 5,194,392, both of which are incorporated herein by reference.

In addition, the present invention is also directed to polypeptides that are homologous to the foregoing PN7718 fragments. Such a homologous polypeptide may have the same length as one of the foregoing PN7718 fragments of the present invention (e.g., from 5 to 50, from 5 to 30, or from 7 to 25, or preferably 8 to 20 amino acids) but has an amino acid sequence that is at least 75%, 80%, 85%, 90%, preferably at least 95%, 96%, 97%, 98%, or, more preferably, at least 99% identical to the amino acid sequence of the corresponding PN7718 fragment. Preferably, the homologous peptides are capable of interacting with cyclophilin C.

The protein fragments of the present invention may still retain the biological functions of PN7718 or one or more activities of PN7718. For example, such protein fragments may be immunogenic and thus can be used in producing antibodies against PN7718. The protein fragments may be antigenic and thus can bind to an antibody specific against PN7718. The protein fragments of the present invention may also retain the ability to interact with cyclophilin C, and thus can be used in screening assays for modulators of cyclophilin C-PN7718 interaction. In addition, where a protein fragment of the present invention lacks one or more PN7718 activities, it can be used as a competitive inhibitor of PN7718 activities by competing with PN7718 protein for binding partners.

Additionally, the present invention further relates to a hybrid polypeptide having any one of the foregoing polypeptides of the present invention covalently linked to another polypeptide. Such other polypeptide can also be one of the foregoing polypeptides of the present invention. Alternatively, such other polypeptide is not one of the foregoing polypeptides of the present invention. Preferably, such other polypeptide is a non-PN7718 polypeptide. In a specific embodiment, the hybrid polypeptide has a cyclophilin C or homologue, derivative or fragment thereof covalently linked to any one of the foregoing polypeptides of the present invention. For example, the hybrid polypeptide can comprise a cyclophilin C fragment and a PN7718 protein or homologue or fragment thereof. The covalent linkage in the hybrid polypeptide of the present invention can be merely a covalent bond between the two components of the hybrid polypeptide. Alternatively, any linker molecules may be used. For example, a peptide or a non-peptidic organic molecule may be used as a linker molecule.

4. Isolation of PN7718-Interacting Proteins

The present invention also provides methods for identifying additional proteins that interact with PN7718. Naturally occurring PN7718-interacting proteins will be useful in further elucidating the biological processes and disease pathways PN7718 is involved in. The interactors identified in the methods of the present invention can be used in assays for detecting or modulating PN7718. In addition, the protein interactors can also be used in screening assays for identifying modulators of the interactions between PN7718 and the PN7718-interacting proteins. Such modulators may be useful in modulating PN7718 activities and in treating PN7718-associated diseases and disorders.

A number of biochemical approaches known in the art can be used to identify interacting proteins. For example, a PN7718 antibody as provided in the present invention in Section 7 may be used in coimmunoprecipitation assays to isolate PN7718-interacting proteins from cell extracts or other sources based on the binding affinity between PN7718 and its interactors. Optionally, cross-linking techniques may be used to stabilize the binding of PN7718 and its interactors. Identities of the isolated protein interacting partners can be characterized by, e.g., mass spectrometry. See e.g., Rout et al., *J. Cell. Biol.*, 148:635–651 (2000); Houry et al., *Nature*, 402:147–154 (1999); Winter et al., *Curr. Biol.*, 7:517–529 (1997). A popular approach useful in large-scale screening is the phage display method, in which filamentous bacteriophage particles are made by recombinant DNA technologies to express a peptide or protein of interest fused to a capsid or coat protein of the bacteriophage. A whole library of peptides or proteins of interest can be expressed and a bait protein can be used to screen the library to identify peptides or proteins capable of binding to the bait protein. See e.g., U.S. Pat. Nos. 5,223,409; 5,403,484; 5,571,698; and 5,837,500.

In a preferred embodiment, the yeast two-hybrid system or one of the derivative forms thereof is used. Examples of suitable two-hybrid systems known in the art include, but are not limited to, those disclosed in U.S. Pat. Nos. 5,283,173; 5,525,490; 5,585,245; 5,637,463; 5,695,941; 5,733,726; 5,776,689; 5,885,779; 5,905,025; 6,037,136; 6,057,101; 6,114,111; and Bartel and Fields, eds., *The Yeast Two-Hybrid System*, Oxford University Press, New York, N.Y., 1997, all of which are incorporated herein by reference.

Typically, in a transcription-based two-hybrid assay, two chimeric genes are prepared encoding two fusion proteins: one contains a DNA binding domain fused to a bait protein or a fragment thereof, while the other fusion protein includes a transcription activation domain fused to a prey protein to be identified or tested or a fragment thereof. For the purpose of convenience, the two fusion proteins are referred to as "bait fusion protein" and "prey fusion protein," respectively. The chimeric genes encoding the fusion proteins are termed "bait chimeric gene" and "prey chimeric gene," respectively. Typically, a "bait vector" and a "prey vector" are provided for the expression of a bait chimeric gene and a prey chimeric gene, respectively. To identify a PN7718-interacting protein, PN7718 protein or a fragment thereof can be used as the bait protein. In large scale screening assays, a library of prey chimeric genes may be expressed to produce a battery of prey fusion proteins, each having the same transcription activation domain fused to a unique prey protein.

4.1. Vectors

Many types of vectors can be used in a transcription-based two-hybrid assay. Methods for the construction of bait vectors and prey vectors should be apparent to skilled artisans apprised of the present disclosure. See generally, *Current Protocols in Molecular Biology*, Vol. 2, Ed. Ausubel, et al., Greene Publish. Assoc. & Wiley Interscience, Ch. 13, 1988; Glover, *DNA Cloning*, Vol. II, IRL Press, Wash., D.C., Ch. 3, 1986; Bitter, et al., in *Methods in Enzymology* 153:516–544 (1987); *The Molecular Biology of the Yeast Saccharomyces*, Eds. Strathern et al., Cold Spring Harbor Press, Vols. I and II, 1982; and Rothstein in *DNA Cloning: A Practical Approach*, Vol. 11, Ed. DM Glover, IRL Press, Wash., D.C., 1986.

Generally, the bait and prey vectors include an expression cassette having a promoter operably linked to a chimeric gene for the transcription of the chimeric gene. The vectors may also include an origin of DNA replication for the replication of the vectors in host cells and a replication origin for the amplification of the vectors in, e.g., *E. coli*, and selection marker(s) for selecting and maintaining only those host cells harboring the vectors. Additionally, the expression cassette preferably also contains inducible elements, which function to control the expression of a chimeric gene. Making the expression of the chimeric genes inducible and controllable is especially important in the event that the fusion proteins or components thereof are toxic to the host cells. Other regulatory sequences such as transcriptional enhancer sequences and translation regulation sequences (e.g., Shine-Dalgarno sequence) can also be included in the expression cassette. Termination sequences such as the bovine growth hormone, SV40, lacZ and AcMNPV polyhedral polyadenylation signals may also be operably linked to a chimeric gene in the expression cassette. An epitope tag coding sequence for detection and/or purification of the fusion proteins can also be operably linked to the chimeric gene in the expression cassette. Examples of useful epitope tags include, but are not limited to, influenza virus hemagglutinin (HA), Simian Virus 5 (V5), polyhistidine (6×His), c-myc, lacZ, GST, and the like. Proteins with polyhistidine tags can be easily detected and/or purified with Ni affinity columns, while specific antibodies to many epitope tags are generally commercially available. The vectors can be introduced into the host cells by any techniques known in the art, e.g., by direct DNA transformation, microinjection, electroporation, viral infection, lipofection, gene gun, and the like. The bait and prey vectors can be maintained in host cells in an extrachromosomal state, i.e., as self-replicating plasmids or viruses. Alternatively, one or both vectors can be integrated into chromosomes of the host cells by conventional techniques such as selection of stable cell lines or site-specific recombination.

The assays of the present invention can be conducted in many different host cells, including but not limited to bacteria, yeast cells, plant cells, insect cells, and mammalian cells. A skilled artisan will recognize that the designs of the vectors can vary with the host cells used. In one embodiment, the assay is conducted in prokaryotic cells such as *Escherichia coli, Salmonella, Klebsiella, Pseudomonas, Caulobacter*, and *Rhizobium*. Suitable origins of replication for the expression vectors useful in this embodiment of the present invention include, e.g., the ColE1, pSC101, and M13 origins of replication. Examples of suitable promoters include, for example, the T7 promoter, the lacZ promoter, and the like. In addition, inducible promoters are also useful in modulating the expression of the chimeric genes. For example, the lac operon from bacteriophage lambda plac5 is well known in the art and is inducible by the addition of IPTG to the growth medium. Other known inducible promoters useful in a bacteria expression system include pL of bacteriophage lambda, the trp promoter, and hybrid promoters such as the tac promoter, and the like.

In addition, selection marker sequences for selecting and maintaining only those prokaryotic cells expressing the desirable fusion proteins should also be incorporated into the expression vectors. Numerous selection markers including auxotrophic markers and antibiotic resistance markers are known in the art and can all be useful for purposes of this invention. For example, the bla gene which confers ampicillin resistance is the most commonly used selection marker in prokaryotic expression vectors. Other suitable markers include genes that confer neomycin, kanamycin, or hygromycin resistance to the host cells. In fact, many vectors are commercially available from vendors such as Invitrogen Corp. of San Diego, Calif., Clontech Corp. of Palo Alto, Calif., BRL of Bethesda, Md., and Promega Corp. of Madison, Wis. These commercially available vectors, e.g., pBR322, pSPORT, pBluescriptIISK, pcDNAI, and pcDNAII all have a multiple cloning site into which the chimeric genes of the present invention can be conveniently inserted using conventional recombinant techniques. The constructed expression vectors can be introduced into host cells by various transformation or transfection techniques generally known in the art.

In another embodiment, mammalian cells are used as host cells for the expression of the fusion proteins and detection of protein—protein interactions. For this purpose, virtually any mammalian cells can be used including normal tissue cells, stable cell lines, and transformed tumor cells. Conveniently, mammalian cell lines such as CHO cells, Jurkat T cells, NIH 3T3 cells, HEK-293 cells, CV-1 cells, COS-1 cells, HeLa cells, VERO cells, MDCK cells, WI38 cells, and the like are used. Mammalian expression vectors are well known in the art and many are commercially available. Examples of suitable promoters for the transcription of the chimeric genes in mammalian cells include viral transcription promoters derived from adenovirus, simian virus 40 (SV40) (e.g., the early and late promoters of SV40), Rous sarcoma virus (RSV), and cytomegalovirus (CMV) (e.g., CMV immediate-early promoter), human immunodeficiency virus (HIV) (e.g., long terminal repeat (LTR)), vaccinia virus (e.g., 7.5K promoter), and herpes simplex virus (HSV) (e.g., thymidine kinase promoter). Inducible promoters can also be used. Suitable inducible promoters include, for example, the tetracycline responsive element (TRE) (See Gossen et al., *Proc. Natl. Acad. Sci. USA*, 89:5547–5551 (1992)), metallothionein IIA promoter, ecdysone-responsive promoter, and heat shock promoters. Suitable origins of replication for the replication and maintenance of the expression vectors in mammalian cells include, e.g., the Epstein Barr origin of replication in the presence of the Epstein Barr nuclear antigen (see Sugden et al., *Mole. Cell. Biol.*, 5:410–413 (1985)) and the SV40 origin of replication in the presence of the SV40 T antigen (which is present in COS-1 and COS-7 cells) (see Margolskee et al., *Mole. Cell. Biol.*, 8:2837 (1988)). Suitable selection markers include, but are not limited to, genes conferring resistance to neomycin, hygromycin, zeocin, and the like. Many commercially available mammalian expression vectors may be useful for the present invention, including, e.g., pCEP4, pcDNAI, pIND, pSecTag2, pVAX1, pcDNA3.1, and pBI-EGFP, and pDisplay. The vectors can be introduced into mammalian cells using any known techniques such as calcium phosphate precipitation, lipofection, electroporation, and the like. The bait vector and prey vector can be co-transformed into the same cell or, alternatively, introduced into two different cells which are subsequently fused together by cell fusion or other suitable techniques.

Viral expression vectors, which permit introduction of recombinant genes into cells by viral infection, can also be used for the expression of the fusion proteins. Viral expression vectors generally known in the art include viral vectors based on adenovirus, bovine papilloma virus, murine stem cell virus (MSCV), MFG virus, and retrovirus. See Sarver, et al., *Mol. Cell. Biol.*, 1: 486 (1981); Logan & Shenk, *Proc. Natl. Acad. Sci. USA*, 81:3655–3659 (1984); Mackett, et al., *Proc. Natl. Acad. Sci. USA*, 79:7415–7419 (1982); Mackett, et al., *J. Virol.*, 49:857–864 (1984); Panicali, et al., *Proc. Natl. Acad. Sci. USA*, 79:4927–4931 (1982); Cone & Mulligan, *Proc. Natl. Acad. Sci. USA*, 81:6349–6353 (1984); Mann et al., *Cell*, 33:153–159 (1993); Pear et al., *Proc. Natl. Acad. Sci. USA*, 90:8392–8396 (1993); Kitamura et al., *Proc. Natl. Acad. Sci. USA*, 92:9146–9150 (1995); Kinsella et al., *Human Gene Therapy*, 7:1405–1413 (1996); Hofmann et al., *Proc. Natl. Acad. Sci. USA*, 93:5185–5190 (1996); Choate et al., *Human Gene Therapy*, 7:2247 (1996); WO 94/19478; Hawley et al., *Gene Therapy*, 1:136 (1994) and Rivere et al., *Genetics*, 92:6733 (1995), all of which are incorporated by reference.

Generally, to construct a viral vector, a chimeric gene according to the present invention can be operably linked to a suitable promoter. The promoter-chimeric gene construct is then inserted into a non-essential region of the viral vector, typically a modified viral genome. This results in a viable recombinant virus capable of expressing the fusion protein encoded by the chimeric gene in infected host cells. Once in the host cell, the recombinant virus typically is integrated into the genome of the host cell. However, recombinant bovine papilloma viruses typically replicate and remain as extrachromosomal elements.

In another embodiment, the detection assays of the present invention are conducted in plant cell systems. Methods for expressing exogenous proteins in plant cells are well known in the art. See generally, Weissbach & Weissbach, *Methods for Plant Molecular Biology*, Academic Press, NY, 1988; Grierson & Corey, *Plant Molecular Biology*, 2d Ed., Blackie, London, 1988. Recombinant virus expression vectors based on, e.g., cauliflower mosaic virus (CaMV) or tobacco mosaic virus (TMV) can all be used. Alternatively, recombinant plasmid expression vectors such as Ti plasmid vectors and Ri plasmid vectors are also useful. The chimeric genes encoding the fusion proteins of the present invention can be conveniently cloned into the expression vectors and placed under control of a viral promoter such as the 35S RNA and 19S RNA promoters of CaMV or the coat protein promoter of TMV, or of a plant promoter, e.g., the promoter of the small subunit of RUBISCO and heat shock promoters (e.g., soybean hsp17.5-E or hsp17.3-B promoters).

In addition, the two-hybrid assays of the present invention can also be conducted in insect cells, e.g., *Spodoptera frugiperda* cells, using a baculovirus expression system. Expression vectors and host cells useful in this system are well known in the art and are generally available from various commercial vendors. For example, the chimeric genes of the present invention can be conveniently cloned into a non-essential region (e.g., the polyhedrin gene) of an *Autographa californica* nuclear polyhedrosis virus (AcNPV) vector and placed under control of an AcNPV promoter (e.g., the polyhedrin promoter). The non-occluded recombinant viruses thus generated can be used to infect host cells, such as *Spodoptera frugiperda* cells, in which the chimeric genes are expressed. See U.S. Pat. No. 4,215,051.

In a preferred embodiment of the present invention, the fusion proteins are expressed in a yeast expression system using yeasts such as *Saccharomyces cerevisiae*, *Hansenula polymorpha*, *Pichia pastoris*, and *Schizosaccharomyces pombe*. The expression of recombinant proteins in yeasts is a well-developed field, and the techniques useful in this respect are disclosed in detail in *The Molecular Biology of the Yeast Saccharomyces*, Eds. Strathern et al., Vols. I and II, Cold Spring Harbor Press, 1982; Ausubel et al., *Current Protocols in Molecular Biology*, New York, Wiley, 1994; and Guthrie and Fink, *Guide to Yeast Genetics and Molecular Biology*, in *Methods in Enzymology*, Vol. 194, 1991, all of which are incorporated herein by reference. Sudbery, *Curr. Opin. Biotech.*, 7:517–524 (1996) reviews the successes in the art of expressing recombinant proteins in various yeast species; the entire content and references cited therein are incorporated herein by reference. In addition, Bartel and Fields, eds., *The Yeast Two-Hybrid System*, Oxford University Press, New York, N.Y., 1997 contains extensive discussions of recombinant expression of fusion proteins in yeasts in the context of various yeast two-hybrid systems, and cites numerous relevant references. These and other methods known in the art can all be used for purposes of the present invention. The application of such methods to the present invention should be apparent to a skilled artisan apprised of the present disclosure.

Generally, each of the two chimeric genes is included in a separate expression vector (bait vector and prey vector). Both vectors can be co-transformed into a single yeast host cell. As will be apparent to a skilled artisan, it is also possible to express both chimeric genes from a single vector. In a preferred embodiment, the bait vector and prey vector are introduced into two haploid yeast cells of opposite mating types, e.g., a-type and alpha-type, respectively. The two haploid cells can be mated at a desired time to form a diploid cell expressing both chimeric genes.

Generally, the bait and prey vectors for recombinant expression in yeast include a yeast replication origin such as the 2μ origin or the ARSH4 sequence for the replication and maintenance of the vectors in yeast cells. Preferably, the vectors also have a bacterial origin of replication (e.g., ColE1) and a bacterial selection marker (e.g., amp$^R$ marker, i.e., bla gene). Optionally, the CEN6 centromeric sequence is included to control the replication of the vectors in yeast cells. Any constitutive or inducible promoters capable of driving gene transcription in yeast cells may be employed to control the expression of the chimeric genes. Such promoters are operably linked to the chimeric genes. Examples of suitable constitutive promoters include, but are not limited to, the yeast ADH1, PGK1, TEF2, GPD1, HIS3, and CYC1 promoters. Examples of suitable inducible promoters include, but are not limited to, the yeast GAL1 (inducible by galactose), CUP1 (inducible by Cu$^{++}$), and FUS1 (inducible by pheromone) promoters; the AOX/MOX promoter from *H. polymorpha* and *P. pastoris* (repressed by glucose or ethanol and induced by methanol); chimeric promoters such as those that contain Lex A operators (inducible by LexA-containing transcription factors); and the like. Inducible promoters are preferred when the fusion proteins encoded by the chimeric genes are toxic to the host cells. If it is desirable, certain transcription-repressing sequences such as the upstream repressing sequence (URS) from the SPO13 promoter can be operably linked to the promoter sequence, e.g., to the 5' end of the promoter region. Such upstream repressing sequences function to fine-tune the expression level of the chimeric genes.

Preferably, a transcriptional termination signal is operably linked to the chimeric genes in the vectors. Generally, transcriptional termination signal sequences derived from, e.g., the CYC1 and ADH1 genes can be used.

Additionally, it is preferred that the bait vector and prey vector each contain one or more selectable markers for the selection and maintenance of only those yeast cells that harbor a chimeric gene. Any selectable markers known in the art can be used for purposes of this invention so long as yeast cells expressing the chimeric gene(s) can be positively identified or negatively selected. Examples of markers that can be positively identified are those based on color assays, including the lacZ gene which encodes beta-galactosidase, the firefly luciferase gene, secreted alkaline phosphatase, horseradish peroxidase, the blue fluorescent protein (BFP), and the green fluorescent protein (GFP) gene (see Cubitt et al., *Trends Biochem. Sci.*, 20:448–455 (1995)). Other markers emitting fluorescence, chemiluminescence, UV absorption, infrared radiation, and the like can also be used. Among the markers that can be used for selection are auxotrophic markers including, but not limited to, URA3, HIS3, TRP1, LEU2, LYS2, ADE2, and the like. Typically, for purposes of auxotrophic selection, the yeast host cells transformed with bait vector and/or prey vector are cultured in a medium lacking a particular nutrient. Other selectable markers are not based on auxotrophies, but rather on resistance or sensitivity to an antibiotic or other xenobiotic. Examples of such markers include, but are not limited to, the chloramphenicol acetyl transferase (CAT) gene, which confers resistance to chloramphenicol; the CAN1 gene, which encodes an arginine permease and thereby renders cells sensitive to canavanine (see Sikorski et al., *Meth. Enzymol.*, 194:302–318 (1991)); the bacterial kanamycin resistance gene (kan$^R$), which renders eukaryotic cells resistant to the aminoglycoside G418 (see Wach et al., *Yeast*, 10:1793–1808 (1994)); and the CYH2 gene, which confers sensitivity to cycloheximide (see Sikorski et al., *Meth. Enzymol.*, 194: 302–318 (1991)). In addition, the CUP1 gene, which encodes metallothionein and thereby confers resistance to copper, is also a suitable selection marker. Each of the above selection markers may be used alone or in combination. One or more selection markers can be included in a particular bait or prey vector. The bait vector and prey vector may have the same or different selection markers. In addition, the selection pressure can be placed on the transformed host cells either before or after mating the haploid yeast cells.

As will be apparent, the selection markers used should complement the host strains in which the bait and/or prey vectors are expressed. In other words, when a gene is used as a selection marker gene, a yeast strain lacking the selection marker gene (or having an inactivating mutation in the corresponding gene) should be used as host cells. Numerous yeast strains or derivative strains corresponding to various selection markers are known in the art. Many of them have been developed specifically for certain yeast two-hybrid systems. The application and optional modification of such strains with respect to the present invention will be apparent to a skilled artisan apprised of the present disclosure. Methods for genetically manipulating yeast strains using genetic crossing or recombinant mutagenesis are well known in the art. See e.g., Rothstein, *Meth. Enzymol.*, 101:202–211 (1983). By way of example, the following yeast strains are well known in the art, and can be used in the present invention upon necessary modifications and adjustment:

L40 strain which has the genotype MATa his3Δ200 trp1-901 leu2-3,112 ade2 LYS2::(lexAop)4-HIS3 URA3::(lex-Aop)8-lacZ;

EGY48 strain which has the genotype MATα trp1 his3 ura3 6ops-LEU2; and

MaV103 strain which has the genotype MATα ura3-52 leu2-3,112 trp1-901 his3Δ200 ade2-101 gal4Δ gal80Δ SPAL10::URA3 GAL1::HIS3::lys2 (see Kumar et al., *J. Biol. Chem.* 272:13548–13554 (1997); Vidal et al., *Proc. Natl. Acad. Sci. USA*, 93:10315–10320 (1996)). Such strains are generally available in the research community, and can also be obtained by simple yeast genetic manipulation. See, e.g., *The Yeast Two-Hybrid System*, Bartel and Fields, eds., pages 173–182, Oxford University Press, New York, N.Y., 1997.

In addition, the following yeast strains are commercially available:

Y190 strain which is available from Clontech, Palo Alto, Calif. and has the genotype MATa gal4 gal80 his3Δ200 trp1-901 ade2-101 ura3-52 leu2-3, 112 URA3::GAL1-lacZ LYS2::GAL1-HIS3 cyh$^r$; and YRG-2 Strain which is available from Stratagene, La Jolla, Calif. and has the genotype MATα ura3-52 his3-200 ade2-101 lys2-801 trp1-901 leu2-3, 112 gal4-542 gal80-538 LYS2::GAL1-HIS3 URA3::GAL1/CYC1-lacZ.

In fact, different versions of vectors and host strains specially designed for yeast two-hybrid system analysis are available in kits from commercial vendors such as Clontech, Palo Alto, Calif. and Stratagene, La Jolla, Calif., all of which can be modified for use in the present invention.

4.2. Reporters

Generally, in a transcription-based two-hybrid assay, the interaction between a bait fusion protein and a prey fusion protein brings the DNA-binding domain and the transcription-activation domain into proximity forming a functional transcriptional factor, which acts on a specific promoter to drive the expression of a reporter gene. The transcription activation domain and the DNA-binding domain may be selected from various known transcriptional activators, e.g., GAL4, GCN4, ARD1, the human estrogen receptor, *E. coli* Lex A protein, herpes simplex virus VP16 (Triezenberg et al., *Genes Dev.* 2:718–729 (1988)), the *E. coli* B42 protein (acid blob, see Gyuris et al., *Cell*, 75:791–803 (1993)), NF-kB p65, and the like. The reporter gene and the promoter driving its transcription typically are incorporated into a separate reporter vector. Alternatively, the host cells are engineered to contain such a promoter-reporter gene sequence in their chromosomes. Thus, the interaction or lack of interaction between two interacting protein members of a protein complex can be determined by detecting or measuring changes in the expression of the assay system's reporter. Although the reporters and selection markers can be of similar types and used in a similar manner in the present invention, the reporters and selection markers should be carefully selected in a particular detection assay such that they are distinguishable from each other and do not interfere with each other's function.

Many different types of reporters are useful in the screening assays. For example, a reporter protein may be a fusion protein having an epitope tag fused to a protein. Commonly used and commercially available epitope tags include sequences derived from, e.g., influenza virus hemagglutinin (HA), Simian Virus 5 (V5), polyhistidine (6×His), c-myc, lacZ, GST, and the like. Antibodies specific to these epitope tags are generally commercially available. Thus, the expressed reporter can be detected using an epitope-specific antibody in an immunoassay.

In another embodiment, the reporter is selected such that it can be detected by a color-based assay. Examples of such reporters include, e.g., the lacZ protein (beta-galactosidase), the green fluorescent protein (GFP), which can be detected by fluorescence assay and sorted by flow-activated cell sorting (FACS) (See Cubitt et al., *Trends Biochem. Sci.*, 20:448–455 (1995)), secreted alkaline phosphatase, horseradish peroxidase, the blue fluorescent protein (BFP), and luciferase photoproteins such as aequorin, obelin, mnemiopsin, and berovin (See U.S. Pat. No. 6,087,476, which is incorporated herein by reference).

Alternatively, an auxotrophic factor is used as a reporter in a host strain deficient in the auxotrophic factor. Thus, suitable auxotrophic reporter genes include, but are not limited to, URA3, HIS3, TRP1, LEU2, LYS2, ADE2, and the like. For example, yeast cells containing a mutant URA3 gene can be used as host cells. Such cells lack URA3-encoded functional orotidine-5'-phosphate decarboxylase, an enzyme required by yeast cells for the biosynthesis of uracil (Ura⁻ phenotype). As a result, the cells are unable to grow on a medium lacking uracil. However, wild-type orotidine-5'-phosphate decarboxylase catalyzes the conversion of a non-toxic compound 5-fluoroorotic acid (5-FOA) to a toxic product, 5-fluorouracil. Thus, yeast cells containing a wild-type URA3 gene are sensitive to 5-FOA and cannot grow on a medium containing 5-FOA. Therefore, when the interaction between the interacting protein members in the fusion proteins results in the expression of active orotidine-5'-phosphate decarboxylase, the Ura⁻ (5-FOA resistant) yeast cells will be able to grow on a uracil deficient medium (SC-Ura plates). However, such cells will not survive on a medium containing 5-FOA. Thus, protein—protein interactions can be detected based on cell growth.

Additionally, antibiotic resistance reporters can also be employed in a similar manner. In this respect, host cells sensitive to a particular antibiotic are used. Antibiotic resistance reporters include, for example, chloramphenicol acetyl transferase (CAT) gene and the kan$^R$ gene, which confers resistance to G418 in eukaryotes and to kanamycin in prokaryotes.

Thus, the interaction between PN7718 protein and a particular prey protein can be detected by detecting reporter gene expression when two fusion proteins containing the PN7718 protein and the prey protein, respectively, are co-expressed in a host cell. The identity of the interacting prey protein can then be deciphered by isolating the prey chimeric gene encoding the interacting prey fusion protein and sequencing the nucleic acid molecule encoding the prey protein.

5. Protein Complexes

The present invention provides protein complexes formed by PN7718 and a PN7718-interacting protein. The PN7718-interacting protein may be identified by the methods described in Section 4.

In a preferred embodiment, the protein complexes comprise cyclophilin C and PN7718. The present invention also provides a protein complex formed from the interaction between a homologue, derivative or fragment of cyclophilin C and PN7718 in accordance with the present invention. In addition, the present invention further encompasses a protein complex having cyclophilin C and a homologue, derivative or fragment of PN7718 in accordance with the present invention. In yet another embodiment, a protein complex is provided having a homologue, derivative or fragment of cyclophilin C and a homologue, derivative or fragment of PN7718 in accordance with the present invention. In other words, one or more of the interacting protein members of a protein complex of the present invention may be a native protein or a homologue, derivative or fragment of a native protein.

PN7718 fragments capable of interacting with cyclophilin C can be identified by the combination of molecular engineering of a PN7718-encoding nucleic acid and a method for testing protein—protein interaction. For example, the coordinates in Table 1 can be used as starting points and various PN7718 fragments falling within the coordinates can be generated by deletions from either or both ends of the coordinates. The resulting fragments can be tested for their ability to interact with cyclophilin C using any methods known in the art for detecting protein—protein interactions (e.g., yeast two-hybrid method). Alternatively, various PN7718 fragments can be made by chemical synthesis. The PN7718 fragments can then be tested for its ability to interact with cyclophilin C using any method known in the art for detecting protein—protein interactions. Examples of such methods include protein affinity chromatography, affinity blotting, in vitro binding assays, yeast two-hybrid assays, and the like. Likewise, cyclophilin C fragments capable of interacting with PN7718 can also be identified in a similar manner.

Thus, for example, one interacting partner in the protein complexes can be a complete native cyclophilin C, a cyclophilin C homologue capable of interacting with the PN7718, a cyclophilin C derivative, a derivative of the cyclophilin C homologue, a cyclophilin C fragment capable of interacting with PN7718 (cyclophilin C fragment(s) containing the coordinates shown in Table 1), a derivative of the cyclophilin C fragment, or a fusion protein containing (1) complete native cyclophilin C, (2) a cyclophilin C homologue capable of interacting with PN7718 or (3) a cyclophilin C fragment capable of interacting with PN7718.

Besides native PN7718, useful interacting partners for cyclophilin C or a homologue or derivative or fragment thereof also include homologues of PN7718 capable of interacting with cyclophilin C, derivatives of the native or homologue PN7718 capable of interacting with cyclophilin C, fragments of the PN7718 capable of interacting with cyclophilin C (e.g., a fragment containing the identified interacting regions shown in Table 1), derivatives of the PN7718 fragments, or fusion proteins containing (1) a complete PN7718, (2) a PN7718 homologue capable of interacting with cyclophilin C or (3) a PN7718 fragment capable of interacting with cyclophilin C.

In a specific embodiment of the protein complex of the present invention, two or more interacting partners (cyclophilin C and PN7718, or homologue, derivative or fragment thereof) are directly fused together, or covalently linked together through a peptide linker, forming a hybrid protein having a single unbranched polypeptide chain. Thus, the protein complex may be formed by "intramolecular" interactions between two portions of the hybrid protein. Again, one or both of the fused or linked interacting partners in this protein complex may be a native protein or a homologue, derivative or fragment of a native protein.

The protein complexes of the present invention can also be in a modified form. For example, an antibody selectively immunoreactive with the protein complex can be bound to the protein complex. Alternatively, the protein members in the protein complex may be cross-linked for purposes of stabilization. Various crosslinking methods may be used. For example, a bifunctional reagent in the form of R-S-S-R' may be used in which the R and R' groups can react with certain amino acid side chains in the protein complex forming covalent linkages. See e.g., Traut et al., in Creighton ed., *Protein Function: A Practical Approach*, IRL Press, Oxford, 1989; Baird et al., *J. Biol. Chem.*, 251:6953–6962 (1976). Other useful crosslinking agents include, e.g., Denny-Jaffee reagent, a heterobiofunctional photoactivable moiety cleavable through an azo linkage (See Denny et al., *Proc. Natl. Acad. Sci. USA*, 81:5286–5290 (1984)), and $^{125}$I-{S-[N-(3-iodo-4-azidosalicyl)cysteaminyl]-2-thiopyridine}, a cysteine-specific photocrosslinking reagent (see Chen et al., *Science*, 265:90–92 (1994)).

The above-described protein complexes may further include any additional components e.g., other proteins, nucleic acids, lipid molecules, monosaccharides or polysaccharides, ions or other molecules. Compounds that increase or decrease the stability of the protein complexes, e.g., those identified in the screening assays disclosed below in Section 10 may also be included.

6. Methods of Preparing PN7718 and Protein Complexes

The PN7718 proteins and the protein complexes of the present invention can be prepared by a variety of methods. Specifically, a protein complex can be isolated directly from an animal tissue sample, preferably a human tissue sample containing the protein complex. Alternatively, a protein complex can be purified from host cells that recombinantly express the members of the protein complex. As will be apparent to a skilled artisan, a protein complex can be prepared from a tissue sample or recombinant host cell by coimmunoprecipitation using an antibody immunoreactive with an interacting protein partner, or preferably an antibody selectively immunoreactive with the protein complex as will be discussed in detail below. The antibodies can be monoclonal or polyclonal. Coimmunoprecipitation is a commonly used method in the art for isolating or detecting bound proteins. In this procedure, generally a serum sample or tissue or cell lysate is admixed with a suitable antibody. The protein complex bound to the antibody is precipitated and washed. The bound protein complexes are then eluted. If the protein complex dissociates during the elution, then the dissociated interacting members may be put together to reconstitute the protein complex.

Alternatively, immunoaffinity chromatography and immunoblotting techniques may also be used in isolating the protein complexes from native tissue samples or recombinant host cells using an antibody immunoreactive with an interacting protein partner, or preferably an antibody selectively immunoreactive with the protein complex. For example, in protein immunoaffinity chromatography, the antibody may be covalently or non-covalently coupled to a matrix such as Sepharose in, e.g., a column. The tissue sample or cell lysate from the recombinant cells can then be contacted with the antibody on the matrix. The column is then washed with a low-salt solution to wash off the unbound components. The protein complexes that are retained in the column can be then eluted from the column using a high-salt solution, a competitive antigen of the antibody, a chaotropic solvent, or sodium dodecyl sulfate (SDS), or the like. In immunoblotting, crude protein samples from a tissue sample or recombinant host cell lysate can be fractionated by polyacrylamide gel electrophoresis (PAGE) and then transferred to a membrane, e.g., nitrocellulose. Components of the protein complex can then be located on the membrane and identified by a variety of techniques, e.g., probing with specific antibodies.

As will be apparent to a person of ordinary skill in the art, the PN7718 protein and its interacting proteins can also be isolated or purified separately and independently from tissue samples or recombinant host cells using similar methods as described above. For example, the PN7718 protein can be isolated by immunoprecipitation, immunoaffinity chromatography and immunobloting techniques using an antibody immunoreactive with the PN7718 protein as provided in the present disclosure in Section 7.

The independently isolated PN7718 and PN7718-interacting proteins, e.g., cyclophilin C, can be contacted with each other under conditions conducive to the interaction therebetween, thus forming a protein complex of the present invention. It is noted that different protein—protein interactions may require different conditions. As a starting point, for example, a buffer having 20 mM Tris-HCl, pH 7.0 and 500 mM NaCl may be used. Several different parameters may be varied, including temperature, pH, salt concentration, reducing agent, and the like. Some minor degree of experimentation may be required to determine the optimum incubation condition, this being well within the capability of one skilled in the art once apprised of the present disclosure.

In yet another embodiment, the protein complex of the present invention may be prepared from tissue samples or recombinant host cells or other suitable sources by protein affinity chromatography or affinity blotting. That is, one of the interacting protein partners is used to isolate the other interacting protein partner(s) by binding affinity thus forming protein complexes. Thus, an interacting protein partner prepared by purification from tissue samples or by recombinant expression or chemical synthesis may be bound covalently or non-covalently to a matrix such as Sepharose in, e.g., a chromatography column. The tissue sample or cell lysate from the recombinant cells can then be contacted with the bound protein on the matrix. A low-salt solution is used to wash off the unbound components, and a high-salt solution is then employed to elute the bound protein complexes in the column. In affinity blotting, crude protein samples from a tissue sample or recombinant host cell lysate can be fractionated on a polyacrylamide gel electrophoresis (PAGE) and then transferred to, e.g., a nitrocellulose membrane. The purified interacting protein member is then bound to its interacting protein partner(s) on the membrane forming protein complexes, which are then isolated from the membrane.

The same methods may be used to isolate PN7718 protein itself. That is, once a PN7718-containing protein complex is isolated preferably using an immobilized PN7718-interacting protein, e.g., cyclophilin C as bait, the bound PN7718 can be eluted and separated from its interacting protein to an isolated or purified state.

It will be apparent to skilled artisans that any recombinant expression methods may be used in the present invention for purposes of recombinantly expressing PN7718, its interacting proteins, and the PN7718-containing protein complexes. Generally, a nucleic acid encoding PN7718 or an interactor thereof can be introduced into a suitable host cell. For purposes of recombinantly forming a protein complex within a host cell, nucleic acids encoding two or more interacting protein members should be introduced into the host cell.

Typically, the nucleic acids, preferably in the form of DNA, are incorporated into a vector to form expression vectors capable of expressing the interacting protein member(s) once introduced into a host cell. Many types of vectors can be used for the present invention. Methods for the construction of an expression vector for purposes of this invention should be apparent to skilled artisans apprised of the present disclosure. See generally, *Current Protocols in Molecular Biology*, Vol. 2, Ed. Ausubel, et al., Greene Publish. Assoc. & Wiley Interscience, Ch. 13, 1988; Glover, *DNA Cloning*, Vol. II, IRL Press, Wash., D.C., Ch. 3, 1986; Bitter, et al., in *Methods in Enzymology* 153:516–544 (1987); *The Molecular Biology of the Yeast Saccharomyces*, Eds. Strathern et al., Cold Spring Harbor Press, Vols. I and II, 1982; and Sambrook et al., *Molecular Cloning: A Laboratory Manual*, Cold Spring Harbor Press, 1989.

Generally, the expression vectors include an expression cassette having a promoter operably linked to a DNA encoding an interacting protein member. The promoter can be a native promoter, i.e., the promoter found in naturally occurring cells to be responsible for the expression of the interacting protein member in the cells. Alternatively, the expression cassette can be a chimeric one, i.e., having a heterologous promoter that is not the native promoter responsible for the expression of the interacting protein member in naturally occurring cells. The expression vector may further include an origin of DNA replication for the replication of the vectors in host cells. Preferably, the expression vectors also include a replication origin for the amplification of the vectors in, e.g., *E. coli*, and selection marker(s) for selecting and maintaining only those host cells harboring the expression vectors. Additionally, the expression cassettes preferably also contain inducible elements, which function to control the transcription from the DNA encoding an interacting protein member. Other regulatory sequences such as transcriptional enhancer sequences and translation regulation sequences (e.g., Shine-Dalgarno sequence) can also be operably included in the expression cassettes. Termination sequences such as the polyadenylation signals from bovine growth hormone, SV40, lacZ and AcMNPV polyhedral protein genes may also be operably linked to the DNA encoding an interacting protein member in the expression cassettes. An epitope tag coding sequence for detection and/or purification of the expressed protein can also be operably linked to the DNA encoding an interacting protein member such that a fusion protein is expressed. Examples of useful epitope tags include, but are not limited to, influenza virus hemagglutinin (HA), Simian Virus 5 (V5), polyhistidine (6xHis), c-myc, lacZ, GST, and the like. Proteins with polyhistidine tags can be easily detected and/or purified with Ni affinity columns, while specific antibodies immunoreactive with many epitope tags are generally commercially available. The expression vectors may also contain components that direct the expressed protein extracellularly or to a particular intracellular compartment. Signal peptides, nuclear localization sequences, endoplasmic reticulum retention signals, mitochondrial localization sequences, myristoylation signals, palmitoylation signals, and transmembrane sequences are examples of optional vector components that can determine the destination of expressed proteins. When it is desirable to express two or more interacting protein members in a single host cell, the DNA fragments encoding the interacting protein members may be incorporated into a single vector or different vectors.

The thus-constructed expression vectors can be introduced into the host cells by any techniques known in the art, e.g., by direct DNA transformation, microinjection, electroporation, viral infection, lipofection, gene gun, and the like. The expression of the interacting protein members may be transient or stable. The expression vectors can be maintained in host cells in an extrachromosomal state, i.e., as self-replicating plasmids or viruses. Alternatively, the expression vectors can be integrated into chromosomes of the host cells by conventional techniques such as selection of stable cell lines or site-specific recombination. In stable cell lines, at least the expression cassette portion of the expression vector is integrated into a chromosome of the host cells. Homologues and fragments of the native interacting protein members can also be easily expressed using the recombinant methods described above. For example, to express a protein fragment, the DNA fragment can be selected and incorporated into the expression vector such that it only encodes the protein fragment. Likewise, a specific hybrid protein can be expressed using a recombinant DNA encoding the hybrid protein. Similarly, a homologue protein may be expressed from a DNA sequence encoding the homologue protein. A homologue-encoding DNA sequence may be obtained by manipulating the native protein-encoding sequence using recombinant DNA techniques. For this purpose, random or site-directed mutagenesis can be conducted using techniques generally known in the art. To make protein derivatives, for example, the amino acid sequence of a native interacting protein member may be changed in predetermined manners by site-directed DNA mutagenesis to create or remove consensus sequences for, e.g., phosphorylation by protein kinases, glycosylation, ribosylation, myristolation, palmytoylation, and the like. Alternatively, non-natural amino acids can be incorporated into an interacting protein member during the synthesis of the protein in recombinant host cells. For example, photoreactive lysine derivatives can be incorporated into an interacting protein member during translation by using a modified lysyl-tRNA. See, e.g., Wiedmann et al., *Nature*, 328:830–833 (1989); Musch et al., *Cell*, 69:343–352 (1992). Other photoreactive amino acid derivatives can also be incorporated in a similar manner. See, e.g., High et al., *J. Biol. Chem.*, 368:28745–28751 (1993). Indeed, the photoreactive amino acid derivatives thus incorporated into an interacting protein member can function to cross-link the protein to its interacting protein partner in a protein complex under predetermined conditions.

In addition, derivatives of the native interacting protein members of the present invention can also be prepared by chemically linking certain moieties to amino acid side chains of the native proteins.

If desired, the homologues and derivatives thus generated can be tested to determine whether they are capable of interacting with their intended interacting partners to form protein complexes. Testing can be conducted by e.g., the yeast two-hybrid system or other methods known in the art for detecting protein—protein interaction.

A hybrid protein as described above having cyclophilin C or a homologue, derivative, or fragment thereof covalently linked by a peptide bond or a peptide linker to PN7718 or a homologue, derivative, or fragment thereof, can be expressed recombinantly from a chimeric nucleic acid, e.g., a DNA or mRNA fragment encoding the fusion protein. Accordingly, the present invention also provides a nucleic acid encoding the hybrid protein of the present invention. In addition, an expression vector having incorporated therein a nucleic acid encoding the hybrid protein of the present invention is also provided. The methods for making such chimeric nucleic acids and expression vectors containing them will be apparent to skilled artisans apprised of the present disclosure.

7. Antibodies

In accordance with another aspect of the present invention, antibodies are provided which are immunoreactive with the PN7718 protein and/or a PN7718-containing protein complex of the present invention. In one embodiment, an antibody is immunoreactive with the PN7718 protein or a fragment thereof. In another embodiment, the antibody is selectively immunoreactive with a protein complex of the present invention. Specifically, the phrase "selectively immunoreactive with a protein complex" as used herein means that the immunoreactivity of the antibody of the present invention with the protein complex is substantially higher than that with the individual interacting members of the protein complex so that the binding of the antibody to the protein complex is readily distinguishable from the binding of the antibody to the individual interacting member proteins based on the strength of the binding affinities. Preferably, the binding constants differ by a magnitude of at least 2 fold, more preferably at least 5 fold, even more preferably at least 10 fold, and most preferably at least 100 fold. In a specific embodiment, the antibody is not substantially immunoreactive with the interacting protein members of the protein complex.

The antibodies of the present invention can be readily prepared using procedures generally known in the art. See, e.g., Harlow and Lane, *Antibodies: A Laboratory Manual*, Cold Spring Harbor Press, 1988. Typically, the protein complex against which an immunoreactive antibody is desired is used as the antigen for producing an immune response in a host animal. In one embodiment, the protein complex used consists of the native proteins. In another embodiment, the protein complex antigen is formed by cyclophilin C protein, or fragment thereof, and PN7718 protein, or fragment thereof. Preferably, the protein complex includes only the interacting binding domains of PN7718 and its interactor. As a result, a greater portion of the total antibodies may be selectively immunoreactive with the protein complexes of the present invention. The interacting binding domains can be selected from, e.g., those summarized in Table 1. In addition, various techniques known in the art for predicting epitopes may also be employed to design immunogenic peptides based on the interacting protein members in a protein complex of the present invention to increase the efficiency of producing an antibody selectively immunoreactive with the protein complex. Suitable epitope-prediction computer programs include, e.g., MacVector from International Biotechnologies, Inc. and Protean from DNAStar.

For purposes of preparing antibodies against the PN7718 protein, the complete PN7718 protein or fragments thereof as provided by the present invention may be used to immunize a host animal. In specific embodiments, the PN7718 fragments contain immunogenic or antigenic epitopes. Such epitopes can be readily determined by computer programs such as MacVector from International Biotechnologies, Inc. and Protean from DNAStar. In addition, epitopes can also be selected experimentally by any methods known in the art, e.g., in U.S. Pat. Nos. 4,833,092 and 5,194,392, both of which are incorporated herein by reference.

In another embodiment, a hybrid protein as described above in Section 5 is used as an antigen which has PN7718 or a homologues, derivative, or fragment thereof covalently linked by a peptide bond or a peptide linker to an interactor of PN7718. In a specific embodiment, the interactor is cyclophilin C or a homologue, derivative, or fragment thereof. In a preferred embodiment, the hybrid protein consists of two interacting binding domains selected from Table 1, or homologues or derivatives thereof, covalently linked together by a peptide bond or a linker molecule.

The antibodies of the present invention can be polyclonal antibodies. To produce the polyclonal antibodies, various animal hosts can be employed, including, e.g., mice, rats, rabbits, goats, guinea pigs, hamsters, etc. A suitable antigen or a derivative thereof as described above can be administered directly to a host animal to illicit immune reactions. Alternatively, it can be administered together with a carrier such as keyhole limpet hemocyanin (KLH), bovine serum albumin (BSA), ovalbumin, and Tetanus toxoid. Optionally, the antigen is conjugated to a carrier by a coupling agent such as carbodiimide, glutaraldehyde, and MBS. Any conventional adjuvants may be used to boost the immune response of the host animal to the antigen used. Suitable adjuvants known in the art include but are not limited to Complete Freund's Adjuvant (which contains killed mycobacterial cells and mineral oil), incomplete Freund's Adjuvant (which lacks the cellular components), aluminum salts, MF59 from Chiron (Emeryville, Calif.), monophospholipid, synthetic trehalose dicorynomycolate (TDM) and cell wall skeleton (CWS) both from Corixa Corp. (Seattle, Wash.), non-ionic surfactant vesicles (NISV) from *Proteus* International PLC (Cheshire, U.K.), and saponins. The antigen preparation can be administered to a host animal by subcutaneous, intramuscular, intravenous, intradermal, or intraperitoneal injection, or by injection into a lymphoid organ.

The antibodies of the present invention may also be monoclonal. Such monoclonal antibodies may be developed using any conventional techniques known in the art. For example, the popular hybridoma method disclosed in Kohler and Milstein, *Nature,* 256:495–497 (1975) is now a well-developed technique that can be used in the present invention. See U.S. Pat. No. 4,376,110, which is incorporated herein by reference. Essentially, B-lymphocytes producing a polyclonal antibody against PN7718 or a protein complex of the present invention can be fused with myeloma cells to generate a library of hybridoma clones. The hybridoma population is then screened for antigen binding specificity and also for immunoglobulin class (isotype). In this manner, pure hybridoma clones producing specific homogenous antibodies can be selected. See generally, Harlow and Lane, *Antibodies: A Laboratory Manual,* Cold Spring Harbor Press, 1988. Alternatively, other techniques known in the art may also be used to prepare monoclonal antibodies, which include but are not limited to the EBV hybridoma technique, the human N-cell hybridoma technique, and the trioma technique.

In addition, the antibodies of the present invention may also be recombinantly produced. For example, cDNAs prepared by PCR amplification from activated B-lymphocytes or hybridomas may be cloned into an expression vector to form a cDNA library, which is then introduced into a host cell for recombinant expression. The cDNA encoding a specific desired protein may then be isolated from the library. The isolated cDNA can be introduced into a suitable host cell for the expression of the protein. Thus, recombinant techniques can be used to recombinantly produce specific native antibodies, hybrid antibodies capable of simultaneous reaction with more than one antigen, chimeric antibodies (e.g., the constant and variable regions are derived from different sources), univalent antibodies which comprise one heavy and light chain pair coupled with the Fc region of a third (heavy) chain, Fab proteins, and the like. See U.S. Pat. No. 4,816,567; European Patent Publication No. 0088994; Munro, *Nature,* 312:597 (1984); Morrison, *Science,* 229: 1202 (1985); Oi et al., *BioTechniques,* 4:214 (1986); and Wood et al., *Nature,* 314:446–449 (1985), all of which are incorporated herein by reference. Antibody fragments such as Fv fragments, single-chain Fv fragments (scFv), Fab' fragments, and F(ab')$_2$ fragments can also be recombinantly produced by methods disclosed in, e.g., U.S. Pat. No. 4,946,778; Skerra & Plückthun, *Science,* 240:1038–1041 (1988); Better et al., *Science,* 240:1041–1043 (1988); and Bird, et al., *Science,* 242:423–426 (1988), all of which are incorporated herein by reference. Recombinant antibodies can be expressed in various host cells including bacteria, yeast, plant cells, insect cells, animal cells, preferably in mammalian cells. Alternatively, recombinant antibodies can be produced in transgenic plants (e.g., crop plants) or in transgenic animals (e.g., transgenic goats and transgenic chickens).

In a preferred embodiment, the antibodies provided in accordance with the present invention are partially or fully humanized antibodies. For this purpose, any methods known in the art may be used. For example, partially humanized chimeric antibodies having V regions derived from the tumor-specific mouse monoclonal antibody, but human C regions are disclosed in Morrison and Oi, *Adv. Immunol.,* 44:65–92 (1989). In addition, fully humanized antibodies can be made using transgenic non-human animals. For example, transgenic non-human animals such as transgenic mice can be produced in which endogenous immunoglobulin genes are suppressed or deleted, while heterologous antibodies are encoded entirely by exogenous immunoglobulin genes, preferably human immunoglobulin genes, recombinantly introduced into the genome. See e.g., U.S. Pat. Nos. 5,530,101; 5,545,806; 6,075,181; PCT Publication No. WO 94/02602; Green et. al., *Nat. Genetics,* 7: 13–21 (1994); and Lonberg et al., *Nature* 368: 856–859 (1994), all of which are incorporated herein by reference. The transgenic non-human host animal may be immunized with suitable antigens such as a protein complex of the present invention or one or more of the interacting protein members thereof to illicit specific immune response thus producing humanized antibodies. In addition, cell lines producing specific humanized antibodies can also be derived from the immunized transgenic non-human animals. For example, mature B-lymphocytes obtained from a transgenic animal producing humanized antibodies can be fused to myeloma cells and the resulting hybridoma clones may be selected for specific humanized antibodies with desired binding specificities. Alternatively, cDNAs may be extracted from mature B-lymphocytes and used in establishing a library which is subsequently screened for clones encoding humanized antibodies with desired binding specificities.

In yet another embodiment, a bifunctional antibody is provided which has two different antigen binding sites, each being specific to a different interacting protein member in a protein complex of the present invention. In a specific embodiment, a bifunctional antibody is provided which is immunoreactive with both cyclophilin C and PN7718. The bifunctional antibody may be produced using a variety of methods known in the art. For example, two different monoclonal antibody-producing hybridomas can be fused together. One of the two hybridomas may produce a monoclonal antibody specific against an interacting protein member of a protein complex of the present invention, while the other hybridoma generates a monoclonal antibody immunoreactive with another interacting protein member of the protein complex. The thus formed new hybridoma produces different antibodies including a desired bifunctional antibody, i.e., an antibody immunoreactive with both of the interacting protein members. The bifunctional antibody can be readily purified. See Milstein and Cuello, *Nature,* 305: 537–540 (1983).

Alternatively, a bifunctional antibody may also be produced using heterobifunctional crosslinkers to chemically link two different monoclonal antibodies, each being immunoreactive with a different interacting protein member of a protein complex. Therefore, the aggregate will bind to two interacting protein members of the protein complex. See Staerz et al, *Nature,* 314:628–631(1985); Perez et al, *Nature,* 316:354–356 (1985).

In addition, bifunctional antibodies can also be produced by recombinantly expressing light and heavy chain genes in a hybridoma that itself produces a monoclonal antibody. As a result, a mixture of antibodies including a bifunctional antibody is produced. See DeMonte et al, *Proc. Natl. Acad. Sci., USA,* 87:2941–2945 (1990); Lenz and Weidle, *Gene,* 87:213–218 (1990).

Preferably, a bifunctional antibody in accordance with the present invention is produced by the method disclosed in U.S. Pat. No. 5,582,996, which is incorporated herein by reference. For example, two different Fabs can be provided and mixed together. The first Fab can bind to an interacting protein member of a protein complex, and has a heavy chain constant region having a first complementary domain not naturally present in the Fab but capable of binding a second complementary domain. The second Fab is capable of binding another interacting protein member of the protein complex, and has a heavy chain constant region comprising a second complementary domain not naturally present in the Fab but capable of binding to the first complementary domain. Each of the two complementary domains is capable of stably binding to the other but not to itself. For example, the leucine zipper regions of c-fos and c-jun onco-proteins may be used as the first and second complementary domains. As a result, the first and second complementary domains interact with each other to form a leucine zipper thus associating the two different Fabs into a single antibody capable of binding to two antigenic sites.

Other suitable methods known in the art for producing bifunctional antibodies may also be used, which include those disclosed in Holliger et al., *Proc. Nat'l Acad. Sci. USA,* 90:6444–6448 (1993); de Kruif et al., *J. Biol. Chem.,* 271:7630–7634 (1996); Coloma and Morrison, *Nat. Biotechnol.,* 15:159–163 (1997); Muller et al., *FEBS Lett.,* 422:259–264 (1998); and Muller et al., *FEBS Lett.,* 432: 45–49 (1998), all of which are incorporated herein by reference.

8. Protein Microchips

In accordance with another embodiment of the present invention, a protein microchip or microarray is provided having (1) the PN7718 protein or homologue or fragment thereof, (2) one or more of the protein complexes of the present invention, (3) an antibody immunoreactive with the PN7718 protein or a homologue thereof, or (4) an antibody immunoreactive with a PN7718-containing protein complex of the present invention.

Protein microarrays are becoming increasingly important in both proteomics research and protein-based detection and diagnosis of diseases. The protein microarrays, in accordance with the present invention, will be useful in a variety of applications including, e.g., high throughput screening for compounds capable of binding PN7718 protein or PN7718-containing protein complexes, or compounds capable of modulating the activities of PN7718 protein or PN7718-containing protein complexes. The protein microarrays are also useful in detecting the PN7718 protein or the PN7718-containing protein complexes, and thus can be used in applications such as tissue typing, disease prediction, diagnosis and prognosis.

The protein microarray of the present invention can be prepared by a number of methods known in the art. An example of a suitable method is that disclosed in MacBeath and Schreiber, *Science,* 289:1760–1763 (2000). Essentially, glass microscope slides are treated with an aldehyde-containing silane reagent (SuperAldehyde Substrates purchased from TeleChem International, Cupertino, Calif.). Nanoliter volumes of protein samples in a phosphate-buffered saline with 40% glycerol are then spotted onto the treated slides using a high-precision contact-printing robot. After incubation, the slides are immersed in a bovine serum albumin (BSA)-containing buffer to quench the unreacted aldehydes and to form a BSA layer, which functions to prevent non-specific protein binding in subsequent applications of the microchip. Alternatively, as disclosed in MacBeath and Schreiber, proteins or protein complexes of the present invention can be attached to a BSA-NHS slide by covalent linkages. BSA-NHS slides are fabricated by first attaching a molecular layer of BSA to the surface of glass slides and then activating the BSA with N,N'-disuccinimidyl carbonate. As a result, the amino groups of the lysine, asparate, and glutamate residues on the BSA are activated and can form covalent urea or amide linkages with protein samples spotted on the slides. See MacBeath and Schreiber, *Science,* 289:1760–1763 (2000).

Another example of useful method for preparing the protein microchip of the present invention is that disclosed in PCT Publication Nos. WO 00/4389A2 and WO 00/04382, both of which are assigned to Zyomyx and are incorporated herein by reference. First, a substrate or chip base is covered with one or more layers of thin organic film to eliminate any surface defects, insulate proteins from the base materials, and to ensure a uniform protein array. Next, a plurality of protein-capturing agents (e.g., antibodies, peptides, etc.) are arrayed and attached to the base that is covered with the thin film. Proteins or protein complexes can then be bound to the capturing agents forming a protein microarray. The protein microchips are kept in flow chambers with an aqueous solution.

The protein microarray of the present invention can also be made by the method disclosed in PCT Publication No. WO 99/36576 assigned to Packard Bioscience Company, which is incorporated herein by reference. For example, a three-dimensional hydrophilic polymer matrix, i.e., a gel, is first deposited on a solid substrate such as a glass slide. The polymer matrix gel is capable of expanding or contracting and contains a coupling reagent that reacts with amine groups. Thus, proteins and protein complexes can be contacted with the matrix gel in an expanded aqueous and porous state to allow reactions between the amine groups on the protein or protein complexes with the coupling reagents thus immobilizing the proteins and protein complexes on the substrate. Thereafter, the gel is contracted to embed the attached proteins and protein complexes in the matrix gel.

Alternatively, the proteins and protein complexes of the present invention can be incorporated into a commercially available protein microchip, e.g., the ProteinChip System from Ciphergen Biosystems Inc., Palo Alto, Calif. The ProteinChip System comprises metal chips having a treated surface that interact with proteins. Basically, a metal chip surface is coated with a silicon dioxide film. The molecules of interest such as proteins and protein complexes can then be attached covalently to the chip surface via a silane coupling agent.

The protein microchips of the present invention can also be prepared with other methods known in the art, e.g., those disclosed in U.S. Pat. Nos. 6,087,102, 6,139,831, 6,087,103; PCT Publication Nos. WO 99/60156, WO 99/39210, WO 00/54046, WO 00/53625, WO 99/51773, WO 99/35289, WO 97/42507, WO 01/01142, WO 00/63694, WO 00/61806, WO 99/61148, WO 99/40434, all of which are incorporated herein by reference.

9. Methods of Detection and Diagnosis

Another aspect of the present invention relates to detecting PN7718 and the protein complexes of the present invention.

In one embodiment, methods are provided for detecting PN7718 nucleic acids in a sample. The method may be employed to detect the level or localization of PN7718 nucleic acids in cell, tissue or organ samples. Any techniques known in the art for detecting nucleic acids can be used. For example, the various nucleic acid molecules provided in Section 2 may be used as probes in hybridization assays to detect PN7718 nucleic acids. Various hybridization techniques may be used for this purpose including, but not limited to, Northern blot, Southern blot, dot blot, hybridization on a microarray, etc. The PN7718 nucleic acid molecules can be isolated from a sample, or alternatively detected directly in situ (e.g., by fluorescence in situ hybridization or FISH). If necessary, the PN7718 nucleic acids in a sample may be amplified by any suitable techniques known in the art, e.g., polymerase chain reaction (PCR), ligation chain reaction (LCR), etc. For determining the level of the PN7718 nucleic acids (e.g. mRNA level), quantitative PCR may preferably be used. Given the PN7718 nucleotide sequence of SEQ ID NO:1, methods for designing probes and primers for use in the detection procedures would be apparent to skilled artisans.

The present invention also provides methods for genotyping the PN7718 nucleic acids in a sample to determine any polymorphisms (e.g. SNPs, MTRs, RFLPs, etc.) or mutations (e.g., deletions, insertions, large rearrangements, etc.). Various methods known in the art for detecting polymorphisms or mutations can be used for genotyping. For example, the PN7718 mRNA transcripts can be isolated from a sample and reverse transcribed into cDNAs, which can then be sequenced by standard sequencing techniques. Polymorphisms and mutations can be readily uncovered by comparing the PN7718 sequences from two or more samples from different sources. For purposes of identifying polymorphisms, preferably a large number of samples from different individuals of a population are analyzed. Once the loci of potential polymorphisms are identified, various techniques may be employed to determine the polymorphic variant in the PN7718 nucleic acid of a particular sample. Suitable techniques known in the art include, but are not limited to, direct sequencing, single-stranded conformation polymorphism assay (SSCA) (See Orita et al., *Proc. Natl. Acad. Sci. USA*, 86:2776–2770 (1989)), clamped denaturing gel electrophoresis (CDGE) and denaturing gradient gel electrophoresis (DGGE) (See e.g., Sheffield et al., *Proc. Natl. Acad. Sci. USA*, 86:232–236 (1989)), amplification refractory mutation system (ARMS) (See e.g., European Patent No. 0,332,435), single nucleotide primer extension (See Syvanen et al., *Genomics*, 8:684–692 (1990)), oligonucleotide ligation assay (OLA) (See e.g., Landergren et al., *Science*, 241:1077–1080 (1988)), allele-specific oligonucleotides hybridization (see Conner et al., *Proc. Natl. Acad. Sci. USA*, 80:278–282 (1983); Saiki et al, *Proc. Natl. Acad. Sci. USA*, 86:6230–6234 (1989)), mutS assays (See Modrich et al., *Ann. Rev. Genet.*, 25:229–253 (1991)), and the like. Additionally, the Invader assay and the rolling circle amplification technique may also be used. See e.g. Lyamichev et al., *Nat. Biotechnol.*, 17:292–296 (1999); Lizardi et al., *Nature Genetics*, 19:225–232 (1998).

The present invention also encompasses methods for detecting the PN7718 protein or fragments thereof. Conveniently, the PN7718 protein in a sample may be detected by contacting the sample with an antibody immunoreactive with the PN7718 protein, using the various antibody-based assays known in the art. Examples of suitable immunoassays include, but are not limited to, immunocytochemical methods, enzyme-linked immunosorbent assay (ELISA), radioimmunoassay (RIA), immunoradiometric assays (IRMA), fluorescent immunoassays, protein A immunoassays, and immunoenzymatic assays (IEMA). See e.g., U.S. Pat. Nos. 4,376,110 and 4,486,530, both of which are incorporated herein by reference. For such immunoassays, the anti-PN7718 antibodies of the present invention as provided in Section 7 can be used.

The present invention also relates to methods for detecting a PN7718-containing protein complex in a sample. In a specific embodiment, the protein complex comprises PN7718 and cyclophilin C. For example, the protein complex can be isolated or purified from a sample of a patient's cells, tissues, or organs, and the amount of protein complex can be determined. As described above, the protein complex can be prepared from a cell, tissue or organ sample by coimmunoprecipitation using an antibody immunoreactive with an interacting protein member, a bifunctional antibody that is immunoreactive with two or more interacting protein members of the protein complex, or preferably an antibody selectively immunoreactive with the protein complex. When bifunctional antibodies or antibodies immunoreactive with only free protein members are used, individual interacting protein members not complexed with other proteins may also be isolated along with the protein complex containing such individual proteins. However, they can be readily separated from the protein complex using methods known in the art, e.g., size-based separation methods such as gel filtration, or by subtracting the protein complex from the mixture using an antibody specific against another individual interacting protein member. Additionally, proteins in a sample can be separated in a gel such as polyacrylamide gel and subsequently immunoblotted using an antibody immunoreactive with the protein complex.

Alternatively, the level of the protein complex can be determined in a sample without separation, isolation or purification. For this purpose, it is preferred that an antibody selectively immunoreactive with the specific protein complex is used in an immunoassay. For example, immunocytochemical methods can be used. Other well known antibody-based techniques can also be used including, e.g., enzyme-linked immunosorbent assay (ELISA), radioimmunoassay (RIA), immunoradiometric assays (IRMA), fluorescent immunoassays, protein A immunoassays, and immunoenzymatic assays (IEMA). See e.g., U.S. Pat. Nos. 4,376, 110 and 4,486,530, both of which are incorporated herein by reference.

In addition, since a specific protein complex is formed from its interacting protein members, if one of the interacting protein members is at a relatively low level in a patient, it may be reasonably expected that the level of the protein complex in the patient may also be low. Therefore, the level of an individual interacting protein member of a specific protein complex can be determined in a patient sample, which can be used as a reasonably accurate indicator of the level of the protein complex in the sample. For this purpose, antibodies against an individual interacting protein member of a specific complex can be used in any one of the methods described above. In a preferred embodiment, the level of each of the interacting protein members of a protein complex is determined in a patient sample, and the relative level of the protein complex is then deduced.

In addition, the relative protein complex level in a patient can also be determined by measuring the level of the mRNA encoding an interacting protein member of the protein complex. Preferably, each interacting protein member's mRNA level in a patient sample is determined. For this purpose, methods for determining mRNA level generally known in the art may all be used. Examples of such methods include, e.g., Northern blot assay, dot blot assay, PCR assay (preferably quantitative PCR assay), in situ hybridization assay, and the like.

As discussed above, the interaction between cyclophilin C and PN7718 suggests that these proteins and/or the protein complexes formed by such proteins may be involved in common biological processes and disease pathways. In addition, the interactions between cyclophilin C and PN7718 under physiological conditions may result in the formation of protein complexes in vivo, which contain cyclophilin C and PN7718. The protein complexes may mediate the functions and biological activities of cyclophilin C and PN7718. For example, cyclophilin C and PN7718 may be involved in intracellular calcium signaling, beta-amyloid formation, T-cell receptor and IgE receptor signaling pathways, and protein folding and degradation and associated with diseases and disorders such as autoimmune diseases, neurological diseases and cardiovascular disorders. Thus, aberrations in the level and/or activity of the protein complexes and/or the proteins such as PN7718 and PN7718-interacting proteins (e.g. cyclophilin C) may result in diseases or disorders such as autoimmune diseases, neurological diseases and cardiovascular disorders. Thus, the aberration in the protein complexes or the individual proteins and the degree of the aberration may be indicators for the diseases or disorders. They may be used as parameters for classifying and/or staging one of the above-described diseases. In addition, they may also be indicators for patients' response to drug therapy.

Association between a physiological state (e.g., physiological disorder, predisposition to the disorder, a disease state, response to a drug therapy, or other physiological phenomena or phenotypes) and a specific aberration in a protein complex of the present invention or an individual interacting member thereof can be readily determined by comparative analysis of the protein complex and/or the interacting members thereof in a normal population and an abnormal or affected population. Thus, for example, one can study the level, localization and distribution of a particular protein complex, mutations in the interacting protein members of the protein complex, and/or the binding affinity between the interacting protein members in both a normal population and a population affected with a particular physiological disorder described above. The study results can be compared and analyzed by statistical means. Any detected statistically significant difference in the two populations would indicate an association. For example, if the level of the protein complex is statistically significantly higher in the affected population than in the normal population, then it can be reasonably concluded that a higher level of the protein complex is associated with the physiological disorder. Likewise, an association between PN7718 and a particular disorder may also be detected.

Thus, once an association is established between a particular type of aberration in PN7718 or a particular PN7718-containing protein complex and a physiological disorder or disease, or predisposition to the physiological disorder or disease, then the particular physiological disorder or disease, or predisposition to the physiological disorder or disease can be diagnosed or detected by determining whether a patient has the particular aberration.

Accordingly, the present invention also provides a method for diagnosing a disease or physiological disorder, or a predisposition to the disease or disorder such as autoimmune diseases, neurological diseases and cardiovascular disorders in a patient by determining whether there is any aberration in the patient with respect to PN7718 and/or a PN7718-containing protein complex. As used herein, the term "aberration" means any alterations of PN7718 or a PN7718-containing protein complex including increased or decreased level of the PN7718 protein or PN7718-containing protein complex in a particular cell or tissue or organ or the total body, altered localization of the PN7718 protein or PN7718-containing protein complex in cellular compartments or in locations of a tissue or organ, changes in binding affinity of a PN7718 protein to its protein interactor, mutations in PN7718 protein or an interacting protein thereof or the gene encoding the proteins, and the like. As will be apparent to a skilled artisan, the term "aberration" is used in a relative sense. That is, an aberration is relative to a normal individual.

As used herein, the term "diagnosis" means detecting a disease or disorder or determining the stage or degree of a disease or disorder. The term "diagnosis" also encompasses detecting a predisposition to a disease or disorder, determining the therapeutic effect of a drug therapy, or predicting the pattern of response to a drug therapy or xenobiotics. The diagnosis methods of the present invention may be used independently, or in combination with other diagnosing and/or staging methods known in the medical art for a particular disease or disorder.

Thus, in one embodiment, the method of diagnosis is conducted by detecting, in a patient, the levels of one or more protein complexes of the present invention using any one of the methods described above, and determining whether the patient has an aberrant level of the protein complexes.

The diagnosis may also be based on the determination of the levels of one or more interacting protein members (at either the protein or mRNA level) of a protein complex of the present invention. An aberrant level of an interacting protein member may indicate a physiological disorder or a predisposition to a physiological disorder. In a specific embodiment, the levels of PN7718 and/or cyclophilin C are determined.

In another embodiment, the method of diagnosis comprises determining, in a patient, the cellular localization, or tissue or organ distribution of a protein complex of the present invention and determining whether the patient has an aberrant localization or distribution of the protein complex. For example, immunocytochemical or immunohistochemical assays can be performed on a cell, tissue or organ sample from a patient using an antibody selectively immunoreactive with a protein complex of the present invention. Antibodies immunoreactive with both an individual interacting protein member and a protein complex containing the protein member may also be used, in which case it is preferred that antibodies immunoreactive with other interacting protein members are also used in the assay. In addition, nucleic acid probes may also be used in in situ hybridization assays to detect the localization or distribution of the mRNAs encoding the interacting protein members of a protein complex. Preferably, the mRNA encoding each interacting protein member of a protein complex is detected concurrently.

In yet another embodiment, the method of diagnosis of the present invention comprises detecting any mutations in one or more interacting protein members of a protein complex of the present invention. In particular, it is desirable to determine whether the interacting protein members have any mutations that will lead to, or are in disequilibrium with, changes in the activity of the proteins or changes in their binding affinity to other interacting protein members in forming a protein complex of the present invention. Examples of such mutations include, but are not limited to, e.g., deletions, insertions and rearrangements in the genes encoding the protein members, and nucleotide or amino acid substitutions and the like. In a preferred embodiment, the binding domains of the interacting protein members responsible for the protein—protein interactions in forming a protein complex are screened to detect any mutations therein. For example, genomic DNA or cDNA encoding an interacting protein member can be prepared from a patient sample, and sequenced. The thus-obtained sequence may be compared with known reference sequences to identify any mutations. Alternatively, an interacting protein member may be purified from a patient sample and analyzed by protein sequencing or mass spectrometry to detect any amino acid sequence changes. Any methods known in the art for detecting mutations may also be used, as will be apparent to skilled artisans apprised of the present disclosure.

In another embodiment, the method of diagnosis includes determining the binding constant of a PN7718 protein to a protein interactor thereof (e.g., cyclophilin C). For example, the interacting protein members can be obtained from a patient by direct purification or by recombinant expression from genomic DNAs or cDNAs prepared from a patient sample encoding PN7718 and the protein interactor (e.g., cyclophilin C). Binding constants represent the strength of the protein—protein interaction between the two proteins in a protein complex. Thus, by measuring the binding constant, subtle aberrations in binding affinity may be detected.

A number of methods known in the art for estimating and determining binding constants in protein—protein interactions are reviewed in Phizicky and Fields, et al., *Microbiol. Rev.*, 59:94–123 (1995), which is incorporated herein by reference. For example, protein affinity chromatography may be used by first preparing columns with different concentrations of an interacting protein member, which is covalently bound to the columns. Then a preparation of an interacting protein partner is run through the column and washed with buffer. The interacting protein partner bound to the interacting protein member linked to the column is then eluted. The binding constant is then estimated based on the concentrations of the bound protein and the eluted protein. Alternatively, the method of sedimentation through gradients monitors the rate of sedimentation of a mixture of proteins through gradients of glycerol or sucrose. At concentrations above the binding constant, proteins sediment as a protein complex. Thus, the binding constant can be calculated based on the concentrations. Other suitable methods known in the art for estimating the binding constant include, but are not limited to, gel filtration column such as nonequilibrium "small-zone" gel filtration columns (See e.g., Gill et al., *J. Mol. Biol.*, 220:307–324 (1991)), the Hummel-Dreyer method of equilibrium gel filtration (See e.g., Hummel and Dreyer, *Biochim. Biophys. Acta*, 63:530–532 (1962)) and large-zone equilibrium gel filtration (See e.g., Gilbert and Kellett, *J. Biol. Chem.*, 246:6079–6086 (1971)), sedimentation equilibrium (See e.g., Rivas and Minton, *Trends Biochem.*, 18:284–287 (1993)), fluorescence methods such as fluorescence spectrum (See e.g., Otto-Bruc et al, *Biochemistry*, 32:8632–8645 (1993)) and fluorescence polarization or anisotropy with tagged molecules (See e.g., Weiel and Hershey, *Biochemistry*, 20:5859–5865 (1981)), solution equilibrium measured with immobilized binding protein (See e.g., Nelson and Long, *Biochemistry*, 30:2384–2390 (1991)), and surface plasmon resonance (See e.g., Panayotou et al., *Mol. Cell. Biol.*, 13:3567–3576 (1993)).

In another embodiment, the diagnostic methods of the present invention comprise the detection of protein—protein interactions in functional assay systems such as the yeast two-hybrid system. Accordingly, to determine the protein—protein interaction between PN7718 and a protein interactor that normally forms a protein complex in normal individuals, cDNAs encoding the interacting protein members can be isolated from a patient to be diagnosed. The cloned cDNAs or fragments thereof can be subcloned into vectors for use in yeast two-hybrid systems. Preferably a reverse yeast two-hybrid system is used such that failure of interaction between the proteins may be positively detected. The use of a yeast two-hybrid system or other systems for detecting protein—protein interactions is known in the art and is described below in Sections 4 and 10.

A kit may be used to detect PN7718 nucleic acids and proteins, and to conduct the diagnosis methods of the present invention. Typically, a kit should contain, in a carrier or compartmentalized container, reagents useful in any of the above-described embodiments of the detection or diagnosis methods. The carrier can be a container or support, in the form of, e.g., a bag, box, tube, or rack, and is optionally compartmentalized. The carrier may define an enclosed confinement for safety purposes during shipment and storage.

An example of a reagent desirable in the kit is an antibody specific to the PN7718 protein. Another example is an antibody selectively immunoreactive with a PN7718-containing protein complex of the present invention. The antibodies may be labeled with a detectable marker such as radioactive isotopes, or enzymatic or fluorescence markers. Alternatively, secondary antibodies such as labeled anti-IgG and the like may be included for detection purposes. Optionally, the kit can include one or more of the protein complexes of the present invention prepared or purified from a normal individual or an individual afflicted with a physiological disorder associated with an aberration in the protein complexes or an interacting protein member thereof. In addition, the kit may include one or more of the interacting members of the protein complexes of the present invention prepared or purified from a normal individual or an individual afflicted with a physiological disorder associated with an aberration in the protein complexes or an interacting protein member thereof. Preferably, a PN7718 protein or fragment or homologue thereof as provided in accordance with the present invention is included in the kit.

It may also be desirable to include in the kit PN7718 nucleic acids, or homologues thereof, as provided in accordance with the present invention. In a specific embodiment, the PN7718 nucleic acid is an oligonucleotide. In particular, in a preferred embodiment, the kit includes a first oligonucleotide selectively hybridizable to the mRNA or cDNA encoding cyclophilin C and a second oligonucleotide selectively hybridizable to the mRNA or cDNA encoding PN7718. Such oligos may be used as PCR primers for, e.g., quantitative PCR amplification of mRNAs, or as hybridizing probes for detecting the mRNAs. The oligonucleotides may have a length of from about 8 nucleotides to about 100 nucleotides, preferably from about 12 to about 50 nucleotides, and more preferably from about 15 to about 30 nucleotides. Preferably, instructions for using the kit or reagents contained therein are also included in the kit.

10. Screening Assays for Modulators

The PN7718 protein and the PN7718-containing protein complexes of the present invention can also be used in screening assays to select modulators of PN7718 and the protein complexes of the present invention. In addition, homologues, derivatives or fragments of PN7718 and PN7718-interacting proteins, and protein complexes containing such homologues, derivatives or fragments may also be used in the screening assays. As used herein, the term "modulator" encompasses any compounds that can cause any form of alteration of the properties or activities of the proteins or protein complexes, including but not limited to, e.g., enhancing or reducing their biological activities exhibited in biological processes or cell functions, increasing or decreasing their stability, altering their affinity or specificity to other molecules, etc. In addition, the term "modulator" as used herein also includes any compounds that simply bind PN7718 and/or the proteins complexes of the present invention. For example, a modulator can be a dissociator capable of interfering with or disrupting or dissociating protein—protein interaction between PN7718 or a homologue or derivative thereof and a PN7718-interacting protein, e.g., cyclophilin C, or a homologue or derivative thereof. A modulator can also be an enhancer or initiator that initiates or strengthens the interaction between the protein members of a protein complex of the present invention.

Accordingly, the present invention provides screening methods for selecting modulators of PN7718 or a mutant form thereof, and modulators of a PN7718-containing protein complex. In one embodiment, the PN7718 protein is used in the methods of the present invention as a target protein to select modulators of PN7718. In another embodiment, a PN7718-containing protein complex is used as a target for selecting modulators of the protein complex. In a specific embodiment, the PN7718-containing protein complex comprises PN7718 or a homologue or derivative thereof and cyclophilin C or a homologue or derivative thereof.

The selected compounds can be tested for their ability to modulate (interfere with or strengthen) the interaction between the interacting partners within the protein complexes of the present invention. In addition, the compounds can also be further tested for their ability to modulate (inhibit or enhance) cellular functions such as intracellular calcium signaling, beta-amyloid formation, T-cell receptor and IgE receptor signaling pathways, and protein folding and degradation in cells as well as their effectiveness in treating diseases such as autoimmune diseases, neurological diseases and cardiovascular disorders.

The modulators selected in accordance with the screening methods of the present invention can be effective in modulating the activities of PN7718, PN7718-interacting proteins, or the protein complexes of the present invention. For example, compounds capable of binding the protein complexes may be capable of modulating the activities of the protein complexes. Additionally, compounds that interfere with, weaken, dissociate or disrupt, or alternatively, initiate, facilitate or stabilize the protein—protein interaction between the interacting protein members of the protein complexes can also be effective in modulating the functions or activities of the protein complexes. Thus, the compounds selected in the screening methods of the present invention can be made into therapeutically or prophylactically effective drugs for preventing or ameliorating diseases, disorders or symptoms caused by or associated with PN7718 or a PN7718-containing protein complex of the present invention. Alternatively, they may be used as leads to aid the design and identification of therapeutically or prophylactically effective compounds for diseases, disorders or symptoms caused by or associated with PN7718 or a PN7718-containing protein complex of the present invention. The protein complexes and/or interacting protein members thereof in accordance with the present invention can be used in any of a variety of drug screening techniques. Drug screening can be performed as described herein or using well-known techniques, such as those described in U.S. Pat. Nos. 5,800,998 and 5,891,628, both of which are incorporated herein by reference.

10.1. Test Compounds

Any test compounds may be screened in the screening assays of the present invention to select modulators of PN7718, and/or a PN7718-containing protein complex of the present invention. The terms "selecting" or "select" modulators are intended to encompass both (a) choosing compounds from a group previously unknown to be modulators of a PN7718-containing protein complex and/or PN7718 of the present invention, and (b) testing compounds that are known to be capable of binding, or modulating the activities of a PN7718-containing protein complex and/or PN7718 of the present invention. Both types of compounds are generally referred to herein as "test compounds." The test compounds may include, by way of example, proteins (e.g., antibodies, small peptides, artificial or natural proteins), nucleic acids, and derivatives, mimetics, and analogs thereof, and small organic molecules having a molecular weight of no greater than 10,000 dalton, more preferably less than 5,000 dalton. Preferably, the test compounds are provided in library formats known in the art, e.g., in chemically synthesized libraries, recombinantly expressed libraries (e.g., phage display libraries), and in vitro translation-based libraries (e.g., ribosome display libraries).

For example, the screening assays of the present invention can be used in the antibody production processes described in Section 7 to select antibodies with desirable specificities. Various forms of antibodies or derivatives thereof may be screened, including but not limited to, polyclonal antibodies, monoclonal antibodies, bifunctional antibodies, chimeric antibodies, single chain antibodies, antibody fragments such as Fv fragments, single-chain Fv fragments (scFv), Fab' fragments, and F(ab')$_2$ fragments, and various modified forms of antibodies such as catalytic antibodies, and antibodies conjugated to toxins or drugs, and the like. The antibodies can be of any types such as IgG, IgE, IgA, or IgM. Humanized antibodies are particularly preferred. Preferably, the various antibodies and antibody fragments may be provided in libraries to allow large-scale high throughput screening. For example, expression libraries expressing antibodies or antibody fragments may be constructed by a method disclosed, e.g., in Huse et al., *Science*, 246:1275–1281 (1989), which is incorporated herein by reference. Single-chain Fv (scFv) antibodies are of particular interest in diagnostic and therapeutic applications. Methods for providing antibody libraries are also provided in U.S. Pat. Nos. 6,096,551; 5,844,093; 5,837,460; 5,789,208; and 5,667,988, all of which are incorporated herein by reference.

Peptidic test compounds may be peptides having L-amino acids and/or D-amino acids, phosphopeptides, and other types of peptides. The screened peptides can be of any size, but preferably have less than about 50 amino acids. Smaller peptides are easier to deliver into a patient's body. Various forms of modified peptides may also be screened. Like antibodies, peptides can also be provided in, e.g., combinatorial libraries. See generally, Gallop et al., *J. Med. Chem.*, 37:1233–1251 (1994). Methods for making random peptide libraries are disclosed in, e.g., Devlin et al., *Science*, 249: 404–406 (1990). Other suitable methods for constructing peptide libraries and screening peptides therefrom are disclosed in, e.g., Scott and Smith, *Science*, 249:386–390 (1990); Moran et al., *J. Am. Chem. Soc.*, 117:10787–10788 (1995) (a library of electronically tagged synthetic peptides); Stachelhaus et al., *Science*, 269:69–72 (1995); U.S. Pat. Nos. 6,156,511; 6,107,059; 6,015,561; 5,750,344; 5,834,318; 5,750,344, all of which are incorporated herein by reference. For example, random-sequence peptide phage display libraries may be generated by cloning synthetic oligonucleotides into the gene III or gene VIII of an *E. coli.* filamentous phage. The thus-generated phage can propagate in *E. coli.* and express peptides encoded by the oligonucleotides as fusion proteins on the surface of the phage. Scott and Smith, *Science*, 249:368–390 (1990). Alternatively, the "peptides on plasmids" method may also be used to form peptide libraries. In this method, random peptides may be fused to the C-terminus of the *E. coli.* Lac repressor by recombinant technologies and expressed from a plasmid that also contains Lac repressor-binding sites. As a result, the peptide fusions bind to the same plasmid that encodes them.

Small organic or inorganic non-peptide non-nucleotide compounds are preferred test compounds for the screening assays of the present invention. They too can be provided in a library format. See generally, Gordan et al. *J. Med. Chem.*, 37:1385–1401 (1994). For example, benzodiazepine libraries are provided in Bunin and Ellman, *J. Am. Chem. Soc.*, 114:10997–10998 (1992), which is incorporated herein by reference. Methods for constructing and screening peptoid libraries are disclosed in Simon et al., *Proc. Natl. Acad. Sci. USA*, 89:9367–9371 (1992). Methods for the biosynthesis of novel polyketides in a library format are described in McDaniel et al, *Science*, 262:1546–1550 (1993) and Kao et al., *Science*, 265:509–512 (1994). Various libraries of small organic molecules and methods of construction thereof are disclosed in U.S. Pat. No. 6,162,926 (multiply-substituted fullerene derivatives); U.S. Pat. No. 6,093,798 (hydroxamic acid derivatives); U.S. Pat. No. 5,962,337 (combinatorial 1,4-benzodiazepin-2,5-dione library); U.S. Pat. No. 5,877,278 (synthesis of N-substituted oligomers); U.S. Pat. No. 5,866,341 (compositions and methods for screening drug libraries); U.S. Pat. No. 5,792,821 (polymerizable cyclodextrin derivatives); U.S. Pat. No. 5,766,963 (hydroxypropylamine library); and U.S. Pat. No. 5,698,685 (morpholino-subunit combinatorial library), all of which are incorporated herein by reference.

Other compounds such as oligonucleotides and peptide nucleic acids (PNA), and analogs and derivatives thereof may also be screened to identify clinically useful compounds. Combinatorial libraries of oligos are also known in the art. See Gold et al., *J. Biol. Chem.*, 270:13581–13584 (1995).

10.2. In Vitro Assays

The test compounds may be screened in an in vitro assay to identify compounds capable of binding PN7718 or a PN7718-containing protein complex. For this purpose, a test compound can be contacted with a protein complex or an interacting protein member thereof (e.g., PN7718 or a homologue or derivative thereof) under conditions and for a time sufficient to allow specific interactions between the test compound and the target components to occur, thereby resulting in the binding of the compound to the target, and the formation of a complex. Subsequently, the binding event is detected.

Various screening techniques known in the art may be used in the present invention. The protein complexes and the interacting protein members thereof may be prepared by any suitable methods, e.g., by recombinant expression and purification. The protein complexes and/or interacting protein members thereof (both are referred to as "target" hereinafter in this section) may be free in solution. A test compound may be mixed with a target forming a liquid mixture. The compound may be labeled with a detectable marker. Upon mixing under suitable conditions, the binding complex having the compound and the target may be co-immunoprecipitated and washed. The compound in the precipitated complex may be detected based on the marker on the compound.

In a preferred embodiment, the target is immobilized on a solid support or on a cell surface. Preferably, the target can be arrayed into a protein microchip in a method described in Section 8. For example, a target may be immobilized directly onto a microchip substrate such as glass slides or onto multi-well plates using non-neutralizing antibodies, i.e., antibodies that are capable of binding to the target but do not substantially affect its biological activities. To affect the screening, test compounds can be contacted with the immobilized target to allow binding to occur, forming complexes under standard binding assay conditions. Either the targets or test compounds are labeled with a detectable marker using well-known labeling techniques. For example, U.S. Pat. No. 5,741,713 discloses combinatorial libraries of biochemical compounds labeled with NMR active isotopes. To identify binding compounds, one may measure the formation of the target-test compound complexes or kinetics for the formation thereof. When combinatorial libraries of organic non-peptide non-nucleic acid compounds are screened, it is preferred that labeled or encoded (or "tagged") combinatorial libraries are used to allow rapid decoding of lead compounds. This is especially important because, unlike biological libraries, individual compounds found in chemical libraries cannot be amplified by self-replication. Tagged combinatorial libraries are disclosed in, e.g., Borchardt and Still, *J. Am. Chem. Soc.*, 116:373–374 (1994) and Moran et al., *J. Am. Chem. Soc.*, 117:10787–10788 (1995), both of which are incorporated herein by reference.

Alternatively, the test compounds can be immobilized on a solid support, e.g., forming a microarray of test compounds. The target protein or protein complex is then contacted with the test compounds. The target may be labeled with any suitable detection marker. For example, the target may be labeled with radioactive isotopes or fluorescence marker before binding reaction occurs. Alternatively, after the binding reactions, antibodies that are immunoreactive with the target and are labeled with radioactive materials, fluorescence markers, enzymes, or labeled secondary anti-Ig antibodies may be used to detect any bound target thus identifying the binding compound. One example of this embodiment is the protein probing method. That is, the target provided in accordance with the present invention is used as a probe to screen expression libraries of proteins or random peptides. The expression libraries can be phage display libraries, in vitro translation-based libraries, or ordinary expression cDNA libraries. The libraries may be immobilized on a solid support such as nitrocellulose filters. See e.g., Sikela and Hahn, *Proc. Natl. Acad. Sci. USA*, 84:3038–3042 (1987). The probe may be labeled by a radioactive isotope or a fluorescence marker. Alternatively, the probe can be biotinylated and detected with a streptavidin-alkaline phosphatase conjugate. More conveniently, the bound probe may be detected with an antibody.

In yet another embodiment, a known ligand capable of binding to the target can be used in competitive binding assays. Complexes between the known ligand and the target can be formed and then contacted with test compounds. Alternatively, the known ligand can be contacted with the target in the presence of test compounds. The ability of a test compound to interfere with the interaction between the target and the known ligand is measured. One exemplary ligand is an antibody capable of specifically binding the target, which is especially useful for identifying peptides that share one or more antigenic determinants of the target protein complex or interacting protein members thereof.

In one embodiment, the PN7718 protein is used as target in the assay to select modulators of PN7718. In another embodiment, a PN7718-containing protein complex is used as a target in the assay. Preferably a protein complex formed by the PN7718 protein and the cyclophilin C protein is used in the assay. In a specific embodiment, a protein complex used in the screening assay includes a hybrid protein as described in Section 5, which is formed by fusion of two interacting protein members or fragments or domains thereof. The hybrid protein may also be designed such that it contains a detectable epitope tag fused thereto. Suitable examples of such epitope tags include sequences derived from, e.g., influenza virus hemagglutinin (HA), Simian Virus 5 (V5), polyhistidine (6×His), c-myc, lacZ, GST, and the like.

Test compounds may also be screened in an in vitro assay to identify compounds capable of dissociating the protein complexes identified in accordance with the present invention. Thus, for example, a PN7718-containing protein complex can be contacted with a test compound and the protein complex can be detected. Conversely, test compounds may also be screened to identify compounds capable of enhancing the interaction between cyclophilin C and PN7718 or stabilizing the protein complex formed by the two proteins. The assay can be conducted in similar manners as the binding assays described above. For example, the presence or absence of a particular protein complex can be detected by an antibody selectively immunoreactive with the protein complex. Thus, after the incubation of a protein complex with a test compound, immunoprecipitation assay can be conducted with the antibody. If the test compound disrupts the protein—protein interaction in the protein complex, then the amount of immunoprecipitated protein complex in this assay will be significantly less than that in a control assay in which the same protein complex is not contacted with the test compound. In another example, a protein complex formed by cyclophilin C and PN7718 is immobilized on a solid support. The immobilized protein complex is then contacted with a test compound. If the test compound dissociates the protein complex, free cyclophilin C or PN7718 may be increased and can be detected by an antibody specific to cyclophilin C or PN7718.

Similarly, two interacting proteins may be incubated together with a test compound. Thereafter, the protein complex formed by the two interacting proteins may be detected by an antibody selectively immunoreactive with the protein complex to determine whether the compound enhances interaction of the proteins, relative to the absence of the compound. Various other detection methods may be suitable in the dissociation assay, as will be apparent to a skilled artisan apprised of the present disclosure.

10.3. In Vivo Screening Assay

Test compounds can also be screened in in vivo assays to select modulators of the protein complexes or interacting protein members thereof (e.g., PN7718 or an interactor thereof) in accordance with the present invention. For this purpose, any in vivo assays known in the art useful in identifying compounds capable of strengthening or interfering with the stability of the protein complexes of the present invention may be used.

To screen peptidic compounds for modulators of PN7718, the two-hybrid systems described in Section 4 may be used in the screening assays in which the PN7718 protein is expressed in, e.g., a bait fusion protein and the peptidic test compounds are expressed in, e.g., prey fusion proteins.

To screen for modulators of the protein—protein interaction between PN7718 and a PN7718-interacting protein, the methods of the present invention typically comprise contacting the PN7718 protein with the PN7718-interacting protein in the presence of a test compound, and determining the interaction between the PN7718 protein and the PN7718-interacting protein. In a preferred embodiment, a two-hybrid system, e.g., a yeast two-hybrid system as described in detail in Section 4 is employed.

10.3.1. Screening Assay for Interaction Antagonists

The screening assay of the present invention is useful in identifying compounds capable of interfering with or disrupting or dissociating protein—protein interactions between PN7718 or a homologue or derivative thereof and a PN7718 interacting protein or a homologue or derivative thereof. For example, PN7718, cyclophilin C, and interacting proteins thereof may play roles in intracellular calcium signaling, beta-amyloid formation, T-cell receptor and IgE receptor signaling pathways, and protein folding and degradation, and may be involved in autoimmune diseases, neurological diseases and cardiovascular disorders. It may be possible to modulate intracellular calcium signaling, beta-amyloid formation, T-cell receptor and IgE receptor signaling pathways, and protein folding and degradation, and/or ameliorate or alleviate the diseases or disorders in a patient by interfering with or dissociating normal interactions between PN7718 and interacting proteins thereof (e.g., cyclophilin C). Alternatively, if the disease or disorder is associated with increased expression of PN7718 and/or cyclophilin C in accordance with the present invention, then the disease may be treated or prevented by weakening or dissociating the interaction between cyclophilin C and PN7718 in a patient. In addition, if a disease or disorder is associated with mutant forms of cyclophilin C and/or PN7718 that lead to strengthened protein—protein interaction therebetween, then the disease or disorder may be treated with a compound that weakens or interferes with the interaction between the mutant forms of cyclophilin C and PN7718.

For example, to screen for dissociators of protein— protein interactions between PN7718 and cyclophilin C, the PN7718 and cyclophilin C proteins or homologues or derivatives thereof may be used as test proteins expressed in the form of fusion proteins as described above in Section 4 for purposes of a two-hybrid assay. In a specific embodiment, binding domains of cyclophilin C and/or PN7718 (e.g., those in Table 1) are used as test proteins. The fusion proteins are expressed in a host cell and allowed to interact with each other in the presence of one or more test compounds.

In a preferred embodiment, a counterselectable marker is used as a reporter such that a detectable signal (e.g., appearance of color or fluorescence, or cell survival) is present only when the test compound is capable of interfering with the interaction between the two test proteins. In this respect, the reporters used in various "reverse two-hybrid systems" known in the art may be employed. Reverse two-hybrid systems are disclosed in, e.g., U.S. Pat. Nos. 5,525,490; 5,733,726; 5,885,779; Vidal et al., *Proc. Natl. Acad. Sci. USA*, 93:10315–10320 (1996); and Vidal et al., *Proc. Natl. Acad. Sci. USA*, 93:10321–10326 (1996), all of which are incorporated herein by reference.

Examples of suitable counterselectable reporters useful in a yeast two-hybrid system include the URA3 gene (encoding orotidine-5'-decarboxylase, which converts 5-fluroorotic acid (5-FOA) to the toxic metabolite 5-fluorouracil), the CAN1 gene (encoding arginine permease, which transports toxic arginine analog canavanine into yeast cells), the GAL1 gene (encoding galactokinase, which catalyzes the conversion of 2-deoxygalactose to toxic 2-deoxygalactose-1-phosphate), the LYS2 gene (encoding alpha-aminoadipate reductase, which renders yeast cells unable to grow on a medium containing alpha-aminoadipate as the sole nitrogen source), the MET15 gene (encoding O-acetylhomoserine sulfhydrylase, which confers sensitivity to methyl mercury), and the CYH2 gene (encoding L29 ribosomal protein, which confers sensitivity to cycloheximide). In addition, any known cytotoxic agents including cytotoxic proteins such as the diphtheria toxin (DTA) catalytic domain can also be used as counterselectable reporters. See U.S. Pat. No. 5,733,726. DTA causes the ADP-ribosylation of elongation factor-2 and thus inhibits protein synthesis and causes cell death. Other examples of cytotoxic agents include ricin, Shiga toxin, and exotoxin A of *Pseudomonas aeruginosa*.

For example, when the URA3 gene is used as a counterselectable reporter gene, yeast cells containing a mutant URA3 gene can be used as host cells (Ura$^-$ FOA$^R$ phenotype) for the in vivo assay. Such cells lack URA3-encoded functional orotidine-5'-phosphate decarboxylase, an enzyme required for the biosynthesis of uracil. As a result, the cells are unable to grow on media lacking uracil. However, because of the absence of a wild-type orotidine-5'-phosphate decarboxylase, the yeast cells cannot convert non-toxic 5-fluoroorotic acid (5-FOA) to a toxic product, 5-fluorouracil. Thus, such yeast cells are resistant to 5-FOA and can grow on a medium containing 5-FOA. Therefore, for example, to screen for a compound capable of disrupting interaction between cyclophilin C and PN7718, cyclophilin C can be expressed as a fusion protein with a DNA-binding domain of a suitable transcription activator while PN7718 is expressed as a fusion protein with a transcription activation domain of a suitable transcription activator. In the host strain, the reporter URA3 gene may be operably linked to a promoter specifically responsive to the association of the transcription activation domain and the DNA-binding domain. After the fusion proteins are expressed in the Ura$^-$ FOA$^R$ yeast cells, an in vivo screening assay can be conducted in the presence of a test compound with the yeast cells being cultured on a medium containing uracil and 5-FOA. If the test compound does not disrupt the interaction between cyclophilin C and PN7718, active URA3 gene product, i.e., orotidine-5'-decarboxylase, which converts 5-FOA to toxic 5-fluorouracil, is expressed. As a result, the yeast cells cannot grow. On the other hand, when the test compound disrupts the interaction between cyclophilin C and PN7718, no active orotidine-5'-decarboxylase is produced in the host yeast cells. Consequently, the yeast cells will survive and grow on the 5-FOA-containing medium. Therefore, compounds capable of interfering with or dissociating the interaction between cyclophilin C and PN7718 can thus be identified based on colony formation.

As will be apparent, the screening assay of the present invention can be applied in a format appropriate for large-scale screening. For example, combinatorial technologies can be employed to construct combinatorial libraries of small organic molecules or small peptides. See generally, e.g., Kenan et al., *Trends Biochem. Sc.*, 19:57–64 (1994); Gallop et al., *J. Med. Chem.*, 37:1233–1251 (1994); Gordon et al., *J. Med. Chem.*, 37:1385–1401 (1994); Ecker et al., *Biotechnology*, 13:351–360 (1995). Such combinatorial libraries of compounds can be applied to the screening assay of the present invention to isolate specific modulators of particular protein—protein interactions. In the case of random peptide libraries, the random peptides can be co-expressed with the fusion proteins of the present invention in host cells and assayed in vivo. See e.g., Yang et al., *Nucl. Acids Res.*, 23:1152–1156 (1995). Alternatively, they can be added to the culture medium for uptake by the host cells.

Conveniently, yeast mating is used in an in vivo screening assay. For example, haploid cells of a-mating type expressing one fusion protein as described above are mated with haploid cells of alpha-mating type expressing the other fusion protein. Upon mating, the diploid cells are spread on a suitable medium to form a lawn. Drops of test compounds can be deposited onto different areas of the lawn. After culturing the lawn for an appropriate period of time, compounds capable of modulating the interaction between the particular test proteins in the fusion proteins can be identified by stimulation or inhibition of growth in the vicinity of the drops.

The screening assays of the present invention for identifying compounds capable of modulating protein—protein interactions can also be fine-tuned by various techniques to adjust the thresholds or sensitivity of the positive and negative selections. Mutations can be introduced into the reporter proteins to adjust their activities. The uptake of test compounds by the host cells can also be adjusted. For example, yeast high-uptake mutants such as the erg6 mutant strains can facilitate uptake of the test compounds. See Gaber et al., *Mol. Cell. Biol.*, 9:3447–3456 (1989). Likewise, the uptake of the selection compounds such as 5-FOA, 2-deoxygalactose, cycloheximide, alpha-aminoadipate, and the like can also be fine-tuned.

10.3.2. Screening Assay for Interaction Agonists

The screening methods of the present invention can also be used in identifying compounds that trigger or initiate, enhance or stabilize protein—protein interactions between PN7718 and an interacting protein thereof (e.g., interactions between PN7718 or a mutant thereof and cyclophilin C or a mutant thereof). For example, if the interaction between PN7718 and an interacting protein thereof contributes to the treatment of a particular disease, then modulators capable of stabilizing the protein—protein interaction may be useful in the treatment of the disease. In addition, if a disease or disorder is associated with decreased expression of cyclophilin C and/or PN7718, then the disease or disorder may be treated or prevented by strengthening or stabilizing the interaction between cyclophilin C and PN7718 in a patient. Alternatively, if a disease or disorder is associated with mutant forms of cyclophilin C and/or PN7718 that lead to weakened or abolished protein—protein interaction therebetween, then the disease or disorder may be treated with a compound that initiates or stabilizes the interaction between the mutant forms of cyclophilin C and/or PN7718.

Typically, the screening methods comprise contacting the PN7718 protein with a PN7718-interacting protein in the presence of a test compound, and determining the interaction between the PN7718 protein and the PN7718-interacting protein. In a preferred embodiment, a two-hybrid system, e.g., a yeast two-hybrid as described in detail in Section 4 system is employed.

The yeast two-hybrid assays can be conducted in a similar manner as those described in Section 10.3.1 above. However, a positively selectable marker is preferably used. For example, PN7718 or a mutant form or a binding domain thereof, and cyclophilin C or a mutant form or a binding domain thereof are used as test proteins expressed in the form of fusion proteins as described above for purposes of a two-hybrid assay. The fusion proteins are expressed in a host cell and allowed to interact with each other in the presence of one or more test compounds.

A gene encoding a positively selectable marker such as the lacZ protein may be used as a reporter gene such that when a test compound enables or enhances the interaction between cyclophilin C, or a mutant form or a binding domain thereof, and PN7718 or a mutant form or a binding domain thereof, the expression of lacZ protein, i.e., beta-galatosidase is increased. As a result, the compound may be identified based on the appearance or increase of a blue color when the host cells are cultured in a medium containing X-gal.

Optionally, a control assay is performed in which the above screening assay is conducted in the absence of the test compound. The result is then compared with that obtained in the presence of the test compound.

10.4. Optimization of the Identified Compounds

Once test compounds capable of modulating the interaction between cyclophilin C and PN7718 or modulating cyclophilin C or PN7718 are selected, a data set including data defining the identity or characteristics of the test compounds can be generated. The data set may include information relating to the properties of a selected test compound, e.g., chemical structure, chirality, molecular weight, melting point, etc. Alternatively, the data set may simply include assigned identification numbers understood by the researchers conducting the screening assay and/or researchers receiving the data set as representing specific test compounds. The data or information can be cast in a transmittable form that can be communicated or transmitted to other researchers, particularly researchers in a different country. Such a transmittable form can vary and can be tangible or intangible. For example, the data set defining one or more selected test compounds can be embodied in texts, tables, diagrams, molecular structures, photographs, charts, images, or any other visual forms. The data or information can be recorded on a tangible media such as paper or embodied in computer-readable forms (e.g., electronic, electromagnetic, optical or other signals). The data in a computer-readable form can be stored in a computer usable storage medium (e.g., floppy disks, magnetic tapes, optical disks, and the like) or transmitted directly through a communication infrastructure. In particular, the data embodied in electronic signals can be transmitted in the form of email or posted on a website on the Internet or Intranet. In addition, the information or data on a selected test compound can also be recorded in an audible form and transmitted through any suitable media, e.g., analog or digital cable lines, fiber optic cables, etc., via telephone, facsimile, wireless mobile phone, Internet phone, and the like.

Thus, the information and data on a test compound selected in a screening assay described above or by virtual screening as discussed below can be produced anywhere in the world and transmitted to a different location. For example, when a screening assay is conducted offshore, the information and data on a selected test compound can be generated and cast in a transmittable form as described above. The data and information in a transmittable form thus can be imported into the U.S. or transmitted to any other countries, where the data and information may be used in further testing the selected test compound and/or in modifying and optimizing the selected test compound to develop lead compounds for testing in clinical trials.

Compounds can also be selected based on structural models of the target protein or protein complex and/or test compounds. In addition, once an effective compound is identified, structural analogs or mimetics thereof can be produced based on rational drug design with the aim of improving drug efficacy and stability, and reducing side effects. Methods known in the art for rational drug design can be used in the present invention. See, e.g., Hodgson et al., *Bio/Technology,* 9:19–21 (1991); U.S. Pat. Nos. 5,800,998 and 5,891,628, all of which are incorporated herein by reference. An example of rational drug design is the development of HIV protease inhibitors. See Erickson et al., *Science,* 249:527–533 (1990).

In this respect, structural information on the target protein or protein complex is obtained. Preferably, atomic coordinates can be obtained defining a three-dimensional structure of the target protein or protein complex. For example, when a protein complex is used as a target, each of the interacting members of a target protein complex can be expressed and purified. The purified interacting protein members are then allowed to interact with each other in vitro under appropriate conditions. Optionally, the interacting protein complex can be stabilized by crosslinking or other techniques. The interacting complex can be studied using various biophysics techniques including, e.g., X-ray crystallography, NMR, computer modeling, mass spectrometry, and the like. Likewise, atomic coordinates defining a three-dimensional structure can also be obtained from protein complexes formed by interacting proteins and a compound that initiates or stabilizes the interaction of the proteins. Methods for obtaining such atomic coordinates by X-ray crystallography, NMR, and the like are known in the art and the application thereof to the target protein or protein complex of the present invention should be apparent to skilled persons in the art of structural biology. See Smyth and Martin, *Mol. Pathol.,* 53:8–14 (2000); Oakley and Wilce, *Clin. Exp. Pharmacol. Physiol.,* 27(3):145–151 (2000); Ferentz and Wagner, *Q.*

*Rev. Biophys.*, 33:29–65 (2000); Hicks, *Curr. Med. Chem.*, 8(6):627–650 (2001); and Roberts, *Curr. Opin. Biotechnol.*, 10:42–47 (1999).

In addition, understanding of the interaction between the proteins of interest in the presence or absence of a modulator compound can also be derived from mutagenic analyses using yeast two-hybrid systems or other methods for detecting protein—protein interactions. In this respect, various mutations can be introduced into the interacting proteins and the effect of the mutations on protein—protein interactions can be examined by a suitable method such as the yeast two-hybrid system.

Various mutations including amino acid substitutions, deletions and insertions can be introduced into a protein sequence using conventional recombinant DNA technologies. Generally, it is particularly desirable to decipher the protein binding sites. Thus, it is important that the mutations introduced only affect protein—protein interactions and cause minimal structural disturbances. Mutations are preferably designed based on knowledge of the three-dimensional structure of the interacting proteins. Preferably, mutations are introduced to alter charged amino acids or hydrophobic amino acids exposed on the surface of the proteins, since ionic interactions and hydrophobic interactions are often involved in protein—protein interactions. Alternatively, the "alanine scanning mutagenesis" technique is used. See Wells, et al., *Methods Enzymol.*, 202:301–306 (1991); Bass et al., *Proc. Natl. Acad. Sci. USA*, 88:4498–4502 (1991); Bennet et al., *J. Biol. Chem.*, 266: 5191–5201 (1991); Diamond et al., *J. Virol.*, 68:863–876 (1994). Using this technique, charged or hydrophobic amino acid residues of the interacting proteins are replaced by alanine, and the effect on the interaction between the proteins is analyzed using e.g., the yeast two-hybrid system. For example, the entire protein sequence can be scanned in a window of five amino acids. When two or more charged or hydrophobic amino acids appear in a window, the charged or hydrophobic amino acids are changed to alanine using standard recombinant DNA techniques. The thus-mutated proteins are used as "test proteins" in the above-described two-hybrid assay to examine the effect of the mutations on protein—protein interaction. Preferably, the mutagenesis analysis is conducted both in the presence and in the absence of an identified modulator compound. In this manner, the domains or residues of the proteins important to protein—protein interaction and/or the interaction between the modulator compound and the proteins can be identified.

Based on the information obtained, structural relationships between the interacting proteins, as well as between the identified compound and the interacting proteins are elucidated. The moieties and the three-dimensional structure of the identified compound, i.e., lead compound, critical to its modulating effect on the interaction of the proteins of interest are revealed. Using this information and various techniques known in the art of molecular modeling (i.e., simulated annealing), medicinal chemists can then design analog compounds that might be more effective modulators of the protein—protein interactions of the present invention. For example, the analog compounds might show more specific or tighter binding to their targets, and thereby might exhibit fewer side effects, or might have more desirable pharmacological characteristics (e.g., greater solubility).

In addition, an identified peptide compound capable of modulating particular protein—protein interactions can also be analyzed by the alanine scanning technique and/or the two-hybrid assay to determine the domains or residues of the peptide important to its modulating effect on particular protein—protein interactions. The peptide compound can be used as a lead molecule for rational design of small organic molecules or peptide mimetics. See Huber et al., *Curr. Med. Chem.*, 1:13–34 (1994).

The domains, residues or moieties critical to the modulating effect of the identified compound constitute the active region of the compound known as its "pharmacophore." Once the pharmacophore has been elucidated, a structural model can be established by a modeling process that may incorporate data from NMR analysis, X-ray diffraction data, alanine scanning, spectroscopic techniques and the like. Various techniques including computational analysis, similarity mapping and the like can all be used in this modeling process. See e.g., Perry et al., in *OSAR: Quantitative Structure-Activity Relationships in Drug Design*, pp. 189–193, Alan R. Liss, Inc., 1989; Rotivinen et al., *Acta Pharmaceutical Fennica*, 97:159–166 (1988); Lewis et al., *Proc. R. Soc. Lond.*, 236:125–140 (1989); McKinaly et al., *Annu. Rev. Pharmacol. Toxiciol.*, 29:111–122 (1989). Commercial molecular modeling systems available from Polygen Corporation, Waltham, Mass., include the CHARMm program, which performs the energy minimization and molecular dynamics functions, and QUANTA program, which performs the construction, graphic modeling and analysis of molecular structure. Such programs allow interactive construction, visualization and modification of molecules. Other computer modeling programs are also available from BioDesign, Inc. (Pasadena, Calif.), Hypercube, Inc. (Cambridge, Ontario), and Allelix, Inc. (Mississauga, Ontario, Canada).

A template can be formed based on the established model. Various compounds can then be designed by linking various chemical groups or moieties to the template. Various moieties of the template can also be replaced. In addition, in the case of a peptide lead compound, the peptide or mimetics thereof can be cyclized, e.g., by linking the N-terminus and C-terminus together, to increase its stability. These rationally designed compounds are further tested. In this manner, pharmacologically acceptable and stable compounds with improved efficacy and reduced side effects can be developed.

The compounds identified in accordance with the present invention can be incorporated into a pharmaceutical formulation suitable for administration to an individual.

In addition, the structural models or atomic coordinates defining a three-dimensional structure of the target protein or protein complex can also be used in virtual screen to select compounds capable of modulating the target protein or protein complex. Various methods of computer-based virtual screen using atomic coordinates are generally known in the art. For example, U.S. Pat. No. 5,798,247 (which is incorporated herein by reference) discloses a method of identifying a compound (specifically, an interleukin converting enzyme inhibitor) by determining binding interactions between an organic compound and binding sites of a binding cavity within the target protein. The binding sites are defined by atomic coordinates.

The compounds designed or selected based on rational drug design or virtual screen can be tested for their ability to modulate (interfere with or strengthen) the interaction between the interacting partners within the protein complexes of the present invention. In addition, the compounds can also be further tested for their ability to modulate (inhibit or enhance) cellular functions such as intracellular calcium signaling, beta-amyloid formation, T-cell receptor and IgE receptor signaling pathways, and protein folding and degradation in cells as well as their effectiveness in treating diseases such as autoimmune diseases, neurological diseases and cardiovascular disorders.

11. Modulating PN7718 and PN7718-Containing Protein Complexes

As described above, the interactions between cyclophilin C and PN7718 suggest that cyclophilin C, PN7718, interacting proteins thereof, and the protein complexes formed by such proteins may be involved in common biological processes and disease pathways. Thus, the modulation (i.e., activation or inhibition of the levels or activities) of PN7718, cyclophilin C, interacting proteins thereof, or the protein complexes formed by the proteins may lead to the modulation of the biological processes and treatment of the diseases.

As used herein, modulating a protein or a protein complex means causing any forms of alteration of the properties, activities or levels of the protein or protein complex, including but not limited to e.g., enhancing or reducing their biological functional activities, increasing or decreasing their stability, altering their affinity or specificity to certain molecules, etc.

For example, cyclophilin C, PN7718, interacting proteins thereof, and the protein complexes of the present invention may be involved in intracellular calcium signaling, beta-amyloid formation, T-cell receptor and IgE receptor signaling pathways, and protein folding and degradation. The modulation of intracellular calcium signaling, beta-amyloid formation, T-cell receptor and IgE receptor signaling pathways, and protein folding and degradation may lead to the treatment of diseases and disorders associated with intracellular calcium signaling, beta-amyloid formation, T-cell receptor and IgE receptor signaling pathways, and protein folding and degradation. In addition, the diagnostic methods described in Section 9 can be used in associating aberrations in the proteins or protein complexes of the present invention with a physiological disorder or disease or predisposition to a physiological disorder or disease. The diagnostic methods described in Section 9 may also be used in diagnosing the diseases and disorders. Once a patient is diagnosed, it is possible to ameliorate the disease or reduce the disease symptoms by modulating, in the patient, the functions or activities of the PN7718-containing protein complexes or the functions or activities of a protein member of the protein complexes (e.g., cyclophilin C, PN7718).

Accordingly, the present invention provides methods for modulating PN7718, PN7718-interacting proteins, and PN7718-containing protein complexes. The methods may include modulating (i.e., increasing or decreasing) the level of PN7718, PN7718-interacting proteins, or PN7718-containing protein complexes in cells, and/or modulating the activities of PN7718, PN7718-interacting proteins, or PN7718-containing protein complexes in cells. In addition, the present invention also provides methods for modulating intracellular calcium signaling, beta-amyloid formation, T-cell receptor and IgE receptor signaling pathways, and protein folding and degradation, which comprise modulating the levels or activities of PN7718, PN7718-interacting proteins, or PN7718-containing protein complexes in cells.

The modulating methods of the present invention may be applied in vitro to cells or tissue. Alternatively, the methods of modulating PN7718, PN7718-interacting proteins, or PN7718-containing protein complexes and the methods for modulating intracellular calcium signaling, beta-amyloid formation, T-cell receptor and IgE receptor signaling pathways, and protein folding and degradation may also be applicable in an in vivo approach to cells or tissues in patients. Additionally, the in vivo application of the methods of the present invention may be useful in the treatment of various diseases and disorders.

11.1. Applicable Diseases

The methods for modulating the PN7718-containing complexes or the interacting protein members thereof may be used in treating and preventing immunological disorders such as autoimmune diseases including, but not limited to, rheumatoid arthritis, systemic lupus erythematosus (SLE), Sjogren's syndrome, Canale-Smith syndrome, psoriasis, scleroderma, dermatomyositis, polymyositis, Behcet's syndrome, skin-related autoimmue diseases such as bullus pemphigoid, IgA dermatosis, pemphigus vulgaris, pemphigus foliaceus, dermatitis herpetiformis, contact dermatitis, autoimmune allopecia, erythema nodosa, and epidermolysis bullous aquisita, drug-induced hemotologic autoimmune disorders, autoimmue thrombocytopenic purpura, autoimmune neutropenia, systemic sclerosis, multiple sclerosis, imflammatory demyelinating, diabetes mellitus, autoimmune polyglandular syndromes, vasculitides, Wegener's granulomatosis, Hashimoto's disease, multinodular goitre, Grave's disease, autoimmune encephalomyelitis (EAE), demyelinating diseases, etc.

The methods of the present invention can also be useful in treating or preventing neurodegenerative disorders including, but not limited to, dementia (including Alzheimer's disease, mild cognitive impairment etc.), frontotemporal dementia, Parkinson's disease, Huntington's disease, brain trauma, infarction, hemorrhage, amytrophic lateral sclerosis/Lou Gehrig's disease (ALS), inherited ataxias such as olivopontocerebellar atrophy (spinocerebellar ataxia type 1), and Machado-Joseph disease (spinocerebellar ataxia type 3).

Additionally, the methods for modulating the PN7718-containing complexes or the interacting protein members thereof may also be effective in treating or preventing neurological and behavioral disorders associated with abnormal neurotransmission, abnormal neuronal growth and development, and other related neuronal dysfunctions. In a specific embodiment, a method for treating or preventing schizophrenia is provided which includes modulating the PN7718-containing complexes or the interacting protein members thereof. Other various diseases involving abnormal neuronal growth or injuries may also be treated. Examples of such disorders include various disorders caused by supratentorial mass lesions, subtentorial mass or destructive lesions, or metabolic brain diseases, lesions of the peripheral common motor, sensory and autonomic pathways. The method for modulating the PN7718-containing complexes or the interacting protein members thereof may also be used in treating diseases and disorders such as delirium, dementia, Korsakoff' syndrome, manic-depressive psychosis, anxiety, depression, and hysteria.

Further, the modulation methods of the present invention may be useful in the treatment and prevention of cardiovascular disorders such as congestive heart failure; ischemic heart diseases (e.g., angina pectoris, myocardial infarction, chronic ischemic heart disease); hypertensive heart disease; valvular heart diseases (e.g., degerative calcific aortic valve stenosis, myxomatous degeneration of the mitral valve, rheumatic heart disease, and endocarditis); myocardial diseases including cardiomyopathy and myocarditis; pericarditis; sinus node disfunction, and arrhthmia.

11.2. Methods of Inhibition

In one embodiment, the modulating methods of the present invention are employed to inhibit PN7718, PN7718-interacting proteins, or PN7718-containing protein complexes in cells in vitro, or in vivo in a patient. For this purpose, the cellular or tissue levels of PN7718, PN7718-interacting proteins, or PN7718-containing protein complexes can be reduced by various techniques known in the art. For example, the relevant gene expression in cells may be inhibited by, e.g., antisense therapy, ribozyme therapy or gene therapy. Alternatively, compounds may be administered to inhibit the activities of PN7718, PN7718-interacting proteins, or PN7718-containing protein complexes. For example, antibodies or small organic compounds specific to PN7718, PN7718-interacting proteins, or PN7718-containing protein complexes may be used. The inhibition methods of this invention are particularly useful in cases where the activities of PN7718, PN7718-interacting proteins or PN7718-containing protein complexes contribute to a particular disease or disorder.

11.2.1. Administration of Antibodies

Antibodies immunoreactive with PN7718, PN7718-interacting proteins or PN7718-containing protein complexes may be administered to cells in vitro or in vivo. Suitable antibodies may be monoclonal or polyclonal that fall within any antibody classes, e.g., IgG, IgM, IgA, etc. The suitable antibodies may also take a form of various antibody fragments including, but not limited to, Fab and F(ab')$_2$, single-chain fragments (scFv), and the like. In one embodiment, an antibody selectively immunoreactive with the protein complex formed from PN7718 and cyclophilin C in accordance with the present invention is administered to cells in vitro or in vivo. In another embodiment, an antibody specific to PN7718 is administered. In yet another embodiment, both types of antibodies are administered.

Methods for making the antibodies of the present invention should be apparent to a person of skill in the art, especially in view of the discussions in Section 7 above. The antibodies can be administered in any suitable form via any suitable route as described in Section 13 below. Preferably, the antibodies are administered in a pharmaceutical composition together with a pharmaceutically acceptable carrier.

Alternatively, the antibodies may be delivered by a gene-therapy approach. That is, nucleic acids encoding the antibodies, particularly single-chain fragments (scFv), may be introduced into cells such that desirable antibodies may be produced recombinantly in the cells in vitro or in vivo from the nucleic acids. For this purpose, the nucleic acids with appropriate transcriptional and translation regulatory sequences can be directly administered into cells. Alternatively, the nucleic acids can be incorporated into a suitable vector as described in Sections 4 and 11.3.2 and delivered into cells along with the vector. The expression vector containing the nucleic acids can be administered directly to cells by any known molecular biology techniques. For in vivo deliveries, the expression vector can first be introduced into cells, preferably cells derived from a patient to be treated, and subsequently delivered into the patient by cell transplantation. See Section 11.3.2 below.

11.2.2. Antisense Therapy

In another embodiment, antisense compounds are employed in the modulating methods of the present invention to reduce the level of PN7718, PN7718-interacting proteins or PN7718-containing protein complexes. For purposes of reducing the PN7718 level, antisense compounds specific to nucleic acids encoding PN7718 may be administered to cells in vitro, or in vivo in a patient to be therapeutically or prophylactically treated. To reduce the level of a PN7718-containing protein complex, antisense compounds specific to nucleic acids encoding one or more interacting protein members of the protein complex may be used. In a specific embodiment, an antisense compound specific to PN7718 nucleic acids and an antisense compound specific to cyclophilin C nucleic acids are employed. As is known in the art, antisense drugs generally act by hybridizing to a particular target nucleic acid thus blocking gene expression. Thus, the antisense compounds should specifically inhibit the expression of the protein or protein complex whose level is to be inhibited. Methods for designing antisense compounds and using such compounds in treating diseases are well known and well developed in the art. For example, the antisense drug Vitravene® (fomivirsen), a 21-base long oligonucleotide, has been successfully developed and marketed by Isis Pharmaceuticals, Inc. for treating cytomegalovirus (CMV)-induced retinitis.

Any methods for designing and making antisense compounds may be used for the purpose of the present invention. See generally, Sanghvi et al., eds., *Antisense Research and Applications*, CRC Press, Boca Raton, 1993. Typically, antisense compounds are oligonucleotides designed based on the nucleotide sequence of the mRNA or gene of one or more of the interacting protein members of a particular protein complex of the present invention. In particular, antisense compounds can be designed to specifically hybridize to a particular region of the gene sequence or mRNA of one or more of the interacting protein members to modulate (increase or decrease) replication, transcription, or translation. As used herein, the term "specifically hybridize" or paraphrases thereof means a sufficient degree of complementarity or pairing between an antisense oligo and a target DNA or mRNA such that stable and specific binding occurs therebetween. In particular, 100% complementary or pairing is not required. Specific hybridization takes place when sufficient hybridization occurs between the antisense compound and its intended target nucleic acids in the substantial absence of non-specific binding of the antisense compound to non-target sequences under predetermined conditions, e.g., for purposes of in vivo treatment, preferably under physiological conditions. Preferably, specific hybridization results in the interference with normal expression of the target DNA or mRNA.

For example, an antisense oligo can be designed to specifically hybridize to the replication or transcription regulatory regions of a target gene, or the translation regulatory regions such as translation initiation region and exon/intron junctions, or the coding regions of a target mRNA.

As is generally known in the art, commonly used oligonucleotides are oligomers or polymers of ribonucleic acid or deoxyribonucleic acid having a combination of naturally-occurring nucleoside bases, sugars and covalent linkages between nucleoside bases and sugars including a phosphate group. However, it is noted that the term "oligonucleotides" also encompasses various non-naturally occurring mimetics and derivatives, i.e., modified forms, of naturally-occurring oligonucleotides as described below. Typically an antisense compound of the present invention is an oligonucleotide having from about 6 to about 200, preferably from about 8 to about 30 nucleoside bases.

The antisense compounds preferably contain modified backbones or non-natural internucleoside linkages, including but not limited to, modified phosphorous-containing backbones and non-phosphorous backbones such as morpholino backbones; siloxane, sulfide, sulfoxide, sulfone, sulfonate, sulfonamide, and sulfamate backbones; formacetyl and thioformacetyl backbones; alkene-containing backbones; methyleneimino and methylenehydrazino backbones; amide backbones, and the like.

Examples of modified phosphorous-containing backbones include, but are not limited to phosphorothioates, phosphorodithioates, chiral phosphorothioates, phosphotriesters, aminoalkylphosphotriesters, alkyl phosphonates, thionoalkylphosphonates, phosphinates, phosphoramidates, thionophosphoramidates, thionoalkylphosphotriesters, and boranophosphates and various salt forms thereof. See e.g., U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Examples of the non-phosphorous containing backbones described above are disclosed in, e.g., U.S. Pat. Nos. 5,034,506; 5,185,444; 5,214,134; 5,216,141; 5,235,033; 5,264,562; 5,264,564; 5,405,938; 5,434,257; 5,470,967; 5,489,677; 5,541,307; 5,561,225; 5,596,086; 5,610,289; 5,602,240; 5,608,046; 5,610,289; 5,618,704; 5,623,070; 5,663,312; 5,677,437; and 5,677,439, each of which is herein incorporated by reference.

Another useful modified oligonucleotide is peptide nucleic acid (PNA), in which the sugar-backbone of an oligonucleotide is replaced with an amide containing backbone, e.g., an aminoethylglycine backbone. See U.S. Pat. Nos. 5,539,082 and 5,714,331; and Nielsen et al., *Science*, 254, 1497–1500 (1991), all of which are incorporated herein by reference. PNA antisense compounds are resistant to RNase H digestion and thus exhibit longer half-life. In addition, various modifications may be made in PNA backbones to impart desirable drug profiles such as better stability, increased drug uptake, higher affinity to target nucleic acid, etc.

Alternatively, the antisense compounds are oligonucleotides containing modified nucleosides, i.e., modified purine or pyrimidine bases, e.g., 5-substituted pyrimidines, 6-azapyrimidines, and N-2, N-6 and O-substituted purines, and the like. See e.g., U.S. Pat. Nos. 3,687,808; 4,845,205; 5,130,302; 5,175,273; 5,367,066; 5,432,272; 5,459,255; 5,484,908; 5,502,177; 5,525,711; 5,587,469; 5,594,121; 5,596,091; 5,681,941; and 5,750,692, each of which is incorporated herein by reference in its entirety.

In addition, oligonucleotides with substituted or modified sugar moieties may also be used. For example, an antisense compound may have one or more 2'-O-methoxyethyl sugar moieties. See e.g., U.S. Pat. Nos. 4,981,957; 5,118,800; 5,319,080; 5,393,878; 5,446,137; 5,466,786; 5,514,785; 5,567,811; 5,576,427; 5,591,722; 5,610,300; 5,627,0531 5,639,873; 5,646,265; 5,658,873; 5,670,633; and 5,700,920, each of which is herein incorporated by reference.

Other types of oligonucleotide modifications are also useful including linking an oligonucleotide to a lipid, phospholipid or cholesterol moiety, cholic acid, thioether, aliphatic chain, polyamine, polyethylene glycol (PEG), or a protein or peptide. The modified oligonucleotides may exhibit increased uptake into cells, improved stability, i.e., resistance to nuclease digestion and other biodegradations. See e.g., U.S. Pat. No. 4,522,811; Burnham, *Am. J. Hosp. Pharm.*, 15:210–218 (1994).

Antisense compounds can be synthesized using any suitable methods known in the art. In fact, antisense compounds may be custom made by commercial suppliers. Alternatively, antisense compounds may be prepared using DNA synthesizers commercially available from various vendors, e.g., Applied Biosystems Group of Norwalk, Conn.

The antisense compounds can be formulated into a pharmaceutical composition with suitable carriers and administered into a patient using any suitable route of administration. Alternatively, the antisense compounds may also be used in a "gene-therapy" approach. That is, the oligonucleotide is subcloned into a suitable vector and transformed into human cells. The antisense oligonucleotide is then produced in vivo through transcription. Methods for gene therapy are disclosed in Section 11.3.2 below.

11.2.3. Ribozyme Therapy

In another embodiment, an enzymatic RNA or ribozyme is used in the modulating methods of the present invention to reduce the level of PN7718, PN7718-interacting proteins or PN7718-containing protein complexes. Ribozymes are RNA molecules, which have an enzymatic activity and are capable of repeatedly cleaving other separate RNA molecules in a nucleotide base sequence specific manner. See Kim et al., *Proc. Natl. Acad. of Sci. USA*, 84:8788 (1987); Haseloff and Gerlach, *Nature*, 334:585 (1988); and Jefferies et al., *Nucleic Acid Res.*, 17:1371 (1989). A ribozyme typically has two portions: a catalytic portion and a binding sequence that guides the binding of ribozymes to a target RNA through complementary base-pairing. Once the ribozyme is bound to a target RNA, it enzymatically cleaves the target RNA, typically destroying its ability to direct translation of an encoded protein. After a ribozyme has cleaved its RNA target, it may be released from that target RNA and thereafter can bind and cleave another target. That is, a single ribozyme molecule can repeatedly bind and cleave new targets. Therefore, one advantage of ribozyme treatment is that a lower amount of exogenous RNA is required as compared to conventional antisense therapies. In addition, ribozymes exhibit lower affinity for mRNA targets than do DNA-based antisense oligos, and therefore are less prone to bind to inappropriate targets.

To reduce the PN7718 level, ribozymes specific to nucleic acids encoding PN7718 may be administered to cells in vitro, or administered in vivo to a patient to be therapeutically or prophylactically treated. For purposes of inhibiting a PN7718-containing protein complex, ribozyme compounds specific to nucleic acids encoding one or more interacting protein members of the protein complex may be used. In a specific embodiment, a ribozyme compound specific to PN7718 nucleic acids and a ribozyme compound specific to cyclophilin C nucleic acids are employed.

In accordance with the present invention, a ribozyme may target any portions of the target mRNA. Methods for selecting a ribozyme target sequence and designing and making ribozymes are generally known in the art. See e.g., U.S. Pat. Nos. 4,987,071; 5,496,698; 5,525,468; 5,631,359; 5,646,020; 5,672,511; and 6,140,491, each of which is incorporated herein by reference in its entirety. For example, suitable ribozymes may be designed in various configurations such as hammerhead motifs, hairpin motifs, hepatitis delta virus motifs, group I intron motifs, or RNase P RNA motifs. See e.g., U.S. Pat. Nos. 4,987,071; 5,496,698; 5,525,468;

5,631,359; 5,646,020; 5,672,511; and 6,140,491; Rossi et al., *AIDS Res. Human Retroviruses* 8:183 (1992); Hampel and Tritz, *Biochemistry* 28:4929 (1989); Hampel et al., *Nucleic Acids Res.*, 18:299 (1990); Perrotta and Been, *Biochemistry* 31:16 (1992); and Guerrier-Takada et al., *Cell*, 35:849 (1983).

Ribozymes can be synthesized by the same methods used for normal RNA synthesis. For example, such methods are disclosed in Usman et al., *J. Am. Chem. Soc.*, 109:7845–7854 (1987) and Scaringe et al., *Nucleic Acids Res.*, 18:5433–5441 (1990). Modified ribozymes may be synthesized by the methods disclosed in, e.g., U.S. Pat. No. 5,652,094; International Publication Nos. WO 91/03162; WO 92/07065 and WO 93/15187; European Patent Application No. 92110298.4; Perrault et al., *Nature*, 344:565 (1990); Pieken et al., *Science*, 253:314 (1991); and Usman and Cedergren, *Trends in Biochem. Sci.*, 17:334 (1992).

Ribozymes of the present invention may be administered to cells by any known methods, e.g., disclosed in International Publication No. WO 94/02595. For example, they can be administered directly to a patient through any suitable route, e.g., intravenous injection. Alternatively, they may be delivered in encapsulation in liposomes, by iontophoresis, or by incorporation into other vehicles such as hydrogels, cyclodextrins, biodegradable nanocapsules, and bioadhesive microspheres. In addition, they may also be delivered by a gene therapy approach, using a DNA vector from which the ribozyme RNA can be transcribed directly. Gene therapy methods are disclosed in detail below in Section 11.3.2.

11.2.4. Other Methods

The level and activity of PN7718 and/or a particular PN7718-containing protein complex of the present invention may also be inhibited by various other methods. In one embodiment, the modulating methods include contacting PN7718 or a PN7718-containing protein complex with a compound capable of inhibiting the activities of PN7718 or the protein complex.

For example, compounds identified in accordance with the methods described in Section 10 that are capable of interfering with or disrupting protein—protein interactions between the interacting protein members of a protein complex may be administered to cells in vitro, or administered in vivo to a patient to be therapeutically or prophylactically treated. Compounds identified in the assays described in Section 10 that bind to a PN7718-containing protein complex or the interacting members thereof may also be used in the methods for inhibiting PN7718 or a PN7718-containing protein complex of the present invention. In a specific embodiment, a modulator of PN7718 is used to inhibit the activities of PN7718.

In addition, useful agents also include incomplete proteins, i.e., fragments of the interacting protein members that are capable of binding to their respective binding partners in a protein complex but are defective with respect to their cellular functions. For example, binding domains of the interacting member proteins of a protein complex may be used as competitive inhibitors of the activities of the protein complex. As will be apparent to skilled artisans, derivatives or homologues of the binding domains may also be used. Binding domains can be easily identified using molecular biology techniques, e.g., mutagenesis in combination with yeast two-hybrid assays. Preferably, the protein fragment used is a fragment of an interacting protein member having a length of less than 90%, 80%, more preferably less than 75%, 65%, 50%, or less than 40% of the full length of the protein member. In one embodiment, a PN7718 protein fragment is administered. In a specific embodiment, one or more of the binding domains of PN7718 protein in Table 1 are administered to cells in vitro or administered to a patient in need of such treatment. For example, suitable protein fragments can include a polypeptide having a contiguous span of at least 4, 5, 6, 7, 8, 9, 10, 11, 12, 13, 14, 15, 18, 20, 25, 30, 40, 50, 60, 70, 80, 90, 100, 125 or 150 amino acids, preferably from 4 to 30, 40 or 50 amino acids or more of the sequence of SEQ ID NO:2 and is capable of interacting with cyclophilin C. Also, suitable protein fragments can also include a peptide capable of binding cyclophilin C and having an amino acid sequence of from 4 to 30 amino acids that is at least 75%, 80%, 82%, 85%, 87%, 90%, 95% or more identical to a contiguous span of amino acids of SEQ ID NO:2 of the same length. Alternatively, a polypeptide capable of interacting with PN7718 and having a contiguous span of at least 4, 5, 6, 7, 8, 9, 10, 11, 12, 13, 14, 15, 18, 20, 25, 30, 40, 50, 60, 70, 80, 90, 100, 125 or 150 amino acids, preferably from 4 to 30, 40 or 50 or more amino acids of the amino acid sequence of cyclophilin C may be administered. Also, other examples of suitable compounds include a peptide capable of binding PN7718 and having an amino acid sequence of from 4 to 30, 40, 50 or more amino acids that is at least 75%, 80%, 82%, 85%, 87%, 90%, 95% or more identical to a contiguous span of amino acids of cyclophilin C amino acid sequence of the same length. In addition, the administered compounds can also be an antibody or antibody fragment, preferably single-chain antibody immunoreactive with cyclophilin C or PN7718 or protein complexes of the present invention.

The protein fragments suitable as competitive inhibitors can be delivered into cells by direct cell internalization, receptor mediated endocytosis, or via a "transporter." It is noted that when the target proteins or protein complexes to be modulated reside inside cells, the compound administered to cells in vitro or in vivo in the method of the present invention preferably is delivered into the cells in order to achieve optimal results. Thus, preferably, the compound to be delivered is associated with a transporter capable of increasing the uptake of the compound by cells having the target protein or protein complex. As used herein, the term "associated with" means a compound to be delivered is physically associated with a transporter. The compound and the transporter can be covalently linked together, or associated with each other as a result of physical affinities such as forces caused by electrical charge differences, hydrophobicity, hydrogen bonds, van der Waals force, ionic force, or a combination thereof. For example, the compound can be encapsulated within a transporter such as a cationic liposome.

As used herein, the term "transporter" refers to an entity (e.g., a compound or a composition or a physical structure formed from multiple copies of a compound or multiple different compounds) that is capable of facilitating the uptake of a compound of the present invention by a mammalian cell, particularly a human cell. Typically, the cell uptake of a compound of the present invention in the presence of a "transporter" is at least 50% higher than the cell uptake of the compound in the absence of the "transporter." Preferably, the cell uptake of a compound of the present invention in the presence of a "transporter" is at least 75% higher, preferably at least 100% or 200% higher, and more preferably at least 300%, 400% or 500% higher than the cell uptake of the compound in the absence of the "transporter." Methods of assaying cell uptake of a compound should be apparent to skilled artisans. For example, the compound to be delivered can be labeled with a radioactive isotope or another detectable marker (e.g., a fluorescence marker), and added to cultured cells in the presence or absence of a transporter, and incubated for a time period sufficient to allow maximal uptake. Cells can then be separated from the culture medium and the detectable signal (e.g., radioactivity) caused by the compound inside the cells can be measured. The result obtained in the presence of a transporter can be compared to that obtained in the absence of a transporter.

Many molecules and structures known in the art can be used as "transporter." In one embodiment, a penetratin is used as a transporter. For example, the homeodomain of Antennapedia, a *Drosophila* transcription factor, can be used as a transporter to deliver a compound of the present invention. Indeed, any suitable member of the penetratin class of peptides can be used to carry a compound of the present invention into cells. Penetratins are disclosed in, e.g., Derossi et al., *Trends Cell Biol.*, 8:84–87 (1998), which is incorporated herein by reference. Penetratins transport molecules attached thereto across cytoplasm membranes or nucleus membranes efficiently in a receptor-independent, energy-independent, and cell type-independent manner. Methods for using a penetratin as a carrier to deliver oligonucleotides and polypeptides are also disclosed in U.S. Pat. No. 6,080,724; Pooga et al., *Nat. Biotech.*, 16:857 (1998); and Schutze et al., *J. Immunol.*, 157:650 (1996), all of which are incorporated herein by reference. U.S. Pat. No. 6,080,724 defines the minimal requirements for a penetratin peptide as a peptide of 16 amino acids with 6 to 10 of which being hydrophobic. The amino acid at position 6 counting from either the N- or C-terminal is tryptophan, while the amino acids at positions 3 and 5 counting from either the N- or C-terminal are not both valine. Preferably, the helix 3 of the homeodomain of *Drosophila* Antennapedia is used as a transporter. More preferably, a peptide having a sequence of the amino acids 43–58 of the homeodomain Antp is employed as a transporter. In addition, other naturally occurring homologs of the helix 3 of the homeodomain of *Drosophila* Antennapedia can also be used. For example, homeodomains of Fushi-tarazu and Engrailed have been shown to be capable of transporting peptides into cells. See Han et al., *Mol. Cells*, 10:728–32 (2000). As used herein, the term "penetratin" also encompasses peptoid analogs of the penetratin peptides. Typically, the penetratin peptides and peptoid analogs thereof are covalently linked to a compound to be delivered into cells thus increasing the cellular uptake of the compound.

In another embodiment, the HIV-1 tat protein or a derivative thereof is used as a "transporter" covalently linked to a compound according to the present invention. The use of HIV-1 tat protein and derivatives thereof to deliver macromolecules into cells has been known in the art. See Green and Loewenstein, *Cell*, 55:1179 (1988); Frankel and Pabo, *Cell*, 55:1189 (1988); Vives et al., *J. Biol. Chem.*, 272: 16010–16017 (1997); Schwarze et al., *Science*, 285:1569–1572 (1999). It is known that the sequence responsible for cellular uptake consists of the highly basic region, amino acid residues 49–57. See e.g., Vives et al., *J. Biol. Chem.*, 272:16010–16017 (1997); Wender et al., *Proc. Nat'l. Acad. Sci. USA*, 97:13003–13008 (2000). The basic domain is believed to target the lipid bilayer component of cell membranes. It causes a covalently linked protein or nucleic acid to cross cell membrane rapidly in a cell type-independent manner. Proteins ranging in size from 15 to 120 kD have been delivered with this technology into a variety of cell types both in vitro and in vivo. See Schwarze et al., *Science*, 285:1569–1572 (1999). Any HIV tat-derived peptides or peptoid analogs thereof capable of transporting macromolecules such as peptides can be used for purposes of the present invention. For example, any native tat peptides having the highly basic region, amino acid residues 49–57 can be used as a transporter by covalently linking it to the compound to be delivered. In addition, various analogs of the tat peptide of amino acid residues 49–57 can also be useful transporters for purposes of this invention. Examples of various such analogs are disclosed in Wender et al., *Proc. Nat'l Acad. Sci. USA*, 97:13003–13008 (2000) (which is incorporated herein by reference) including, e.g., d-Tat$_{49-57}$, retro-inverso isomers of l- or d-Tat$_{49-57}$ (i.e., l-Tat$_{57-49}$ and d-Tat$_{57-49}$), L-arginine oligomers, D-arginine oligomers, L-lysine oligomers, D-lysine oligomers, L-histine oligomers, D-histine oligomers, L-ornithine oligomers, D-ornithine oligomers, and various homologues, derivatives (e.g., modified forms with conjugates linked to the small peptides) and peptoid analogs thereof. Preferably, arginine oligomers are preferred to the other oligomers, since arginine oligomers are much more efficient in promoting cellular uptake. As used herein, the term "oligomer" means a molecule that includes a covalently linked chain of amino acid residues of the same amino acids having a large enough number of such amino acid residues to confer transporter activities on the molecule. Typically, an oligomer contains at least 6, preferably at least 7, 8, or at least 9 such amino acid residues. In one embodiment, the transporter is a peptide that includes at least six contiguous amino acid residues that are a combination of two or more of L-arginine, D-arginine, L-lysine, D-lysine, L-histidine, D-histine, L-ornithine, and D-ornithine.

Other useful transporters known in the art include, but are not limited to, short peptide sequences derived from fibroblast growth factor (See Lin et al., *J. Biol. Chem.*, 270: 14255–14258 (1998)), Galparan (See Pooga et al., *FASEB J.* 12:67–77 (1998)), and HSV-1 structural protein VP22 (See Elliott and O'Hare, *Cell*, 88:223–233 (1997)).

As the above-described various transporters are generally peptides, fusion proteins can be conveniently made by recombinant expression to contain a transporter peptide covalently linked by a peptide bond to a competitive protein fragment. Alternatively, conventional methods can be used to chemically synthesize a transporter peptide or a peptide of the present invention or both.

The hybrid peptide can be administered to cells in vitro or to a patient in a suitable pharmaceutical composition as provided in Section 13.

In addition to peptide-based transporters, various other types of transporters can also be used, including but not limited to cationic liposomes (see Rui et al., *J. Am. Chem. Soc.*, 120:11213–11218 (1998)), dendrimers (Kono et al., *Bioconjugate Chem.*, 10:1115–1121 (1999)), siderophores (Ghosh et al., *Chem. Biol.*, 3:1011–1019 (1996)), etc. In a specific embodiment, the compound according to the present invention is encapsulated into liposomes for delivery into cells.

Additionally, when a compound according to the present invention is a peptide, it can be administered to cells by a gene therapy method. That is, a nucleic acid encoding the peptide can be administered to in vitro cells or to cells in vivo in a human or animal body. Any suitable gene therapy methods may be used for purposes of the present invention. Various gene therapy methods are well known in the art and are described in Section 11.3.2. below. Successes in gene therapy have been reported recently. See e.g., Kay et al., *Nature Genet.*, 24:257–261 (2000); Cavazzana-Calvo et al.,

*Science,* 288:669 (2000); and Blaese et al., *Science,* 270: 475 (1995); Kantoff, et al., *J. Exp. Med.,* 166:219 (1987).

In yet another embodiment, the gene therapy methods discussed in Section 11.3.2. below are used to "knock out" the gene encoding PN7718, or to reduce the PN7718 gene expression level, or to introduce mutations in the PN7718 gene that causes reduction of activities in the encoded PN7718 protein. For example, the gene may be replaced with a different gene sequence or a non-functional sequence or simply deleted by homologous recombination. In another gene therapy embodiment, the method disclosed in U.S. Pat. No. 5,641,670, which is incorporated herein by reference, may be used to reduce the expression of PN7718. Essentially, an exogenous DNA having at least a regulatory sequence, an exon and a splice donor site can be introduced into an endogenous gene encoding PN7718 by homologous recombination such that the regulatory sequence, the exon and the splice donor site present in the DNA construct become operatively linked to the endogenous gene. As a result, the expression of the endogenous gene is controlled by the newly introduced exogenous regulatory sequence. Therefore, when the exogenous regulatory sequence is a strong gene expression repressor, the expression of the endogenous gene encoding PN7718 is reduced or blocked. See U.S. Pat. No. 5,641,670.

To inhibit the level or activities of a PN7718-containing complex, a PN7718-interacting protein contained therein may additionally be inhibited by the same gene therapy methods described above relating PN7718.

11.3. Methods of Activation

In another embodiment of the methods for modulating PN7718, PN7718-interacting proteins, or PN7718-containing protein complexes, PN7718, PN7718-interacting proteins, or PN7718-containing protein complexes are activated in cells in vitro, or activated in vivo in a patient. For this purpose, the cellular or tissue levels of PN7718, PN7718-interacting proteins, or PN7718-containing protein complexes can be increased by various techniques known in the art. Alternatively, the activities of PN7718, PN7718-interacting proteins, or PN7718-containing protein complexes can be stimulated.

The activation of PN7718, PN7718-interacting proteins, or PN7718-containing protein complexes can be particularly useful in instances where a reduced level and/or activity of PN7718, a PN7718-interacting protein, or a PN7718-containing protein complex is associated with an impaired cellular function (e.g., intracellular calcium signaling, beta-amyloid formation, T-cell receptor and IgE receptor signaling pathways, and protein folding and degradation) or with a particular disease or disorder (e.g., autoimmune diseases, neurological diseases and cardiovascular disorders), or where an increased level and/or activity of PN7718, a PN7718-interacting protein, or a PN7718-containing protein complex would be beneficial to the improvement of a cellular function or a disease state. By increasing the level or activities of PN7718, a PN7718-interacting protein, or a PN7718-containing protein complex, the cellular functions may be modulated and the disease or disorder may be treated or prevented.

11.3.1. Administration of Protein Complex or Protein Members Thereof

Where the level or activity of a particular PN7718-containing protein complex or PN7718 of the present invention in cells in vitro or in vivo is determined to be low or is desired to be increased, the PN7718 protein or the PN7718-containing protein complex may be administered directly to cells in vitro or to a patient needing such treatment. For this purpose, PN7718 proteins and PN7718-containing protein complexes prepared by any one of the methods described in Section 6 may be administered. For administration to patients, it is preferable that the PN7718 proteins or protein complexes are prepared in a pharmaceutical composition as described below in Section 13. Alternatively, both a PN7718 protein and a PN7718-interacting protein can be administered to allow the formation of protein complexes inside cells or in patients. The proteins and protein complexes may be delivered to cells or tissues in vitro or administered to a patient needing treatment by any methods known in the art, e.g., those described in Section 13.

11.3.2. Gene Therapy

In another embodiment, the level and/or activities of PN7718 and/or a particular PN7718-containing protein complex are increased or restored by gene therapy. For example, nucleic acids encoding PN7718 and/or a PN7718-interacting protein can be introduced into tissue cells of a patient needing treatment such that the proteins are expressed from the introduced exogenous nucleic acids. For example, if a disease-causing mutation exists in the gene for PN7718 or a PN7718-interacting protein in a patient, then a nucleic acid encoding the wild-type protein can be introduced into tissue cells of the patient. The exogenous nucleic acid can be used to replace the corresponding endogenous defective gene by, e.g., homologous recombination. See U.S. Pat. No. 6,010,908, which is incorporated herein by reference. Alternatively, if the disease-causing mutation is a recessive mutation, the exogenous nucleic acid is simply used to express a wild-type protein in addition to the endogenous mutant protein. In another approach, the method disclosed in U.S. Pat. No. 6,077,705 may be employed in gene therapy. That is, the patient is administered with both a nucleic acid construct encoding a ribozyme and a nucleic acid construct comprising a ribozyme resistant gene encoding a wild type protein. As a result, undesirable expression of the endogenous gene is inhibited and a desirable wild-type exogenous gene is introduced. In yet another embodiment, if the endogenous gene is of wild-type and the level of expression of the protein encoded thereby is desired to be increased, additional copies of wild-type exogenous genes may be introduced into the patient by gene therapy, or alternatively, a gene activation method such as that disclosed in U.S. Pat. No. 5,641,670 may be used.

In one embodiment, a nucleic acid encoding PN7718 is introduced into tissue cells of a patient needing such treatment. In a specific embodiment, the nucleic acid encoding PN7718 has the sequence of SEQ ID NO:1. In another embodiment, an exogenous nucleic acid encoding a PN7718-interacting protein is introduced into a patient by gene therapy. In a specific embodiment, the PN7718-interacting protein is cyclophilin C. In another specific embodiment, exogenous nucleic acids encoding PN7718 and cyclophilin C are administered to a patient by gene therapy.

Various gene therapy methods are well known in the art. Successes in gene therapy have been reported recently. See e.g., Kay et al., *Nature Genet.,* 24:257–261 (2000); Cavazzana-Calvo et al., *Science,* 288:669 (2000); and Blaese et al., *Science,* 270:475 (1995); Kantoff, et al., J. Exp. Med. 166:219 (1987).

Any suitable gene therapy methods may be used for purposes of the present invention. Generally, a nucleic acid encoding a desirable protein, e.g., one selected from the group of PN7718, cyclophilin C, and other PN7718-interacting proteins is incorporated into a suitable expression vector and is operably linked to a promoter in the vector. Suitable promoters include but are not limited to viral transcription promoters derived from adenovirus, simian virus 40 (SV40) (e.g., the early and late promoters of SV40), Rous sarcoma virus (RSV), and cytomegalovirus (CMV) (e.g., CMV immediate-early promoter), human immunodeficiency virus (HIV) (e.g., long terminal repeat (LTR)), vaccinia virus (e.g., 7.5K promoter), and herpes simplex virus (HSV) (e.g., thymidine kinase promoter). Where tissue-specific expression of the exogenous gene is desirable, tissue-specific promoters may be operably linked to the exogenous gene. In addition, selection markers may also be included in the vector for purposes of selecting, in vitro, those cells that contain the exogenous gene. Various selection markers known in the art may be used including, but not limited to, e.g., genes conferring resistance to neomycin, hygromycin, zeocin, and the like.

In one embodiment, the exogenous nucleic acid (gene) is incorporated into a plasmid DNA vector. Many commercially available expression vectors may be useful for the present invention, including, e.g., pCEP4, pcDNAI, pIND, pSecTag2, pVAX1, pcDNA3.1, and pBI-EGFP, and pDisplay.

Various viral vectors may also be used. Typically, in a viral vector, the viral genome is engineered to eliminate the disease-causing capability, e.g., the ability to replicate in the host cells. The exogenous nucleic acid to be introduced into a patient may be incorporated into the engineered viral genome, e.g., by inserting it into a viral gene that is non-essential to the viral infectivity. Viral vectors are convenient to use as they can be easily introduced into tissue cells by way of infection. Once in the host cell, the recombinant virus typically is integrated into the genome of the host cell. In rare instances, the recombinant virus may also replicate and remain as extrachromosomal elements.

A large number of retroviral vectors have been developed for gene therapy. These include vectors derived from oncoretroviruses (e.g., MLV), lentiviruses (e.g., HIV and SIV) and other retroviruses. For example, gene therapy vectors have been developed based on murine leukemia virus (See, Cepko, et al., Cell, 37:1053–1062 (1984), Cone and Mulligan, Proc. Natl. Acad. Sci. U.S.A., 81:6349–6353 (1984)), mouse mammary tumor virus (See, Salmons et al., Biochem. Biophys. Res. Commun., 159:1191–1198 (1984)), gibbon ape leukemia virus (See, Miller et al., J. Virology, 65:2220–2224 (1991)), HIV, (See Shimada et al., J. Clin. Invest., 88:1043–1047 (1991)), and avian retroviruses (See Cosset et al., J. Virology, 64:1070–1078 (1990)). In addition, various retroviral vectors are also described in U.S. Pat. Nos. 6,168,916; 6,140,111; 6,096,534; 5,985,655; 5,911,983; 4,980,286; and 4,868,116, all of which are incorporated herein by reference.

Adeno-associated virus (AAV) vectors have been successfully tested in clinical trials. See e.g., Kay et al., Nature Genet. 24:257–61 (2000). AAV is a naturally occurring defective virus that requires other viruses such as adenoviruses or herpes viruses as helper viruses. See Muzyczka, Curr. Top. Microbiol. Immun., 158:97 (1992). A recombinant AAV virus useful as a gene therapy vector is disclosed in U.S. Pat. No. 6,153,436, which is incorporated herein by reference.

Adenoviral vectors can also be useful for purposes of gene therapy in accordance with the present invention. For example, U.S. Pat. No. 6,001,816 discloses an adenoviral vector, which is used to deliver a leptin gene intravenously to a mammal to treat obesity. Other recombinant adenoviral vectors may also be used, which include those disclosed in U.S. Pat. Nos. 6,171,855; 6,140,087; 6,063,622; 6,033,908; and 5,932,210, and Rosenfeld et al., Science, 252:431–434 (1991); and Rosenfeld et al., Cell, 68:143–155 (1992).

Other useful viral vectors include recombinant hepatitis viral vectors (See, e.g., U.S. Pat. No. 5,981,274), and recombinant entomopox vectors (See, e.g., U.S. Pat. Nos. 5,721,352 and 5,753,258).

Other non-traditional vectors may also be used for purposes of this invention. For example, International Publication No. WO 94/18834 discloses a method of delivering DNA into mammalian cells by conjugating the DNA to be delivered with a polyelectrolyte to form a complex. The complex may be microinjected into or taken up by cells.

The exogenous gene fragment or plasmid DNA vector containing the exogenous gene may also be introduced into cells by way of receptor-mediated endocytosis. See e.g., U.S. Pat. No. 6,090,619; Wu and Wu, J. Biol. Chem., 263:14621 (1988); Curiel et al., Proc. Natl. Acad. Sci. USA, 88:8850 (1991). For example, U.S. Pat. No. 6,083,741 discloses introducing an exogenous nucleic acid into mammalian cells by associating the nucleic acid to a polycation moiety (e.g., poly-L-lysine, having 3–100 lysine residues), which is itself coupled to an integrin receptor binding moiety (e.g., a cyclic peptide having the amino acid sequence RGD).

Alternatively, the exogenous nucleic acid or vectors containing it can also be delivered into cells via amphiphiles. See e.g., U.S. Pat. No. 6,071,890. Typically, the exogenous nucleic acid or a vector containing the nucleic acid forms a complex with the cationic amphiphile. Mammalian cells contacted with the complex can readily take the complex up.

The exogenous gene can be introduced into a patient for purposes of gene therapy by various methods known in the art. For example, the exogenous gene sequences alone or in a conjugated or complex form described above, or incorporated into viral or DNA vectors, may be administered directly by injection into an appropriate tissue or organ of a patient. Alternatively, catheters or like devices may be used for delivery into a target organ or tissue. Suitable catheters are disclosed in, e.g., U.S. Pat. Nos. 4,186,745; 5,397,307; 5,547,472; 5,674,192; and 6,129,705, all of which are incorporated herein by reference.

In addition, the exogenous gene or vectors containing the gene can be introduced into isolated cells using any known techniques such as calcium phosphate precipitation, microinjection, lipofection, electroporation, gene gun, receptor-mediated endocytosis, and the like. Cells expressing the exogenous gene may be selected and redelivered back to the patient by, e.g., injection or cell transplantation. The appropriate amount of cells delivered to a patient will vary with patient conditions, and desired effect, which can be determined by a skilled artisan. See e.g., U.S. Pat. Nos. 6,054, 288; 6,048,524; and 6,048,729. Preferably, the cells used are autologous, i.e., obtained from the patient being treated.

11.3.3. Small Organic Compounds

The activities of PN7718 and PN7718-containing protein complexes may also be activated by contacting PN7718 or a PN7718-containing protein complex with a compound capable of stimulating the activities of PN7718 or the protein complex.

For example, suitable compounds may include compounds identified with the methods described in Section 10 that are capable of binding PN7718 or a PN7718-containing protein complex, or are capable of triggering or initiating, enhancing or stabilizing protein—protein interactions between PN7718 or a mutant form thereof, and a PN7718-interacting protein, e.g., cyclophilin C, or a mutant form thereof.

In a specific embodiment, a compound capable of enhancing or stabilizing protein—protein interactions between PN7718 and cyclophilin C is administered to cells in vitro, or administered in vivo to a patient to be therapeutically or prophylactically treated.

12. Cell and Animal Models

In another aspect of the present invention, cell and animal models are provided in which PN7718 and/or a PN7718-containing protein complex are in an aberrant form, e.g., increased or decreased level, altered interaction between PN7718 and an interacting protein thereof, and/or altered distribution or localization (e.g., in organs, tissues, cells, or cellular compartments) of PN7718 or the protein complex. Such cell and animal models are useful tools for studying cellular functions and biological processes involving PN7718 and/or a PN7718-containing protein complex, studying disorders and diseases associated with PN7718 and/or a PN7718-containing protein complex, and for testing various methods for modulating the cellular functions and for treating the diseases and disorders.

12.1. Cell Models

Cell models having an aberrant form of one or more of the protein complexes of the present invention are provided in accordance with the present invention.

The cell models may be established by isolating, from a patient, cells having an aberrant form of PN7718 or an aberrant form of a PN7718-containing protein complex. The isolated cells may be cultured in vitro as a primary cell culture. Alternatively, the cells obtained from the primary cell culture or directly from the patient may be immortalized to establish a human cell line. Any methods for constructing immortalized human cell lines may be used in this respect. See generally Yeager and Reddel, *Curr. Opini. Biotech.*, 10:465–469 (1999). For example, the human cells may be immortalized by transfection of plasmids expressing the SV40 early region genes (See e.g., Jha et al., *Exp. Cell Res.*, 245:1–7 (1998)), introduction of the HPV E6 and E7 oncogenes (See e.g., Reznikoff et al., *Genes Dev.*, 8:2227–2240 (1994)), and infection with Epstein-Barr virus (See e.g., Tahara et al., *Oncogene*, 15:1911–1920 (1997)). Alternatively, the human cells may be immortalized by recombinantly expressing the gene for the human telomerase catalytic subunit hTERT in the human cells. See Bodnar et al., *Science*, 279:349–352 (1998).

In alternative embodiments, cell models are provided by recombinantly manipulating appropriate host cells. The host cells may be bacteria cells, yeast cells, insect cells, plant cells, animal cells, and the like. Preferably, the cells are derived from mammals, preferably humans. The host cells may be obtained directly from an individual, or a primary cell culture, or preferably an immortal stable human cell line. In a preferred embodiment, human embryonic stem cells or pluripotent cell lines derived from human stem cells are used as host cells. Methods for obtaining such cells are disclosed in, e.g., Shamblott, et al., *Proc. Natl. Acad. Sci. USA*, 95:13726–13731 (1998) and Thomson et al., *Science*, 282:1145–1147 (1998).

In one embodiment, a cell model is provided by recombinantly expressing PN7718 or a PN7718-containing protein complex of the present invention in cells that do not normally express the protein or protein complex. For example, cells that do not contain a particular protein complex may be engineered to express the protein complex. In a specific embodiment, the PN7718 protein is expressed in a non-human cell. In another specific embodiment, a PN7718-cyclophilin C protein complex is expressed in non-human cells. The cell models may be prepared by introducing into host cells a nucleic acid encoding PN7718 or nucleic acids encoding all interacting protein members required for the formation of a particular protein complex, and expressing the protein members in the host cells. For this purpose, the recombination expression methods described in Section 6 may be used. In addition, the methods for introducing nucleic acids into host cells disclosed in the context of gene therapy in Section 11 may also be used. Preferably, human cells lacking PN7718 protein or a PN7718-containing protein complex to be over-expressed are used as host cells. The host cells may be obtained directly from an individual, or a primary cell culture, or preferably an immortal stable human cell line. In a preferred embodiment, human embryonic stem cells or pluripotent cell lines derived from human stem cells are used as host cells. Methods for obtaining such cells are disclosed in, e.g., Shamblott, et al., *Proc. Natl. Acad. Sci. USA*, 95:13726–13731 (1998), and Thomson et al., *Science*, 282:1145–1147 (1998).

In another embodiment, a cell model over-expressing PN7718 or a PN7718-containing protein complex of the present invention is provided. The cell model may be established by increasing the expression level of PN7718 or one or more of the interacting protein members of the PN7718-containing protein complex. In a specific embodiment, all interacting protein members of a PN7718-containing protein complex are over-expressed. The over-expression may be achieved by introducing into host cells exogenous nucleic acids encoding the proteins to be over-expressed, and selecting those cells that over-express the proteins. The expression of the exogenous nucleic acids may be transient or, preferably stable. The recombinant expression methods described in Section 6, and the methods for introducing nucleic acids into host cells disclosed in the context of gene therapy in Section 11 may be used. Alternatively, the gene activation method disclosed in U.S. Pat. No. 5,641,670 can be useful. Any host cells may be employed for establishing the cell model.

In yet another embodiment, a cell model expressing an abnormally low level of PN7718 or a PN7718-containing protein complex of the present invention is provided. Typically, the cell model is established by genetically manipulating cells that express a normal and detectable level of PN7718 or a PN7718-containing protein complex. In a specific embodiment, the expression level of PN7718 protein is reduced. In another specific embodiment, the expression levels of both PN7718 and cyclophilin C are reduced. The reduced expression may be achieved by "knocking out" the genes encoding PN7718 and/or a PN7718-interacting protein. Alternatively, mutations that can cause reduced expression level (e.g., reduced transcription and/or translation efficiency, and decreased mRNA stability) may also be introduced into the PN7718 gene or a gene encoding a PN7718-interacting protein by homologous recombination. A gene encoding a ribozyme or antisense compound specific to the mRNA encoding PN7718 or a PN7718-interacting protein may also be introduced into the host cells, preferably stably integrated into the genome of the host cells. In addition, a gene encoding an antibody or fragment thereof specific to PN7718 or a PN7718-interacting protein may also be introduced into the host cells. The recombination expression methods described in Sections 6 and 11 can all be used for purposes of manipulating the host cells.

The present invention also contemplates a cell model provided by recombinant DNA methods that exhibits aberrant interactions between the interacting protein members of a protein complex identified in the present invention. For example, variants of the interacting protein members of a particular protein complex exhibiting altered protein—protein interaction properties and the nucleic acid variants encoding such variant proteins may be obtained by random or site-directed mutagenesis in combination with a protein—protein interaction assay system, particularly the yeast two-hybrid system described in Section 4. Essentially, the genes encoding one or more interacting protein members of a particular protein complex may be subject to random or site-specific mutagenesis and the mutated gene sequences are used in yeast two-hybrid system to test the protein—protein interaction characteristics of the protein variants encoded by the gene variants. In this manner, variants of the interacting protein members of the protein complex may be identified that exhibit altered protein—protein interaction properties in forming the protein complex, e.g., increased or decreased binding affinity, and the like. The nucleic acid variants encoding such protein variants may be introduced into host cells by the methods described above, preferably into host cells that normally do not express the interacting proteins. In one embodiment, a cell model is provided having a variant PN7718 protein exhibiting increased or decreased affinity to cyclophilin C.

The cell models of the present invention containing an aberrant form of PN7718 or a PN7718-containing protein complex of the present invention are useful in screening assays for identifying compounds useful in treating diseases and disorders involving intracellular calcium signaling, beta-amyloid formation, T-cell receptor and IgE receptor signaling pathways, and protein folding and degradation such as autoimmune diseases, neurological diseases and cardiovascular disorders. In addition, they may also be used in in vitro pre-clinical assays for testing compounds, such as those identified in the screening assays of the present invention. For example, cells may be contacted with compounds to be tested and assayed for the compound's activity. A variety of parameters relevant to particular physiological disorders or diseases may be analyzed.

12.2. Transgenic Animals

In another aspect of the present invention, transgenic non-human animals are provided having an aberrant expression pattern of PN7718 or a PN7718-containing protein complex. Animals of any species may be used to generate the transgenic animal models, including but not limited to, mice, rats, hamsters, sheep, pigs, rabbits, guinea pigs, preferably non-human primates such as monkeys, chimpanzees, baboons, and the like. Preferably, transgenic mice are provided.

In one embodiment, the transgenic animals are produced to express (human) PN7718 (human) or a (human) PN7718-containing protein complex. In another embodiment, a transgenic animal exhibits over-expression of a PN7718 ortholog. For example, a transgenic mouse may be generated over-expressing the mouse counterpart (ortholog) of PN7718. Over-expression may be exhibited in a tissue or cell that normally expresses the PN7718 ortholog. That is, the level of the PN7718 ortholog is elevated over the normal level. Alternatively, over-expression means that the PN7718 ortholog is expressed in tissues or cells that do not normally express the protein.

To express PN7718 in a transgenic animal, a nucleic acid encoding PN7718 operably linked to a native or non-native promoter may be introduced into at least a portion of the cells of an animal such that PN7718 is expressed in the animal. To over-express a PN7718 ortholog in a transgenic animal, a nucleic acid encoding the PN7718 ortholog may be isolated based on homology to the PN7718 protein or PN7718 nucleic acid by methods known in the art. The isolated PN7718 ortholog nucleic acid may then be transferred into cells of an animal for expression in the animal. Preferably, the ortholog is isolated from an animal of the same species as the animal used for making a transgenic animal. If the expression of the exogenous gene is desired to be limited to a particular tissue, an appropriate tissue-specific promoter may be used. In addition, over-expression may also be achieved by manipulating the native promoter to create mutations that lead to gene over-expression, or by a gene activation method such as that disclosed in U.S. Pat. No. 5,641,670 as described above.

In another embodiment, a transgenic animal is provided which expresses a lower than normal level of PN7718 and/or a PN7718-containing protein complex. In a specific embodiment, the transgenic animal is a "knockout" animal wherein the endogenous gene encoding the PN7718 ortholog is knocked out. In another specific embodiment, the endogenous genes encoding the PN7718 ortholog and the cyclophilin C ortholog, repectively, are both knocked out. Alternatively, mutations that can cause reduced expression level (e.g., reduced transcription and/or translation efficiency, and decreased mRNA stability) may also be introduced into the endogenous genes by homologous recombination. Genes encoding ribozymes or antisense compounds specific to the mRNAs encoding the PN7718 ortholog and/or an ortholog of a PN7718-interacting human protein may also be introduced into the transgenic animal. In addition, genes encoding antibodies or fragments thereof specific to PN7718, a PN7718-interacting protein, or orthologs thereof may also be expressed in a transgenic animal.

In another specific embodiment, a transgenic animal is provided wherein the endogenous gene encoding PN7718 ortholog and the endogenous gene encoding cyclophilin C ortholog are both knocked out, and instead, the transgenic animal expresses (human) cyclophilin C and PN7718.

In yet another embodiment, the transgenic animal of this invention exhibits aberrant interactions between cyclophilin C and PN7718 or between the native ortholog of cyclophilin C and the ortholog of PN7718. For this purpose, variants of PN7718 and cyclophilin C exhibiting altered protein—protein interaction properties and the nucleic acid variants encoding such variant proteins may be obtained by random or site-directed mutagenesis in combination with a protein—protein interaction assay system, particularly the two-hybrid systems described in Sections 4 and 10. For example, variants of PN7718 and cyclophilin C exhibiting increased or decreased or abolished binding affinity to each other may be identified and isolated. The transgenic animal of the present invention may be made to express such protein variants by modifying the endogenous genes. Alternatively, the nucleic acid variants may be introduced exogenously into the transgenic animal genome to express the protein variants therein. In a specific embodiment, endogenous PN7718 ortholog gene and cyclophilin C ortholog gene are knocked out, and the transgenic animal express the above-described variants of PN7718 and cyclophilin C.

Any techniques known in the art for making transgenic animals may be used for purposes of the present invention. For example, the transgenic animals of the present invention may be provided by methods described in, e.g., Jaenisch, *Science*, 240:1468–1474 (1988); Capecchi, et al., *Science,* 244:1288–1291 (1989); Hasty et al., *Nature,* 350:243 (1991); Shinkai et al., *Cell,* 68:855 (1992); Mombaerts et al., *Cell,* 68:869 (1992); Philpott et al., *Science,* 256:1448 (1992); Snouwaert et al., *Science,* 257:1083 (1992); Donehower et al., *Nature,* 356:215 (1992); Hogan et al., *Manipulating the Mouse Embryo; A Laboratory Manual,* $2^{nd}$ edition, Cold Spring Harbor Laboratory Press, 1994; and U.S. Pat. Nos. 4,873,191; 5,800,998; 5,891,628, all of which are incorporated herein by reference.

Generally, the founder lines may be established by introducing appropriate exogenous nucleic acids into, or modifying an endogenous gene in, germ lines, embryonic stem cells, embryos, or sperm which are then used in producing a transgenic animal. The gene introduction may be conducted by various methods including those described in Sections 2.2, 6.1 and 6.2. See also, Van der Putten et al., *Proc. Natl. Acad. Sci. USA,* 82:6148–6152 (1985); Thompson et al., *Cell,* 56:313–321 (1989); Lo, *Mol. Cell. Biol.,* 3:1803–1814 (1983); Gordon, *Trangenic Animals, Intl. Rev. Cytol.* 115:171–229 (1989); and Lavitrano et al., *Cell,* 57:717–723 (1989). In a specific embodiment, the exogenous gene is incorporated into an appropriate vector, such as those described in Sections 2.2 and 6.2, and is transformed into embryonic stem (ES) cells. The transformed ES cells are then injected into a blastocyst. The blastocyst with the transformed ES cells is then implanted into a surrogate mother animal. In this manner, a chimeric founder line animal containing the exogenous nucleic acid (transgene) may be produced.

Preferably, site-specific recombination is employed to integrate the exogenous gene into a specific predetermined site in the animal genome, or to replace an endogenous gene or a portion thereof with the exogenous sequence. Various site-specific recombination systems may be used including those disclosed in Sauer, *Curr. Opin. Biotechnol.,* 5:521–527 (1994); and Capecchi, et al., *Science,* 244:1288–1291 (1989), and Gu et al., *Science,* 265:103–106 (1994). Specifically, the Cre/lox site-specific recombination system known in the art may be conveniently used which employs the bacteriophage P1 protein Cre recombinase and its recognition sequence loxP. See Rajewsky et al., *J. Clin. Invest.,* 98:600–603 (1996); Sauer, *Methods,* 14:381–392 (1998); Gu et al., *Cell,* 73:1155–1164 (1993); Araki et al., *Proc. Natl. Acad. Sci. USA,* 92:160–164 (1995); Lakso et al., *Proc. Natl. Acad. Sci. USA,* 89:6232–6236 (1992); and Orban et al., *Proc. Natl. Acad. Sci. USA,* 89:6861–6865 (1992).

The transgenic animals of the present invention may be transgenic animals that carry a transgene in all cells or mosaic transgenic animals carrying a transgene only in certain cells, e.g., somatic cells. The transgenic animals may have a single copy or multiple copies of a particular transgene.

The founder transgenic animals thus produced may be bred to produce various offspring. For example, they can be inbred, outbred, and crossbred to establish homozygous lines, heterozygous lines, and compound homozygous or heterozygous lines.

13. Pharmaceutical Compositions and Formulations

In another aspect of the present invention, pharmaceutical compositions are also provided containing one or more of the therapeutic agents provided in the present invention. The compositions are prepared as a pharmaceutical formulation suitable for administration into a patient. Accordingly, the present invention also extends to pharmaceutical compositions, medicaments, drugs or other compositions containing one or more of the therapeutic agent in accordance with the present invention.

For example, such therapeutic agents include, but are not limited to, (1) PN7718 protein or fragments or homologues or derivatives thereof, particularly small PN7718 fragments (containing, e.g., 5 to 20, 30, 50, 75 or 100 or 150 amino acids) capable of binding cyclophilin C, (2) PN7718 nucleic acid or fragments thereof, (3) compounds capable of binding or modulating PN7718 protein, (4) small organic compounds selected based on the screening methods of the present invention capable of interfering with the interaction between cyclophilin C and PN7718, (5) antisense compounds specifically hybridizable to cyclophilin C nucleic acids (gene or mRNA) (6) antisense compounds specific to the gene or mRNA of PN7718, (7) ribozyme compounds specific to cyclophilin C nucleic acids (gene or mRNA), (8) ribozyme compounds specific to the gene or mRNA of PN7718, (9) antibodies immunoreactive with cyclophilin C or PN7718, (10) antibodies selectively immunoreactive with a protein complex of the present invention, (11) small organic compounds capable of binding a protein complex of the present invention, (12) small peptide compounds as described above (optionally linked to a transporter) capable of interacting with cyclophilin C or PN7718, (13) nucleic acids encoding the antibodies or peptides, etc.

The compositions are prepared as a pharmaceutical formulation suitable for administration into a patient. Accordingly, the present invention also extends to pharmaceutical compositions, medicaments, drugs or other compositions containing one or more of the therapeutic agents in accordance with the present invention.

In the pharmaceutical composition, an active compound identified in accordance with the present invention can be in any pharmaceutically acceptable salt form. As used herein, the term "pharmaceutically acceptable salts" refers to the relatively non-toxic, organic or inorganic salts of the compounds of the present invention, including inorganic or organic acid addition salts of the compound. Examples of such salts include, but are not limited to, hydrochloride salts, sulfate salts, bisulfate salts, borate salts, nitrate salts, acetate salts, phosphate salts, hydrobromide salts, laurylsulfonate salts, glucoheptonate salts, oxalate salts, oleate salts, laurate salts, stearate salts, palmitate salts, valerate salts, benzoate salts, naththylate salts, mesylate salts, tosylate salts, citrate salts, lactate salts, maleate salts, succinate salts, tartrate salts, fumarate salts, and the like. See, e.g., Berge, et al., *J. Pharm. Sci.,* 66:1–19 (1977). Examples of pharmaceutically acceptable salts may also include alkali metal salts, alkaline earth salts, and ammonium salts. Thus, suitable salts may be salts of aluminum, calcium, lithium, magnesium, potassium, sodium and zinc. In addition, organic salts may also be used including, e.g., salts of lysine, N,N'-dibenzylethylenediamine, chloroprocaine, choline, diethanolamine, ethylenediamine, meglumine (N-methylglucamine), procaine and tris.

For oral delivery, the active compounds can be incorporated into a formulation that includes pharmaceutically acceptable carriers such as binders (e.g., gelatin, cellulose, gum tragacanth), excipients (e.g., starch, lactose), lubricants (e.g., magnesium stearate, silicon dioxide), disintegrating agents (e.g., alginate, Primogel, and corn starch), and sweetening or flavoring agents (e.g., glucose, sucrose, saccharin, methyl salicylate, and peppermint). The formulation can be orally delivered in the form of enclosed gelatin capsules or compressed tablets. Capsules and tablets can be prepared in any conventional techniques. The capsules and tablets can also be coated with various coatings known in the art to modify the flavors, tastes, colors, and shapes of the capsules and tablets. In addition, liquid carriers such as fatty oil can also be included in capsules.

Suitable oral formulations can also be in the form of suspension, syrup, chewing gum, wafer, elixir, and the like. If desired, conventional agents for modifying flavors, tastes, colors, and shapes of the special forms can also be included. In addition, for convenient administration by enteral feeding tube in patients unable to swallow, the active compounds can be dissolved in an acceptable lipophilic vegetable oil vehicle such as olive oil, corn oil and safflower oil.

The active compounds can also be administered parenterally in the form of solution or suspension, or in lyophilized form capable of conversion into a solution or suspension form before use. In such formulations, diluents or pharmaceutically acceptable carriers such as sterile water and physiological saline buffer can be used. Other conventional solvents, pH buffers, stabilizers, anti-bacteria agents, surfactants, and antioxidants can all be included. For example, useful components include sodium chloride, acetates, citrates or phosphates buffers, glycerin, dextrose, fixed oils, methyl parabens, polyethylene glycol, propylene glycol, sodium bisulfate, benzyl alcohol, ascorbic acid, and the like. The parenteral formulations can be stored in any conventional containers such as vials and ampoules.

Routes of topical administration include nasal, bucal, mucosal, rectal, or vaginal applications. For topical administration, the active compounds can be formulated into lotions, creams, ointments, gels, powders, pastes, sprays, suspensions, drops and aerosols. Thus, one or more thickening agents, humectants, and stabilizing agents can be included in the formulations. Examples of such agents include, but are not limited to, polyethylene glycol, sorbitol, xanthan gum, petrolatum, beeswax, or mineral oil, lanolin, squalene, and the like. A special form of topical administration is delivery by a transdermal patch. Methods for preparing transdermal patches are disclosed, e.g., in Brown, et al., *Annual Review of Medicine,* 39:221–229 (1988), which is incorporated herein by reference.

Subcutaneous implantation for sustained release of the active compounds may also be a suitable route of administration. This entails surgical procedures for implanting an active compound in any suitable formulation into a subcutaneous space, e.g., beneath the anterior abdominal wall. See, e.g., Wilson et al., *J. Clin. Psych.* 45:242–247 (1984). Hydrogels can be used as a carrier for the sustained release of the active compounds. Hydrogels are generally known in the art. They are typically made by crosslinking high molecular weight biocompatible polymers into a network, which swells in water to form a gel like material. Preferably, hydrogels are biodegradable or biosorbable. For purposes of this invention, hydrogels made of polyethylene glycols, collagen, or poly(glycolic-co-L-lactic acid) may be useful. See, e.g., Phillips et al., *J. Pharmaceut. Sci.* 73:1718–1720 (1984).

The active compounds can also be conjugated, to a water soluble non-immunogenic non-peptidic high molecular weight polymer to form a polymer conjugate. For example, an active compound is covalently linked to polyethylene glycol to form a conjugate. Typically, such a conjugate exhibits improved solubility, stability, and reduced toxicity and immunogenicity. Thus, when administered to a patient, the active compound in the conjugate can have a longer half-life in the body, and exhibit better efficacy. See generally, Burnham, *Am. J. Hosp. Pharm.,* 15:210–218 (1994). PEGylated proteins are currently being used in protein replacement therapies and for other therapeutic uses. For example, PEGylated interferon (PEG-INTRON A®) is clinically used for treating Hepatitis B. PEGylated adenosine deaminase (ADAGEN®) is being used to treat severe combined immunodeficiency disease (SCIDS). PEGylated L-asparaginase (ONCAPSPAR®) is being used to treat acute lymphoblastic leukemia (ALL). It is preferred that the covalent linkage between the polymer and the active compound and/or the polymer itself is hydrolytically degradable under physiological conditions. Such conjugates known as "prodrugs" can readily release the active compound inside the body. Controlled release of an active compound can also be achieved by incorporating the active ingredient into microcapsules, nanocapsules, or hydrogels generally known in the art.

Liposomes can also be used as carriers for the active compounds of the present invention. Liposomes are micelles made of various lipids such as cholesterol, phospholipids, fatty acids, and derivatives thereof. Various modified lipids can also be used. Liposomes can reduce the toxicity of the active compounds, and increase their stability. Methods for preparing liposomal suspensions containing active ingredients therein are generally known in the art. See, e.g., U.S. Pat. No. 4,522,811; Prescott, Ed., *Methods in Cell Biology,* Volume XIV, Academic Press, New York, N.Y. (1976).

The active compounds can also be administered in combination with another active agent that synergistically treats or prevents the same symptoms or is effective for another disease or symptom in the patient treated so long as the other active agent does not interfere with or adversely affect the effects of the active compounds of this invention. Such other active agents include but are not limited to anti-inflammation agents, antiviral agents, antibiotics, antifungal agents, antithrombotic agents, cardiovascular drugs, cholesterol lowering agents, anti-cancer drugs, hypertension drugs, and the like.

Generally, the toxicity profile and therapeutic efficacy of the therapeutic agents can be determined by standard pharmaceutical procedures in cell models or animal models, e.g., those provided in Section 7. As is known in the art, the $LD_{50}$ represents the dose lethal to about 50% of a tested population. The $ED_{50}$ is a parameter indicating the dose therapeutically effective in about 50% of a tested population. Both $LD_{50}$ and $ED_{50}$ can be determined in cell models and animal models. In addition, the $IC_{50}$ may also be obtained in cell models and animal models, which stands for the circulating plasma concentration that is effective in achieving about 50% of the maximal inhibition of the symptoms of a disease or disorder. Such data may be used in designing a dosage range for clinical trials in humans. Typically, as will be apparent to skilled artisans, the dosage range for human use should be designed such that the range centers around the ED$_{50}$ and/or IC$_{50}$, but significantly below the LD$_{50}$ obtained from cell or animal models.

It will be apparent to skilled artisans that the therapeutically effective amount for each active compound to be included in a pharmaceutical composition of the present invention can vary with factors including but not limited to the activity of the compound used, stability of the active compound in the patient's body, the severity of the conditions to be alleviated, the total weight of the patient treated, the route of administration, the ease of absorption, distribution, and excretion of the active compound by the body, the age and sensitivity of the patient to be treated, and the like. The amount of administration can also be adjusted as the various factors change over time.

14. EXAMPLES

1. Yeast Two-Hybrid System

The principles and methods of the yeast two-hybrid system have been described in detail. See Bartel and Fields, eds., *The Yeast Two-Hybrid System*, Oxford University Press, New York, N.Y., 1997. The following is thus a description of the particular procedure that we used, which was applied to all proteins.

The cDNA encoding the bait protein was generated by PCR from cDNA prepared from a desired tissue. The cDNA product was then introduced by recombination into the yeast expression vector pGBT.Q, which is a close derivative of pGBT.C (See Bartel et al., *Nat Genet.*, 12:72–77 (1996)) in which the polylinker site has been modified to include M13 sequencing sites. The new construct was selected directly in the yeast strain PNY200 for its ability to drive tryptophane synthesis (genotype of this strain: MATα trp1-901 leu2-3, 112 ura3-52 his3-200 ade2 gal4Δ gal80). In these yeast cells, the bait was produced as a C-terminal fusion protein with the DNA binding domain of the transcription factor Gal4 (amino acids 1 to 147). Prey libraries were transformed into the yeast strain BK100 (genotype of this strain: MATa trp1-901 leu2-3,112 ura3-52 his3-200 gal4Δ gal80 LYS2::GAL-HIS3 GAL2-ADE2 met2::GAL7-lacZ), and selected for the ability to drive leucine synthesis. In these yeast cells, each cDNA was expressed as a fusion protein with the transcription activation domain of the transcription factor Gal4 (amino acids 768 to 881) and a 9 amino acid hemagglutinin epitope tag. PNY200 cells (MATα mating type), expressing the bait, were then mated with BK100 cells (MATa mating type), expressing prey proteins from a prey library. The resulting diploid yeast cells expressing proteins interacting with the bait protein were selected for the ability to synthesize tryptophan, leucine, histidine, and adenine. DNA was prepared from each clone, transformed by electroporation into *E. coli* strain KC8 (Clontech KC8 electrocompetent cells, Catalog No. C2023-1), and the cells were selected on ampicillin-containing plates in the absence of either tryptophane (selection for the bait plasmid) or leucine (selection for the library plasmid). DNA for both plasmids was prepared and sequenced by the dideoxynucleotide chain termination method. The identity of the bait cDNA insert was confirmed and the cDNA insert from the prey library plasmid was identified using the BLAST program to search against public nucleotide and protein databases. Plasmids from the prey library were then individually transformed into yeast cells together with a plasmid driving the synthesis of lamin and 5 other test proteins, respectively, fused to the Gal4 DNA binding domain. Clones that gave a positive signal in the β-galactosidase assay were considered false-positives and discarded. Plasmids for the remaining clones were transformed into yeast cells together with the original bait plasmid. Clones that gave a positive signal in the β-galactosidase assay were considered true positives.

Bait sequences indicated in Table I were used in the yeast two-hybrid system described above. The isolated prey sequences are summarized in Table I. The GenBank Accession No. for the bait protein is also provided in Table I, upon which the bait and prey sequences are aligned.

2. Production of Antibodies Selectively Immunoreactive with Protein Complex

The cyclophilin C-interacting domain of PN7718 and the PN7718-interacting domain of cyclophilin C are indicated in Table I in Section 2. Both interacting domains are recombinantly expressed in *E. coli.* and isolated and purified. A protein complex is formed by mixing the two purified interacting domains. A protein complex is also formed by mixing recombinantly expressed intact complete cyclophilin C and PN7718. The two protein complexes are used as antigens in immunizing a mouse. mRNA is isolated from the immunized mouse spleen cells, and first-strand cDNA is synthesized based on the mRNA. The V$_H$ and V$_K$ genes are amplified from the thus synthesized cDNAs by PCR using appropriate primers.

The amplified V$_H$ and V$_K$ genes are ligated together and subcloned into a phagemid vector for the construction of a phage display library. *E. coli.* cells are transformed with the ligation mixtures, and thus a phage display library is established. Alternatively, the ligated V$_H$ and V$_k$ genes are subcloned into a vector suitable for ribosome display in which the V$_H$-V$_k$ sequence is under the control of a T7 promoter. See Schaflitzel et al., *J. Immun. Meth.*, 231:119–135 (1999).

The libraries are screened with the cyclophilin C-PN7718 complex and individual cyclophilin C and PN7718. Several rounds of screening are preferably performed. Clones corresponding to scFv fragments that bind the cyclophilin C-PN7718 complex, but not the individual cyclophilin C and PN7718 are selected and purified. A single purified clone is used to prepare an antibody selectively immunoreactive with the cyclophilin C-PN7718 complex. The antibody is then verified by an immunochemistry method such as RIA and ELISA.

In addition, the clones corresponding to scFv fragments that bind the cyclophilin C-PN7718 complex and also binds cyclophilin C and/or PN7718 may be selected. The scFv genes in the clones are diversified by mutagenesis methods such as oligonucleotide-directed mutagenesis, error-prone PCR (See Lin-Goerke et al., *Biotechniques,* 23:409 (1997)), dNTP analogues (See Zaccolo et al., *J. Mol. Biol.,* 255:589 (1996)), and other methods. The diversified clones are further screened in phage display or ribosome display libraries. In this manner, scFv fragments selectively immunoreactive with the cyclophilin C-PN7718 complex may be obtained.

3. Yeast Screen to Identify Small Molecule Inhibitors of the Interaction Between Cyclophilin C and PN7718

Beta-galactosidase is used as a reporter enzyme to signal the interaction between yeast two-hybrid protein pairs expressed from plasmids in *Saccharomyces cerevisiae*. Yeast strain MY209 (ade2 his3 leu2 trp1 cyh2 ura3::GAL1p-lacZ gal4 gal80 lys2::GAL1p-HIS3) bearing one plasmid with the genotype of LEU2 CEN4 ARS1 ADH1p-SV40NLS-GAL4 (768–881)-PN7718-PGK1t AmpR ColE1_ori, and another plasmid having a genotype of TRP1 CEN4 ARS ADH1p-GAL4(1–147)-cyclophilin C-ADH1t AmpR ColE1_ori is cultured in synthetic complete media lacking leucine and tryptophan (SC-Leu-Trp) overnight at 30° C. The cyclophilin C and PN7718 nucleic acids in the plasmids can code for the full-length cyclophilin C and PN7718 proteins, respectively, or fragments thereof. This culture is diluted to 0.01 $OD_{630}$ units/ml using SC-Leu-Trp media. The diluted MY209 culture is dispensed into 96-well microplates. Compounds from a library of small molecules are added to the microplates; the final concentration of test compounds is approximately 60 µM. The assay plates are incubated at 30° C. overnight.

The following day an aliquot of concentrated substrate/lysis buffer is added to each well and the plates incubated at 37° C. for 1–2 hours. At an appropriate time an aliquot of stop solution is added to each well to halt the beta-galactosidase reaction. For all microplates an absorbance reading is obtained to assay the generation of product from the enzyme substrate. The presence of putative inhibitors of the interaction between cyclophilin C and PN7718 results in inhibition of the beta-galactosidase signal generated by MY209. Additional testing eliminates compounds that decreased expression of beta-galactosidase by affecting yeast cell growth and non-specific inhibitors that affected the beta-galactosidase signal generated by the interaction of an unrelated protein pair.

Once a hit, i.e., a compound which inhibits the interaction between the interacting proteins, is obtained, the compound is identified and subjected to further testing wherein the compounds are assayed at several concentrations to determine an $IC_{50}$ value, this being the concentration of the compound at which the signal seen in the two-hybrid assay described in this Example is 50% of the signal seen in the absence of the inhibitor.

4. Enzyme-Linked Immunosorbent Assay (ELISA)

pGEX5X-2 (Amersham Biosciences; Uppsala, Sweden) is used for the expression of a GST-PN7718 fusion protein. The pGEX5X-2-PN7718 construct is transfected into *Escherichia coli* strain DH5α (Invitrogen; Carlsbad, Calif.) and fusion protein is prepared by inducing log phase cells (O.D. 595=0.4) with 0.2 mM isopropyl-β-D-thiogalactopyranoside (IPTG). Cultures are harvested after approximately 4 hours of induction, and cells pelleted by centrifugation. Cell pellets are resuspended in lysis buffer (1% nonidet P-40 [NP-40], 150 mM NaCl, 10 mM Tris pH 7.4, 1 mM ABESF [4-(2-aminoethyl) benzenesulfonyl fluoride]), lysed by sonication and the lysate cleared of insoluble materials by centrifugation. Cleared lysate is incubated with Glutathione Sepharose beads (Amersham Biosciences; Uppsala, Sweden) followed by thorough washing with lysis buffer. The GST-PN7718 fusion protein is then eluted from the beads with 5 mM reduced glutathione. Eluted protein is dialyzed against phosphate buffer saline (PBS) to remove the reduced glutathione.

A stable *Drosophila* Schneider 2 (S2) myc-cyclophilin C expression cell line is generated by transfecting S2 cells with pCoHygro (Invitrogen; Carlsbad, Calif.) and an expression vector that directs the expression of the myc-cyclophilin C fusion protein. Briefly, S2 cells are washed and re-suspended in serum free Express Five media (Invitrogen; Carlsbad, Calif.). Plasmid/liposome complexes are then added (NovaFECTOR, Venn Nova; Pompano Beach, Fla.) and allowed to incubate with cells for 12 hours under standard growth conditions (room temperature, no $CO_2$ buffering). Following this incubation period fetal bovine serum is added to a final concentration of 20% and cells are allowed to recover for 24 hours. The media is replaced and cells are grown for an additional 24 hours. Transfected cells are then selected in 350 µg/ml hygromycin for three weeks. Expression of myc-cyclophilin C is confirmed by Western blotting. This cell line is referred to as S2-myc-cyclophilin C.

GST-PN7718 fusion protein is immobilized to wells of an ELISA plate as follows: Nunc Maxisorb 96 well ELISA plates (Nalge Nunc International; Rochester, N.Y.) are incubated with 100 µl of 10 µg/ml of GST-PN7718 in 50 mM carbonate buffer (pH 9.6) and stored overnight at 4° Celsius. This plate is referred to as the ELISA plate.

A compound dilution plate is generated in the following manner. In a 96 well polypropylene plate (Greiner, Germany) 50 µl of DMSO is pipetted into columns 2–12. In the same polypropylene plate pipette, 10 µl of each compound being tested for its ability to modulate protein—protein interactions is plated in the wells of column 1 followed by 90 µl of DMSO (final volume of 100 µl). Compounds selected from primary screens or from virtual screening, or designed based on the primary screen hits are then serially diluted by removing 50 µl from column 1 and transferring it to column 2 (50:50 dilution). Serial dilutions are continued until column 10. This plate is termed the compound dilution plate.

Next, 12 µl from each well of the compound dilution plate is transferred into its corresponding well in a new polypropylene plate. 108 µl of S2-myc-cyclophilin C-containing lysate ($1 \times 10^6$ cell equivalents/ml) in phosphate buffered saline is added to all wells of columns 1–11. 108 µl of phosphate buffered saline without lysate is added into all wells of column 12. The plate is then mixed on a shaker for 15 minutes. This plate is referred to as the compound preincubation plate.

The ELISA plate is emptied of its contents and 4001 µl of Superblock (Pierce Endogen; Rockford, Ill.) is added to all the wells and allowed to sit for 1 hour at room temperature. 100 µl from all columns of the compound preincubation plate are transferred into the corresponding wells of the ELISA binding plate. The plate is then covered and allowed to incubate for 1.5 hours room temperature.

The interaction of the myc-tagged cyclophilin C with the immobilized GST-PN7718 is detected by washing the ELISA plate followed by an incubation with 100 µl/well of 1 µg/ml of mouse anti-myc IgG (clone 9E10; Roche Applied Science; Indianapolis, Ind.) in phosphate buffered saline. After 1 hour at room temperature, the plates are washed with phosphate buffered saline and incubated with 100 µl/well of 250 ng/ml of goat anti-mouse IgG conjugated to horseradish peroxidase in phosphate buffer saline. Plates are then washed again with phosphate buffered saline and incubated with the fluorescent substrate solution Quantiblu (Pierce Endogen; Rockford, Ill.). Horseradish peroxidase activity is then measured by reading the plates in a fluorescent plate reader (325 nm excitation, 420 nm emission).

5. Tissue Expression Analysis

A PN7718 DNA fragment corresponding to nucleotides 177–447 of the sequence of SEQ ID NO:1 was amplified by PCR from a cDNA library. The fragment was labeled with radioactive isotope $P^{32}$ using the Prime-it RmT Random Primer Labeling Kit from Stratagene, San Diego, Calif. The labeled probe was purified using the NucTrap Probe Purification Kit from Stratagene, San Diego, Calif.

Clontech Multiple Tissue Northern Blot (Catalog No. 7760-1) was used for Northern hybridization. Hybridization was carried out in Expresshyb solution (Catalog No. 8015-2) obtained from Clontech Inc., Palo Alto, Calif. in a hybridization tube in the presence of the labeled PN9845 probe and 0.1 mg/ml of sheared salmon sperm DNA for two hours. The blot was washed with a wash solution having 2×SSC and 1% SDS at a temperature of up to 65° C. Hybridization signals were detected using Molecular Dynamics Storm Bed 860 phosphoimager and Image Quant Analysis Software. The resulting image is shown in FIG. 1.

6. Aβ Secretion Assay

To test the compounds capable of binding PN7718 or modulating the PN7718-cyclophillin C interaction, H4 neuroglioma cells expressing APP695NL and CHO cells stably expressing wild-type human APP751 and human mutant presenilin 1 (PS1) M146L are used. Generation and culture of these cells have been described. See Murphy et al., *J. Biol. Chem.*, 274(17): 11914–11923 (1999); Murphy et al., *J. Biol. Chem.*, 275(34):26277–26284 (2000). To minimize toxic effects of the tested compounds, the H4 cells are incubated for 6 hours in the presence of the various compounds. To evaluate the potential for toxic effects of the tested compounds, additional aliquots of cells are incubated in parallel with each compound. The supernatants are analyzed for the presence of lactate dehydrogenase (LDH) as a measure of cellular toxicity.

After incubating the cells with the test compounds for a pre-determined time period, sandwich enzyme-linked immunosorbent assay (ELISA) is employed to measure secreted Aβ(Aβ42 and/or Aβ40) levels as described previously. Murphy et al., *J. Biol. Chem.*, 275(34):26277–26284 (2000). For cell culture studies serum free media samples are collected following 6–12 hours of conditioning, Complete Protease Inhibitor Cocktail added (PIC; Roche), and total Aβ concentration measured by 3160/BA27 sandwich ELISA for Aβ40 and 3160/BC05 sandwich ELISA for Aβ42. All measurements are performed in triplicate. Antibody 3160 is an affinity purified polyclonal antibody raised against Aβ1-40. HRP conjugated monoclonal antibodies BA27 for detection of Aβ40 and BC05 for detection of Aβ42 have been previously described. Suzuki et al., *Science*, 264(5163):1336–1340 (1994).

Although the foregoing invention has been described in some detail by way of illustration and example for purposes of clarity of understanding, it will be obvious that certain changes and modifications may be practiced within the scope of the appended claims.

In various parts of this disclosure, certain publications or patents are discussed or cited. The mere discussion of, or reference to, such publications or patents is not intended as admission that they are prior art to the present invention.

What is claimed is:

1. An isolated polynucleotide comprising a nucleic acid sequence selected from the group consisting of: SEQ ID NO:1, SEQ ID NO:3, SEQ ID NO:5, and the complements thereof.

2. A method for making an isolated polypeptide having the amino acid sequence of SEQ ID NO:2, comprising: providing an expression vector having the nucleic acid sequence of SEQ ID NO:1 or SEQ ID NO:3 of claim 1; and introducing said expression vector into a host cell such that said host cell produces the isolated polypeptide.

3. The isolated polynucleotide of claim 1 having the nucleic acid sequence of SEQ ID NO:1 or SEQ ID NO:3 encoding a polypeptide having the amino acid sequence of SEQ ID NO:2.

4. The isolated polynucleotide of claim 1 having the nucleic acid sequence of SEQ ID NO:5.

5. A method for making an isolated polypeptide, comprising: providing an expression vector having the sequence of SEQ ID NO:5 of claim 1; and introducing said expression vector into a host cell such that said host cell produces the isolated polypeptide.

6. A nucleic acid vector comprising the isolated polynucleotide of claim 1.

7. A host cell comprising the isolated polynucleotide of claim 1, wherein said host cell is not a human being.

* * * * *

UNITED STATES PATENT AND TRADEMARK OFFICE
CERTIFICATE OF CORRECTION

| | |
|---|---|
| PATENT NO. | : 7,067,312 B1 |
| APPLICATION NO. | : 10/247146 |
| DATED | : June 27, 2006 |
| INVENTOR(S) | : Bartel et al. |

Page 1 of 1

It is certified that error appears in the above-identified patent and that said Letters Patent is hereby corrected as shown below:

Title page Item (54), in the Title line, before "PN7718", please add --NOVEL--.

Title page Item (74), in the Attorney, Agent, or Firm line, please change "Zheng" to --Zhang--.

Signed and Sealed this

Tenth Day of April, 2007

JON W. DUDAS
*Director of the United States Patent and Trademark Office*